(12) United States Patent
Dimitrov et al.

(10) Patent No.: US 11,939,377 B2
(45) Date of Patent: Mar. 26, 2024

(54) AFFINITY MATURED CD22-SPECIFIC MONOCLONAL ANTIBODY AND USES THEREOF

(71) Applicant: The U.S.A., as represented by the Secretary, Department of Health and Human Services, Bethesda, MD (US)

(72) Inventors: Dimiter S. Dimitrov, Pittsburgh, PA (US); Zhongyu Zhu, Frederick, MD (US); Sneha Ramakrishna, Bethesda, MD (US); Terry J. Fry, Aurora, CO (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 557 days.

(21) Appl. No.: 17/259,334

(22) PCT Filed: Jul. 11, 2019

(86) PCT No.: PCT/US2019/041401
§ 371 (c)(1),
(2) Date: Jan. 11, 2021

(87) PCT Pub. No.: WO2020/014482
PCT Pub. Date: Jan. 16, 2020

(65) Prior Publication Data
US 2021/0324074 A1    Oct. 21, 2021

Related U.S. Application Data

(60) Provisional application No. 62/697,185, filed on Jul. 12, 2018.

(51) Int. Cl.
*C07K 16/28* (2006.01)
*A61K 31/365* (2006.01)
*A61K 35/17* (2015.01)
*A61K 39/00* (2006.01)
*A61K 47/68* (2017.01)
*C07K 14/705* (2006.01)
*G01N 33/574* (2006.01)

(52) U.S. Cl.
CPC ........ *C07K 16/2803* (2013.01); *A61K 31/365* (2013.01); *A61K 35/17* (2013.01); *A61K 47/6803* (2017.08); *A61K 47/6851* (2017.08); *C07K 14/705* (2013.01); *G01N 33/574* (2013.01); *A61K 2039/505* (2013.01); *C07K 2317/31* (2013.01); *C07K 2317/53* (2013.01); *C07K 2317/565* (2013.01); *C07K 2317/94* (2013.01); *C07K 2319/02* (2013.01); *C07K 2319/03* (2013.01)

(58) Field of Classification Search
CPC .................................................. C07K 16/2803
See application file for complete search history.

(56) References Cited

U.S. PATENT DOCUMENTS

2017/0204178 A1*  7/2017  Finney ................... C07K 16/18

FOREIGN PATENT DOCUMENTS

| WO | WO 2009/124109 | 10/2009 |
| WO | WO 2013/059593 | 4/2013 |
| WO | WO 2014/065961 | 5/2014 |
| WO | WO 2016/164731 | 10/2016 |
| WO | WO 2017/216561 | 12/2017 |

OTHER PUBLICATIONS

Biberacher et al., "The cytotoxicity of anti-CD22 immunotoxin is enhanced by bryostatin 1 in B-cell lymphomas through CD22 upregulation and PKC-βII depletion," *Haematologica* 97(5): 771-779, 2012.
International Search Report and Written Opinion of PCT/US2019/041401, dated Oct. 21, 2019 (14 pages).
Li et al., "In Vitro Affinity Maturation of a Natural Human Antibody Overcomes a Barrier to in vivo Affinity Maturation," *mAbs*, vol. 6:437-445, 2014.
Rajpal et al., "A General Method for Greatly Improving the Affinity of Antibodies by Using Combinatorial Libraries," *Proc. Natl. Acad. Sci. U.S.A.*, vol. 102:8466-8471, 2005.
Ramakrishna et al., "Modulation of CD22 Antigen Density Improves Efficacy of CD22 Chimeric Antigen Receptor (CAR) T Cells Against CD22$^{lo}$ B-Lineage Leukemia and Lymphoma," *Blood*, vol. 130:3894, 2017.
Ramakrishna et al., "Modulation of Target Antigen Density Improves CAR T-cell Functionality and Persistence," *Clin Cancer Res* 25:5329-5341, 2019.
Tiller et al., "Facile Affinity Maturation of Antibody Variable Domains Using Natural Diversity Mutagenesis," *Front. Immunol.*, vol. 8, pp. 1-16, 2017.
Xiao et al., "Identification and Characterization of Fully Human Anti-CD22 Monoclonal Antibodies," *mAbs*, vol. 1:297-303, 2009.

* cited by examiner

*Primary Examiner* — Adam Weidner
*Assistant Examiner* — Ashley H. Gao
(74) *Attorney, Agent, or Firm* — Klarquist Sparkman, LLP

(57) ABSTRACT

An affinity matured anti-CD22 human monoclonal antibody exhibiting significantly higher affinity (less than 50 pM) compared to the parental antibody (affinity of about 2 nM) is described. The anti-CD22 variant antibody or a fragment thereof, such as a single-chain variable fragment (scFv), can be used as the antigen-binding portion of chimeric antigen receptors (CARs), antibody-drug conjugates (ADCs), immunotoxins or multi-specific antibodies for the treatment of B-cell malignancies.

35 Claims, 46 Drawing Sheets

Specification includes a Sequence Listing.

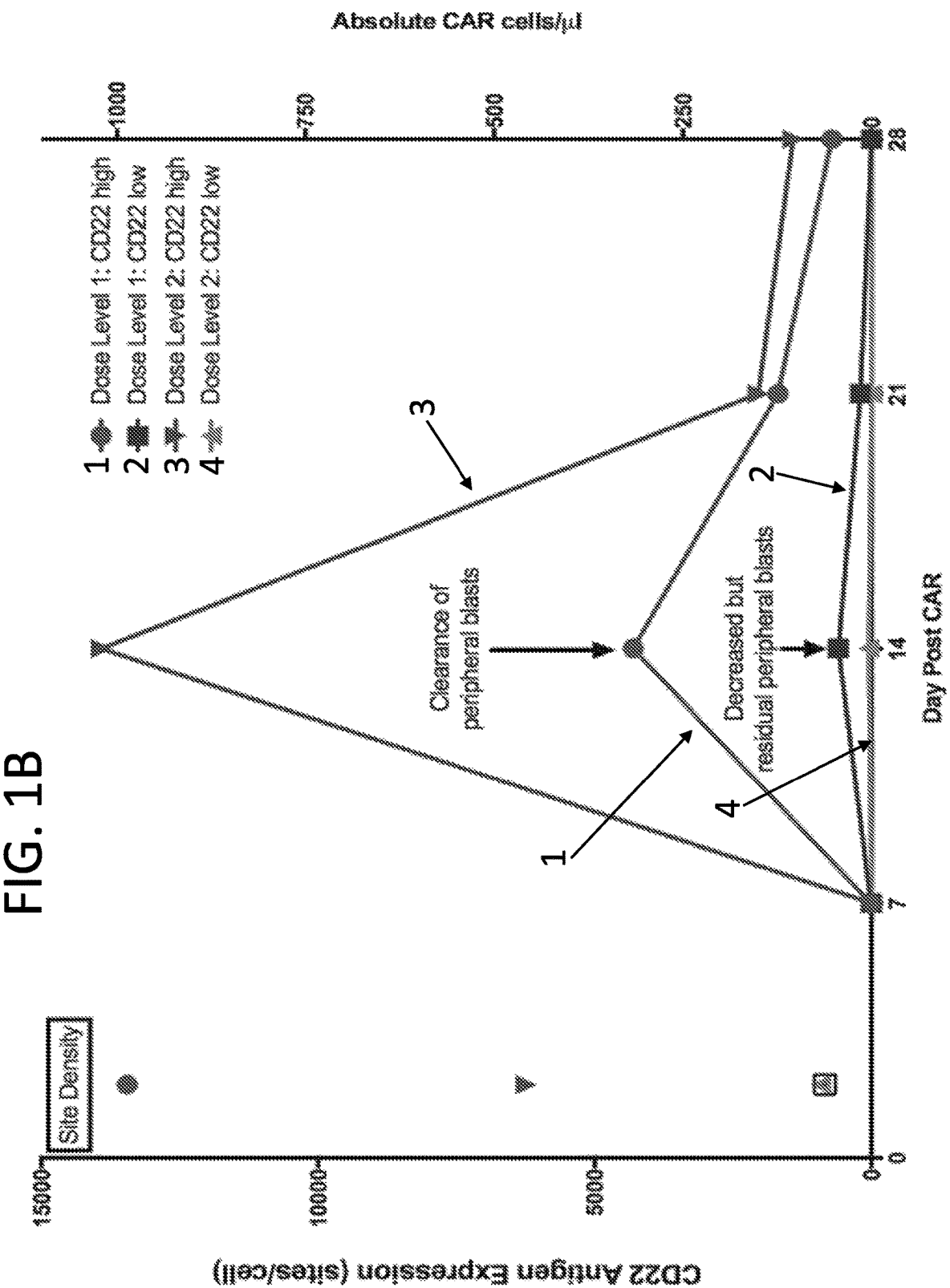

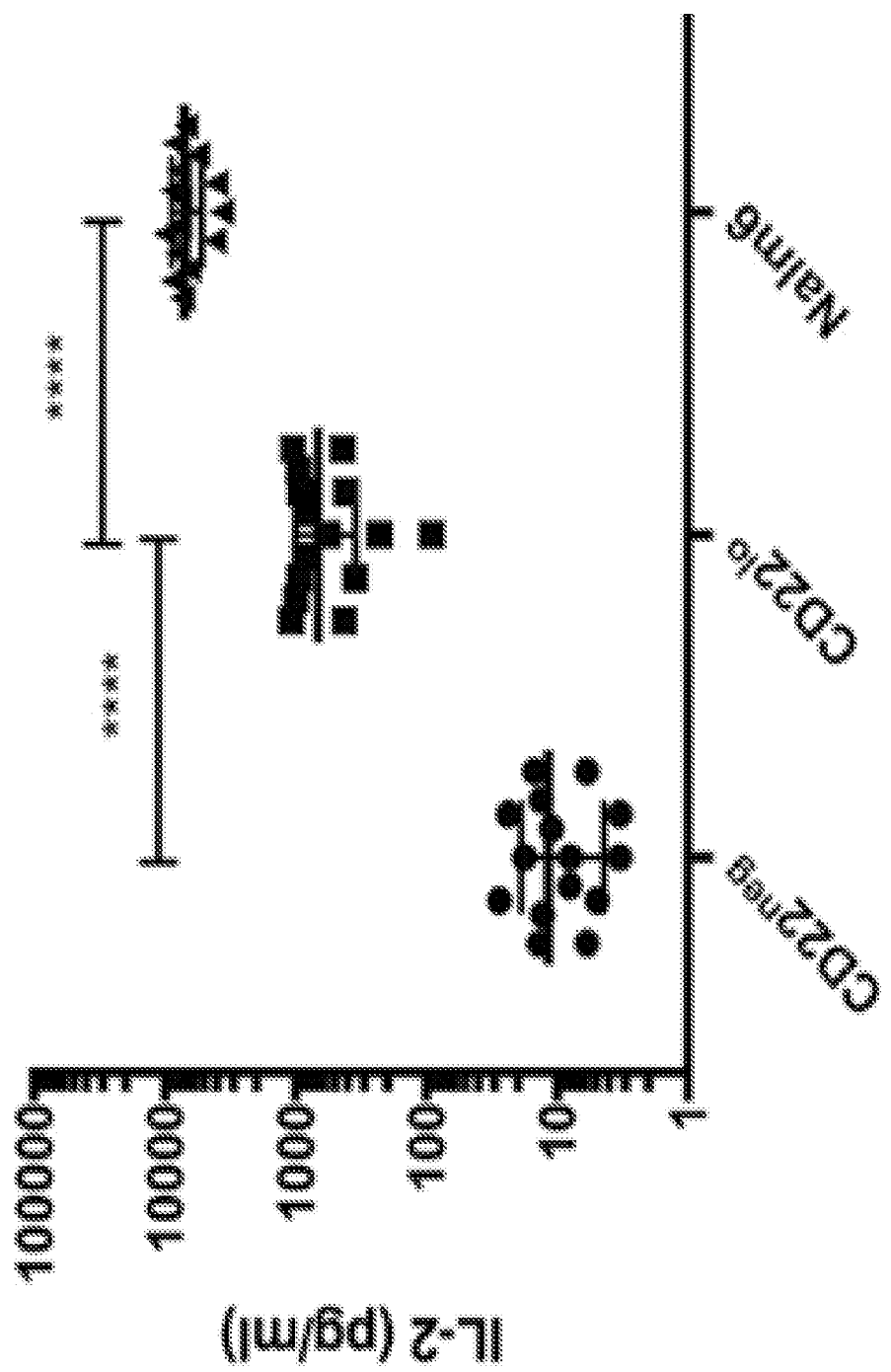

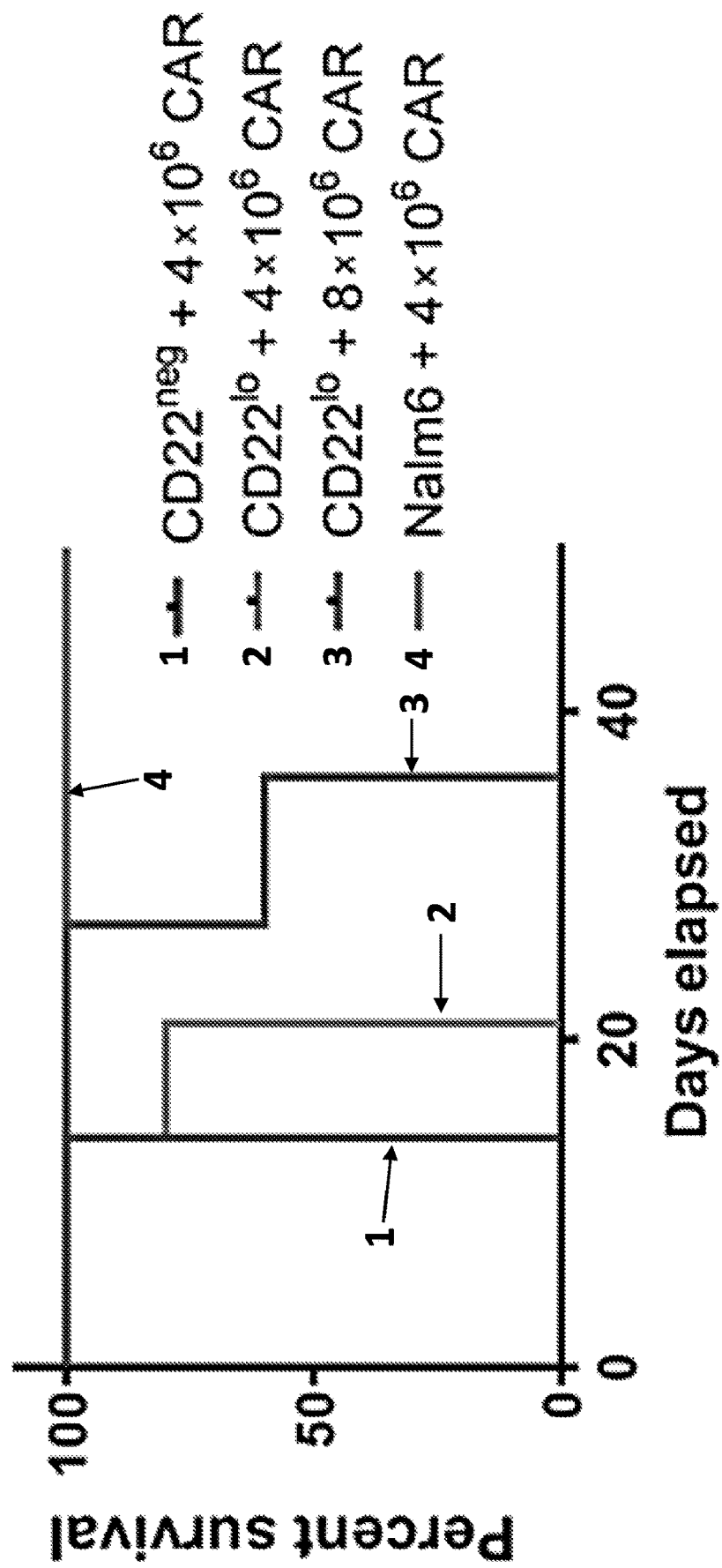

FIG. 2D
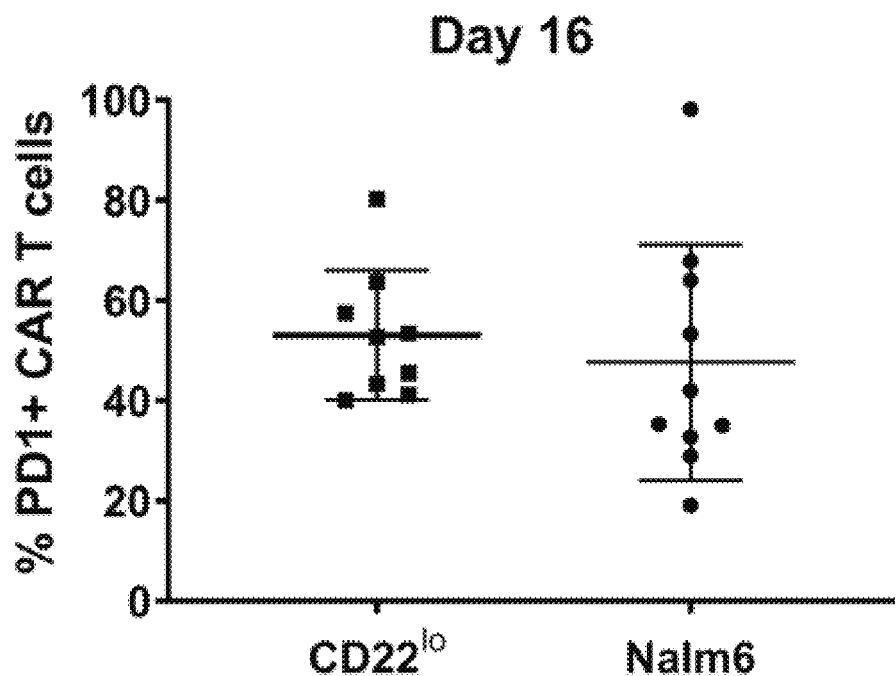
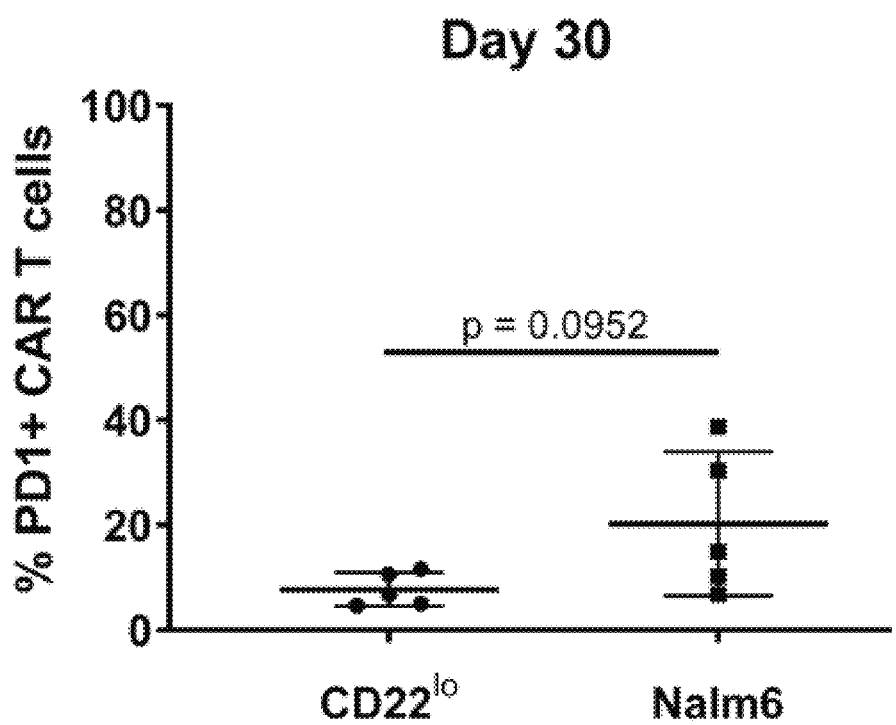

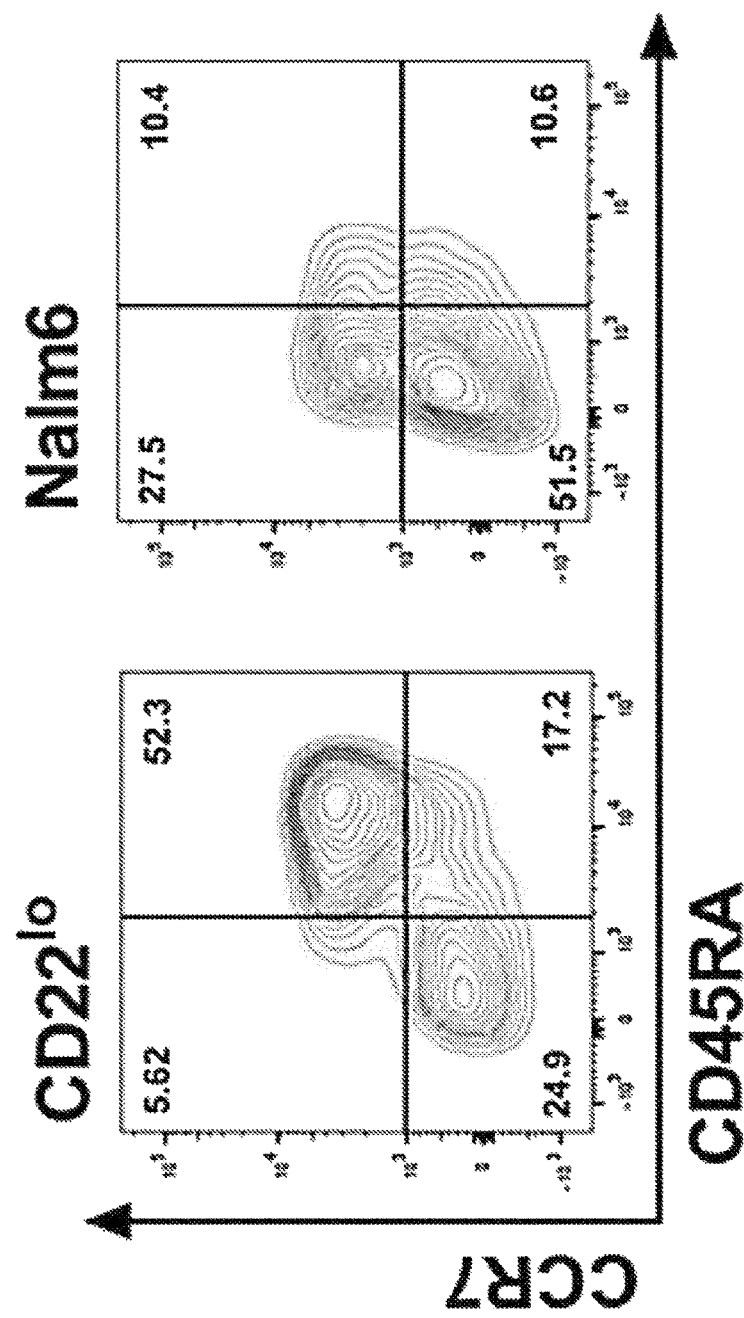

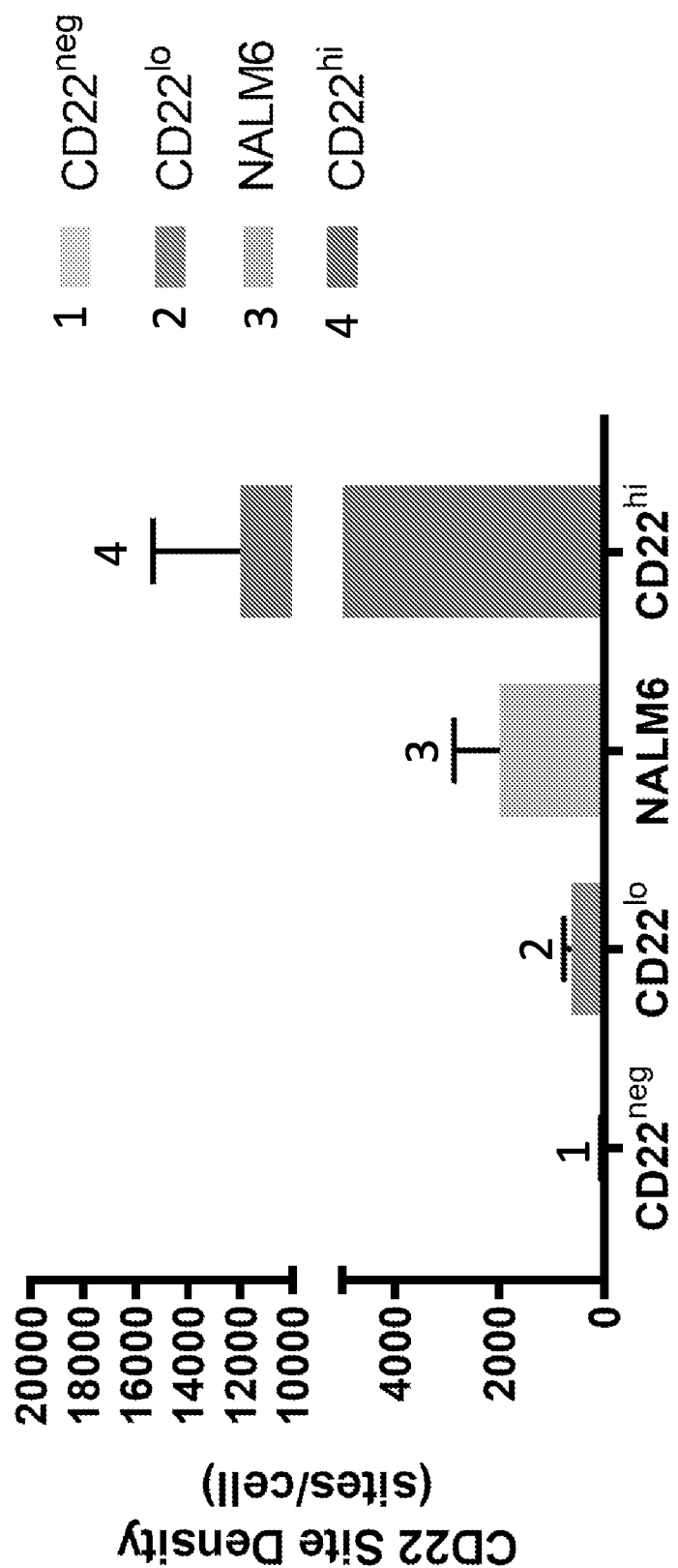

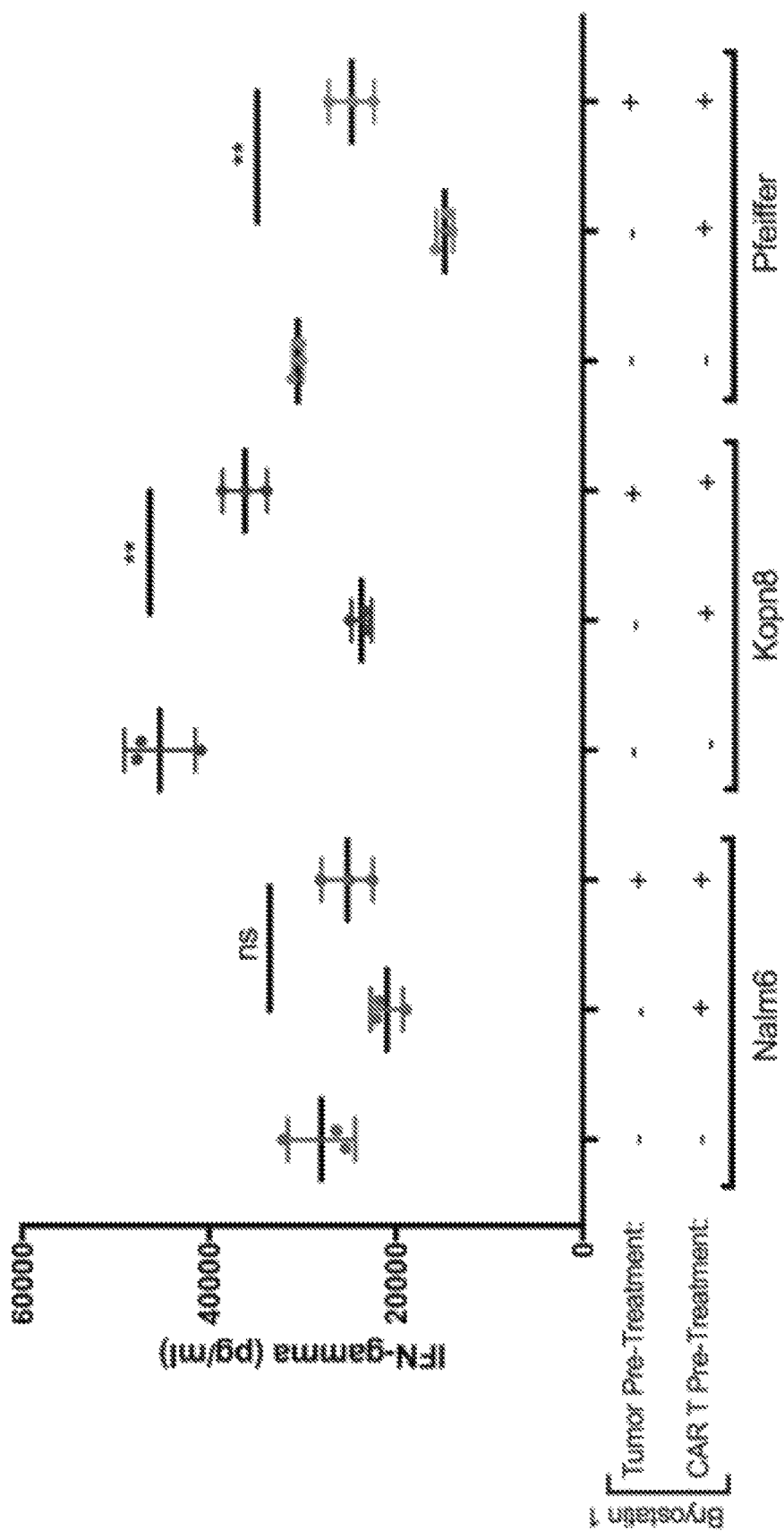

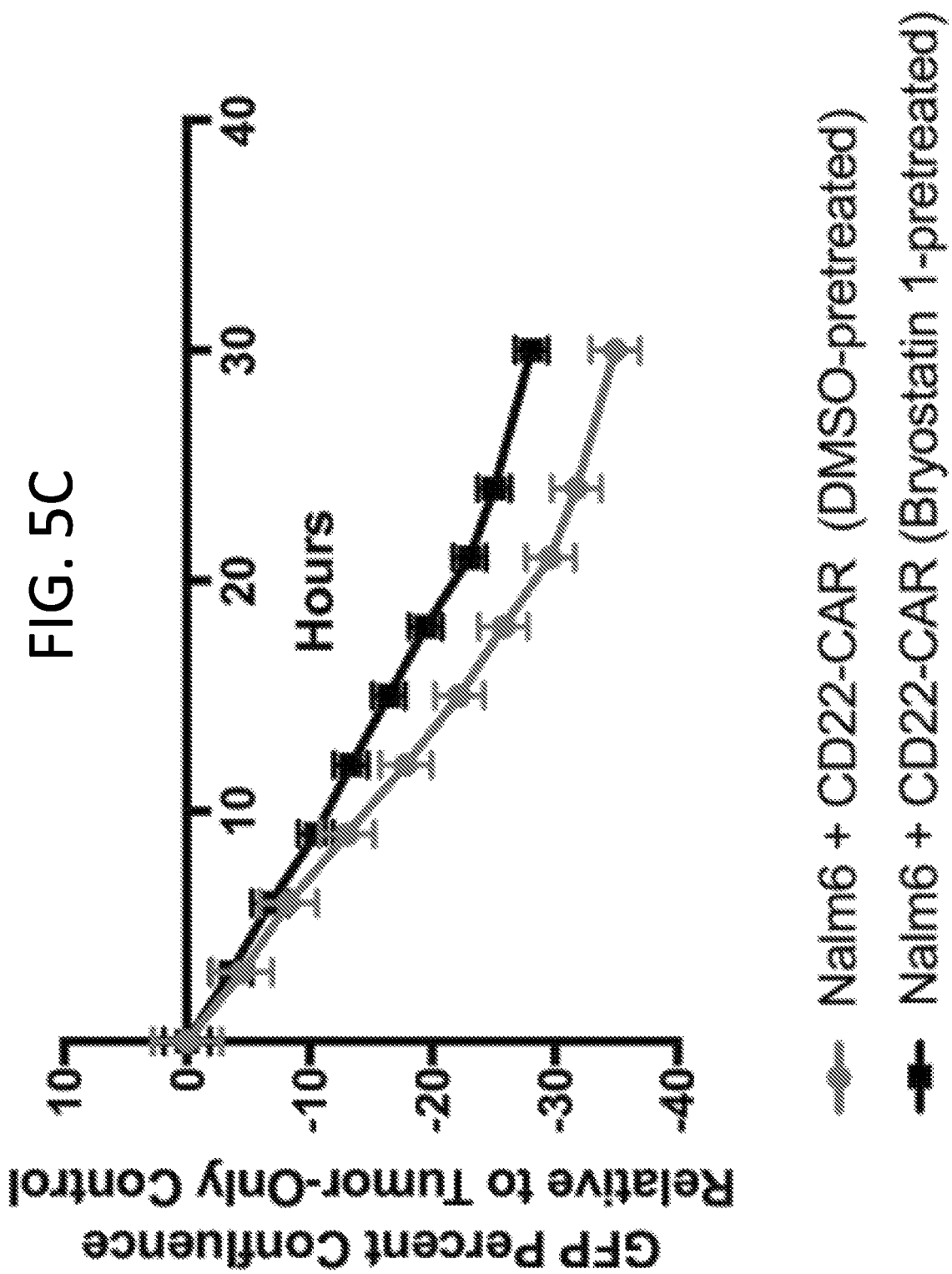

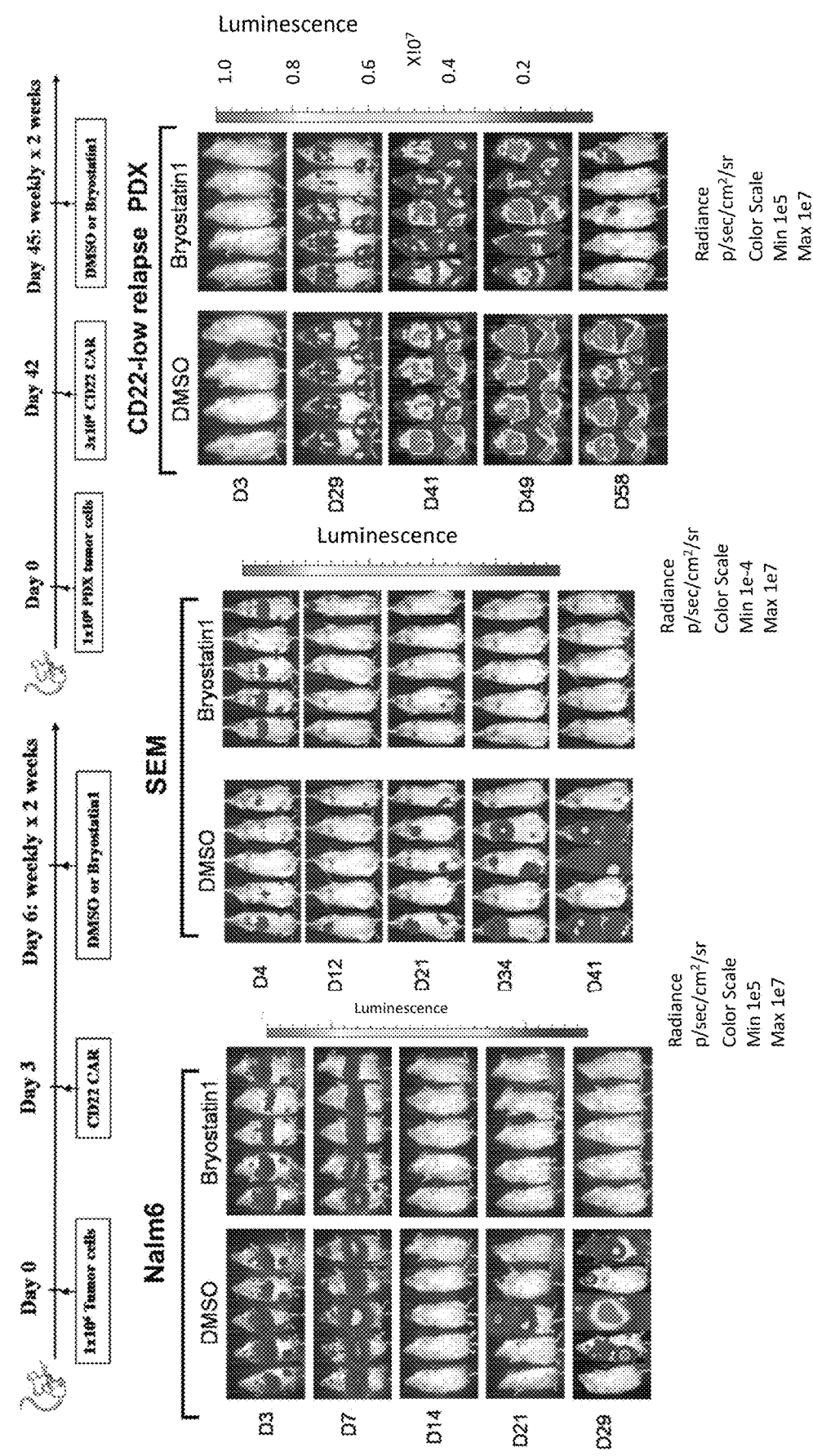

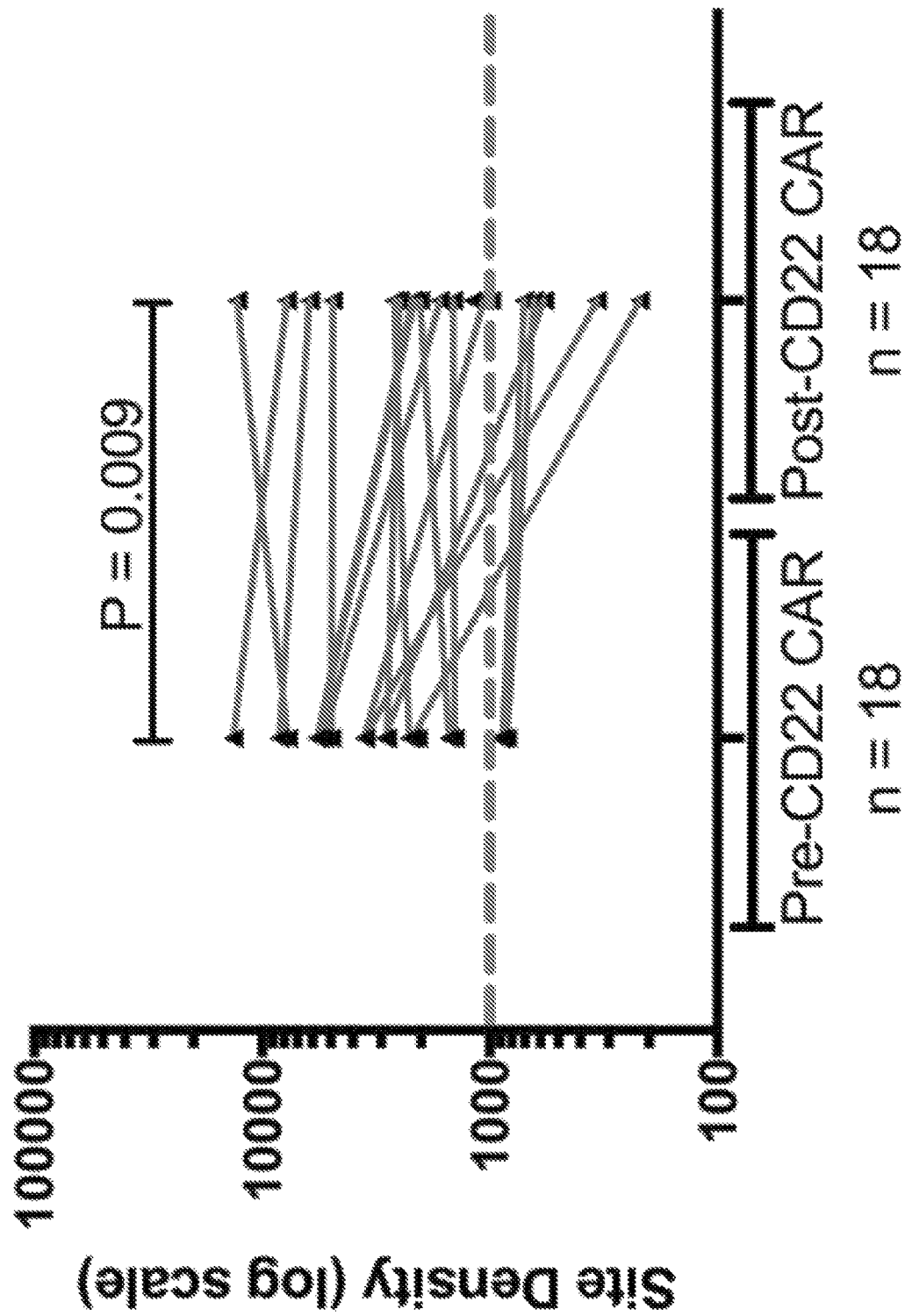

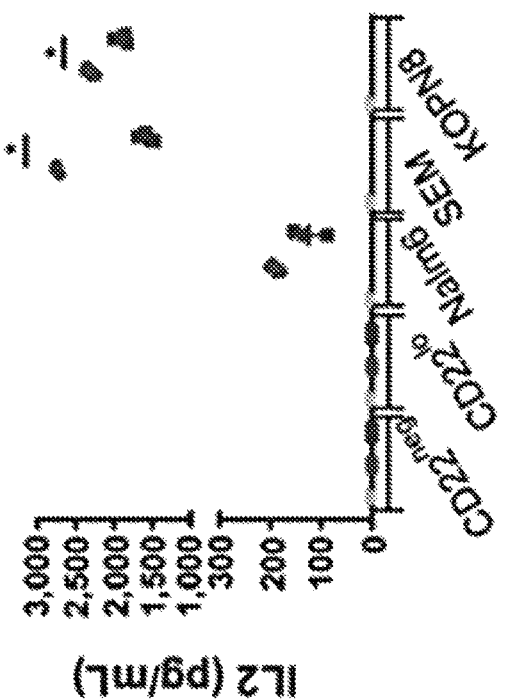
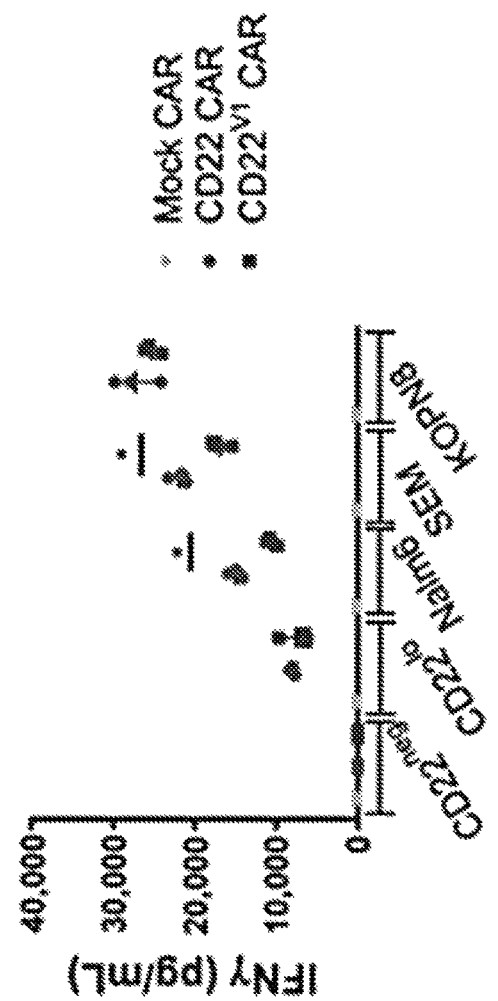
FIG. 9A

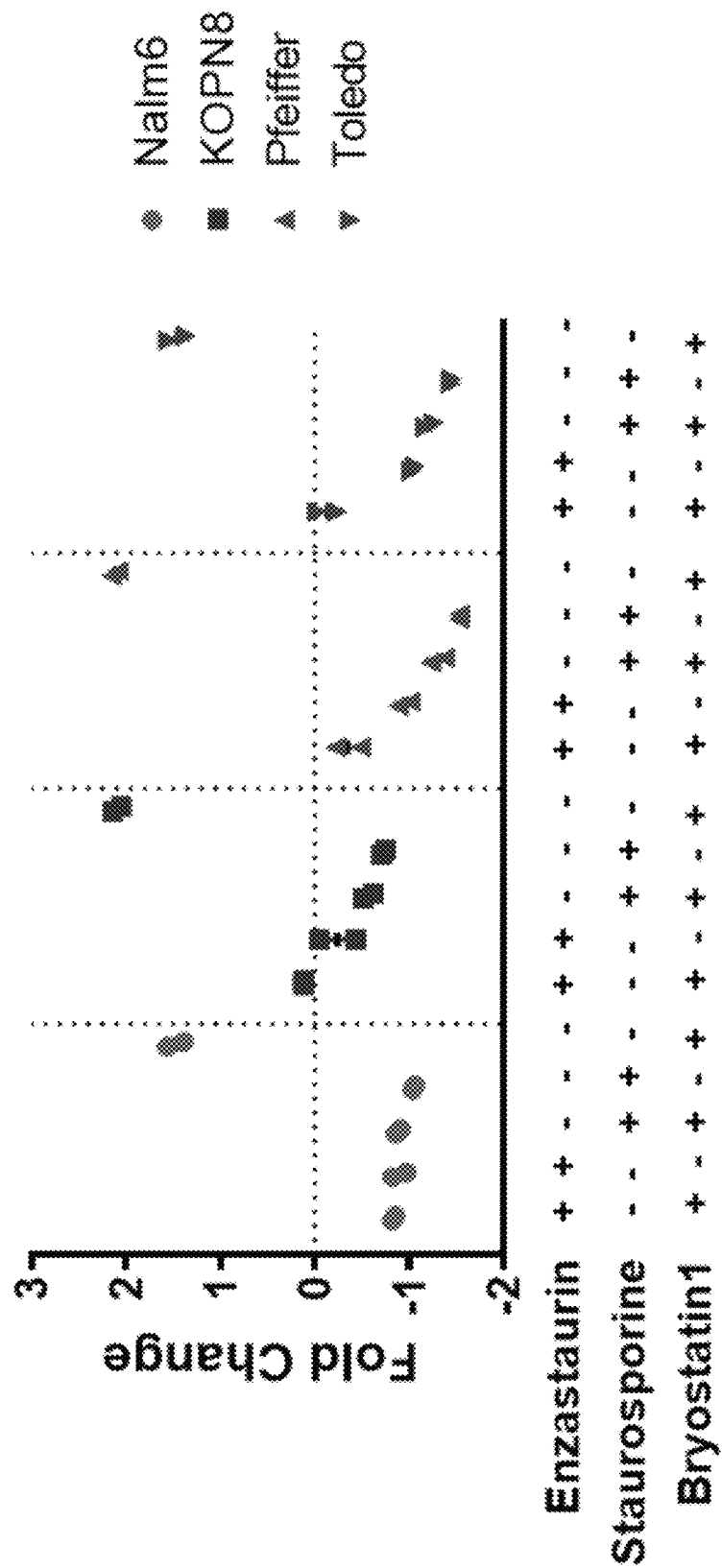

FIG. 12

```
m971     QVQLQQSGPGLVKPSQTLSLTCAISGDSVSSNSAAWNWIRQSPSRGLEWLGRTYYRSK
m971-L7  QVQLQQSGPGMVKPSQTLSLTCAISGDSVSSNSVAWNWIRQSPSRGLEWLGRTYYRST
         ************:*******************.*.************************.

m971     WYNDYAVSVKSRITINPDTSKNQFSLQLNSVTPEDTAVYYCAREVTGDLEDAFDIWGQ
m971-L7  WYNDYAVSMKSRITINPDTNKMQFSLQLNSVTPEDTAVYYCAREVTGDLEDAFDIWGQ
         ******:********.*:*********************************** m971     GTMVTVSSGGGGSGGGGSGGGGSDIQMTQSPSSLSASVGDRVTITCRASQTIWSYL
m971-L7  GTMVTVSSGGGGSGGGGSGGGGSDIQMIQSPSSLSASVGDRVTITCRASQTIWSYL
         *************************.************************** m971     NWYQQRPGKAPNLLIYAASSLQSGVPSRFSGRGSGTDFTLTISSLQAEDFATYYCQQSYS
m971-L7  NWYRQRPGEAPNLLIYAASSLQSGVPSRFSGRGSGTDFTLTISSLQAEDFATYYCQQSYS
         *:*:**************************************************** m971     IPQTFGQGTKLEIK  (SEQ ID NO: 3)
m971-L7  IPQTFGQGTKLEIK  (SEQ ID NO: 6)
         **************
```

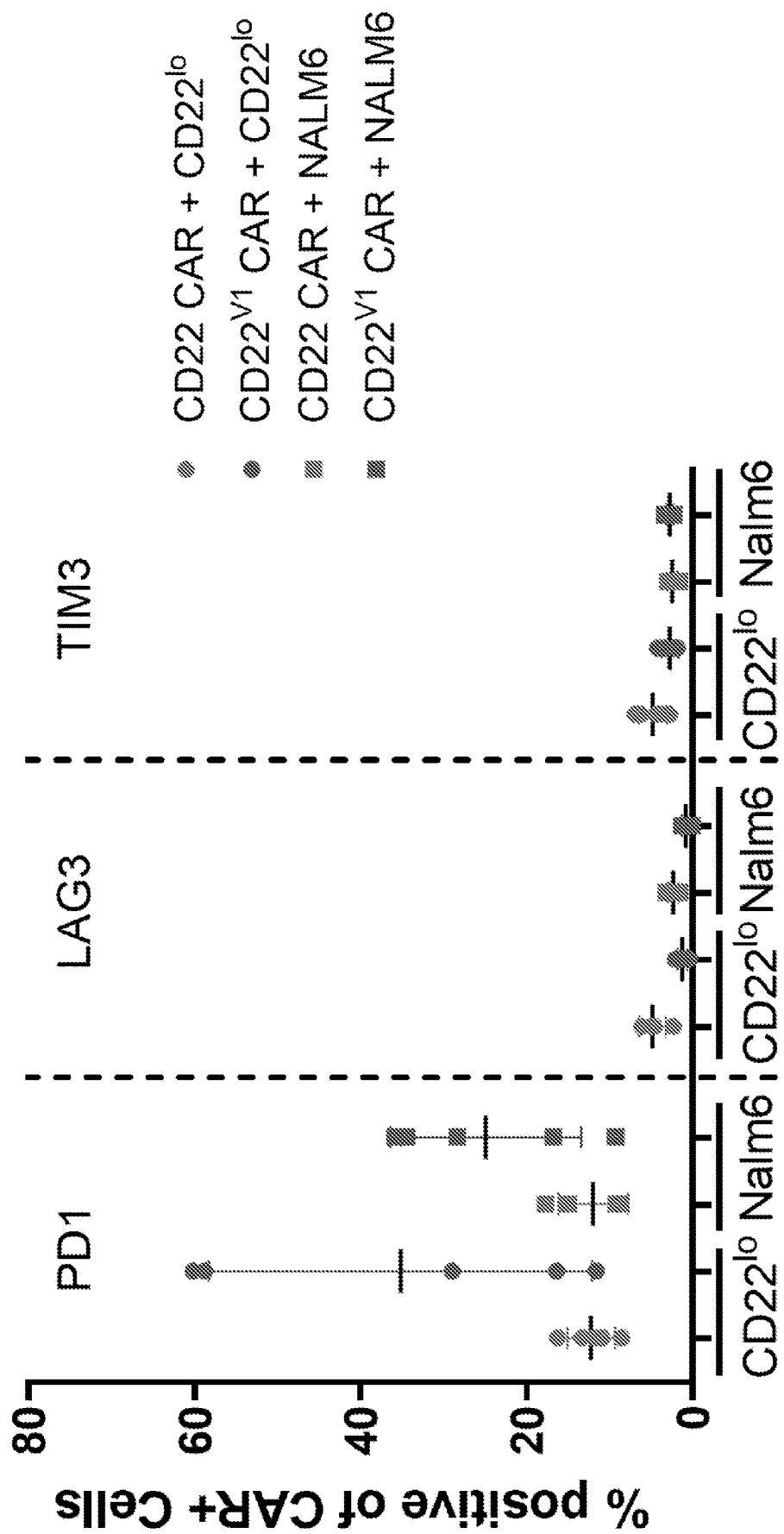

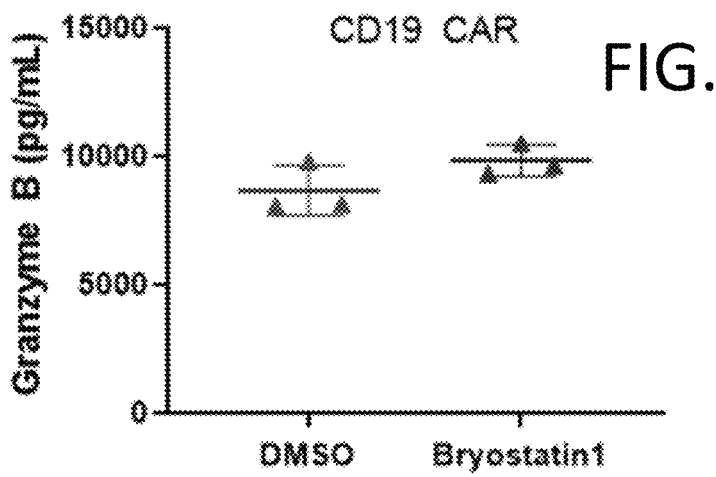
FIG. 14A
FIG. 14B
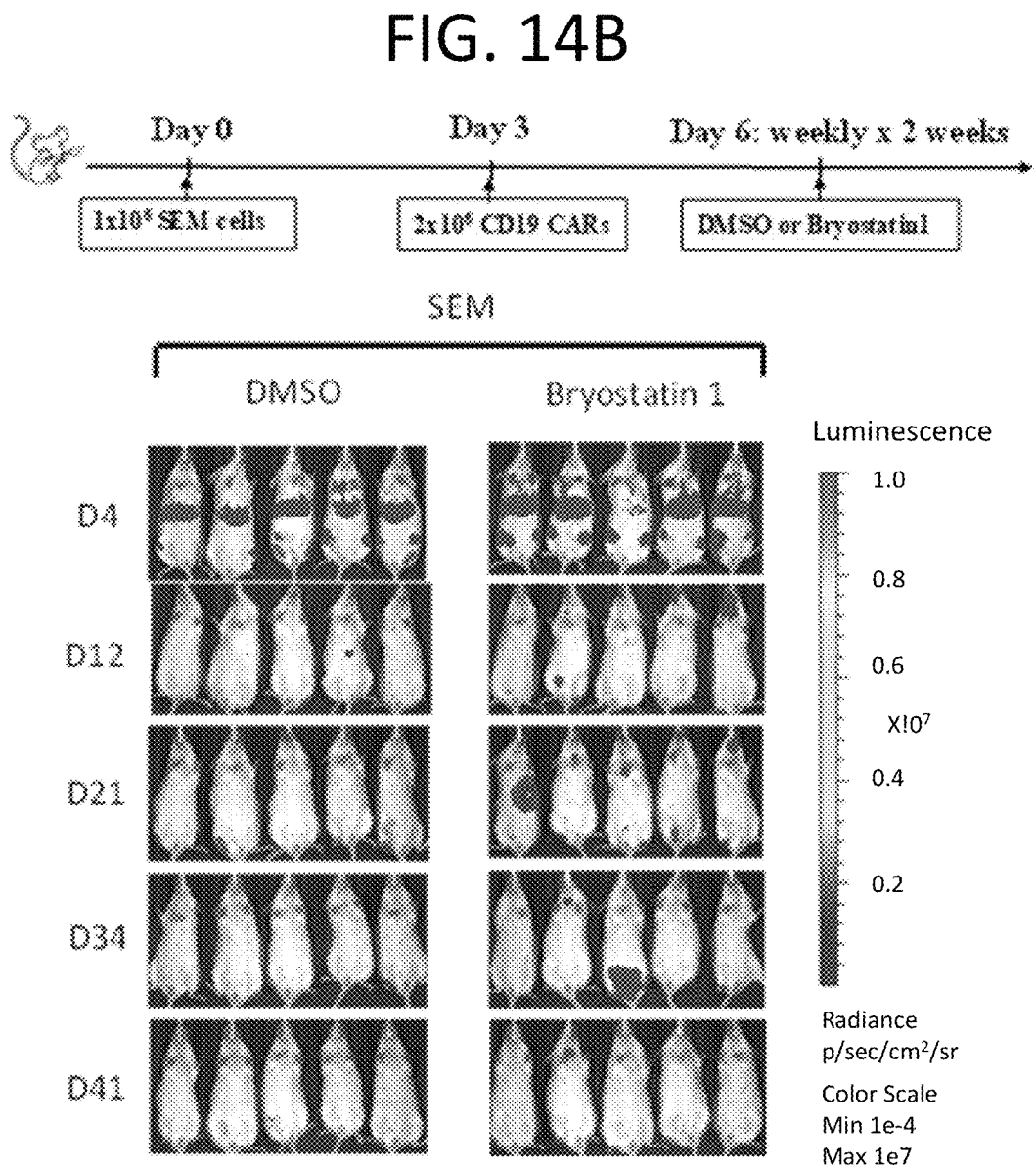

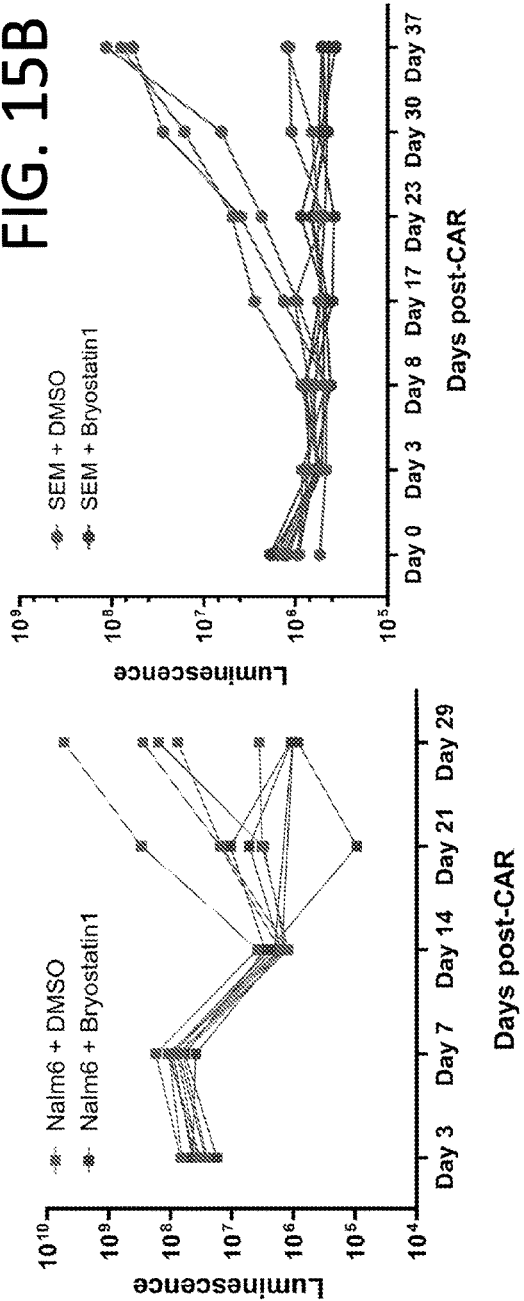
FIG. 15A
FIG. 15B
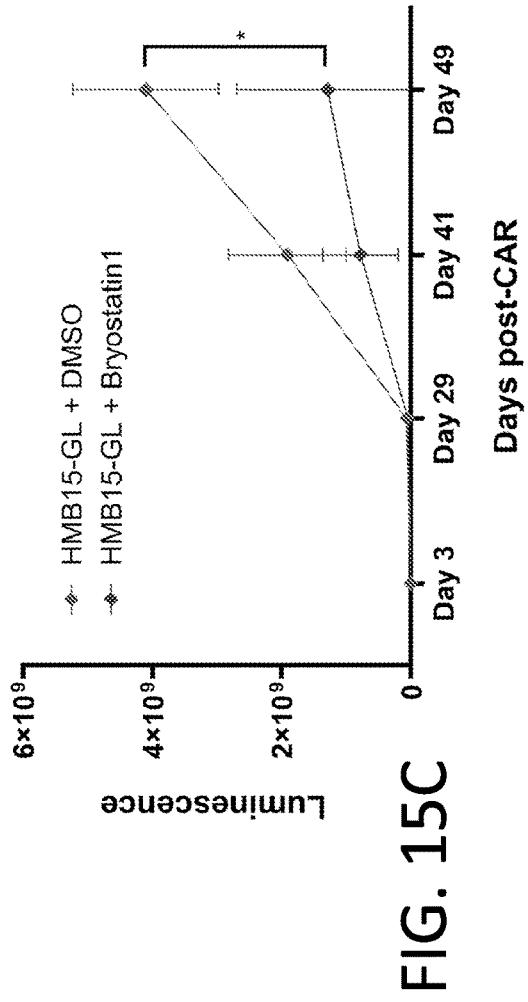
FIG. 15C

```
                        SEQUENCE LISTING

<160> NUMBER OF SEQ ID NOS: 10

<210> SEQ ID NO 1
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30
```

Leu Asn Trp Tyr Gln Gln Arg Pro Gly Lys Ala Pro Asn Leu Leu Ile
            35                  40                  45

Tyr Ala Ala Ser Ser Leu Gln Ser Gly Val Pro Ser Arg Phe Ser Gly
        50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105

<210> SEQ ID NO 3
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Thr Ile Trp Ser Tyr Leu Asn Trp Tyr Gln
                165                 170                 175

Gln Arg Pro Gly Lys Ala Pro Asn Leu Leu Ile Tyr Ala Ala Ser Ser
            180                 185                 190

Leu Gln Ser Gly Val Pro Ser Arg Phe Ser Gly Arg Gly Ser Gly Thr
        195                 200                 205

Asp Phe Thr Leu Thr Ile Ser Ser Leu Gln Ala Glu Asp Phe Ala Thr
    210                 215                 220

Tyr Tyr Cys Gln Gln Ser Tyr Ser Ile Pro Gln Thr Phe Gly Gln Gly
225                 230                 235                 240

Thr Lys Leu Glu Ile Lys
                245

<210> SEQ ID NO 4
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 4

Gln Val Gln Leu Gln Gln Ser Gly Pro Gly Met Val Lys Pro Ser Gln
1               5                   10                  15

Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Thr Trp Tyr Asn Asp Tyr Ala
    50                  55                  60

Val Ser Met Lys Ser Arg Ile Thr Ile Asn Pro Asp Thr Asn Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 5

Asp Ile Gln Met Ile Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Arg Gln Arg Pro Gly Glu Ala Pro Asn Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105

<210> SEQ ID NO 6
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Gln Gln Ser Gly Pro Gly Met Val Lys Pro Ser Gln
1               5                   10                  15

Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

```
Trp Leu Gly Arg Thr Tyr Tyr Arg Ser Thr Trp Tyr Asn Asp Tyr Ala
    50                  55                  60

Val Ser Met Lys Ser Arg Ile Thr Ile Asn Pro Asp Thr Asn Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
            115                 120                 125

Ser Gly Gly Gly Gly Ser Gly Gly Gly Gly Ser Asp Ile Gln Met Ile
130                 135                 140

Gln Ser Pro Ser Ser Leu Ser Ala Ser Val Gly Asp Arg Val Thr Ile
145                 150                 155                 160

Thr Cys Arg Ala Ser Gln Thr Ile Trp Ser Tyr Leu Asn Trp Tyr Arg
            165                 170                 175

Gln Arg Pro Gly Glu Ala Pro Asn Leu Leu Ile Tyr Ala Ala Ser Ser
            180                 185                 190

Leu Gln Ser Gly Val Pro Ser Arg Phe Ser Gly Arg Gly Ser Gly Thr
            195                 200                 205

Asp Phe Thr Leu Thr Ile Ser Ser Leu Gln Ala Glu Asp Phe Ala Thr
            210                 215                 220

Tyr Tyr Cys Gln Gln Ser Tyr Ser Ile Pro Gln Thr Phe Gly Gln Gly
225                 230                 235                 240

Thr Lys Leu Glu Ile Lys
            245

<210> SEQ ID NO 7
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 7
tctccctctc ctgggtg                                                    17

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ctctccctcc cagatctcag                                                 20

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 9
aggagggaag gggtactg                                                   18

<210> SEQ ID NO 10
<211> LENGTH: 22
<212> TYPE: DNA
```

```
<213> ORGANISM: Artificial Sequence
<220> FEATURE:
<223> OTHER INFORMATION: Synthetic oligonucleotide

<400> SEQUENCE: 10
agccaacgtt ttggatcttc ag                                              22
```

AFFINITY MATURED CD22-SPECIFIC MONOCLONAL ANTIBODY AND USES THEREOF

CROSS REFERENCE TO RELATED APPLICATIONS

This application is the U.S. National Stage of International Application No. PCT/US2019/041401, filed Jul. 11, 2019, published in English under PCT Article 21(2), which claims the benefit of U.S. Provisional Application No. 62/697,185, filed Jul. 12, 2018, which is herein incorporated by reference in its entirety.

ACKNOWLEDGMENT OF GOVERNMENT SUPPORT

This invention was made with government support under project number ZIA BC 010701 awarded by the National Institutes of Health. The government has certain rights in the invention.

FIELD

This disclosure concerns affinity maturation of a monoclonal antibody specific for CD22 and its use, such as for cancer therapy.

BACKGROUND

While overall survival for pediatric B-cell acute lymphoblastic leukemia (ALL) treated with risk-adapted, multi-agent chemotherapeutic regimens is greater than 85% at 5 years, patients who relapse lack good therapeutic options (Pui et al., *J Clin Oncol.* 2015; 33(27): 2938-2948; Smith et al., *Cancer.* 2014; 120(16): 2497-2506). Chimeric antigen receptor (CAR) T cell therapy targeting CD19 can induce remissions in a high percentage of patients and is potentially curative for some (Davila et al., *Sci Transl Med.* 2014; 6(224): 224ra25; Maude et al., *N Engl J Med.* 2014; 371 (16):1507-1517; Lee et al., *Lancet.* 2015; 385(9967): 517-528). However, longer follow-up data has shown that a portion of the patients achieving remission will subsequently relapse with either poor CAR persistence or loss of the targeted CD19 epitope (Lee et al., *Lancet.* 2015; 385(9967): 517-528; Grupp et al., *N Engl J Med.* 2013; 368(16): 1509-1518; Maude et al., *Blood.* 2015; 125(26): 4017-4023; Gardner et al., *Blood.* 2016; 127(20): 2406-2410). Treatment with a CAR targeting CD22 (Haso et al., *Blood.* 2013; 121(7): 1165-1174), an alternative, clinically validated ALL antigen (Yilmaz et al., *Ther Adv Hematol.* 2015; 6(5): 253-261), led to a 70% remission induction rate at biologically active doses, including activity in patients relapsing with CD19 CAR resistant ALL (Fry et al., *Nat Med.* 2018; 24(1): 20-28). Similar to CD19 CART, a substantial fraction of patients achieving remission after CD22 CART relapse due to poor CAR persistence or, more frequently, altered target antigen expression. In contrast to relapse following CD19 CART or blinatumomab treatment, where complete loss of antigen expression is observed, relapse after CD22 CART is more likely to occur with diminished CD22 on the cell surface of the leukemia (Fry et al., *Nat Med.* 2018; 24(1): 20-28).

The thresholds of antigen expression required to activate a CAR have been identified in preclinical models (Walker et al., *Mol Ther.* 2017; 25(9): 2189-2201; Chmielewski et al., *Gene Ther.* 2011; 18(1): 62-72; Yoshida et al., *Clin Transl Immunology.* 2016; 5(12): e116; Watanabe et al., *J Immunol.* 2015; 194(3): 911-920). At lower target antigen site densities, CAR T cells are less functional and produce fewer cytokines, such as IFN-γ or IL-2, despite augmentation with co-stimulatory molecules or alterations of CAR T cell affinity binding (Chmielewski et al., *Gene Ther.* 2011; 18(1): 62-72). This threshold for activation is relatively high compared to that required for activation through the T cell receptor (TCR). However, the functional ramifications of this site density limitation have not been fully explored.

SUMMARY

The development of an affinity matured monoclonal antibody specific for the B cell antigen CD22 is described. The affinity matured antibody, referred to as m971-L7, exhibits a significantly improved CD22 binding affinity compared to parental antibody m971 (from about 2 nM to less than 50 pM).

Provided herein are monoclonal antibodies, or antigen-binding fragments thereof, that bind, such as specifically bind, CD22. In some embodiments, the monoclonal antibodies or antigen-binding fragments include the VH domain and VL domain complementarity determining region (CDR) sequences of m971-L7. Also provided herein are conjugates that include a disclosed monoclonal antibody, or antigen-binding fragment thereof. In some examples, provided are chimeric antigen receptors (CARs), immunoconjugates, multi-specific antibodies, antibody-drug conjugates (ADCs), antibody-nanoparticle conjugates and fusion proteins that include a monoclonal antibody or antigen-binding fragment disclosed herein. Compositions that include a CD22-specific monoclonal antibody or antigen-binding fragment and a pharmaceutically acceptable carrier are also provided by the present disclosure.

Also provided herein are nucleic acid molecules and vectors encoding the CD22-specific monoclonal antibodies, CARs, immunoconjugates, multi-specific antibodies and fusion proteins disclosed herein.

Further provided are methods of detecting expression of CD22 in a sample using the disclosed antibodies and antigen-binding fragments.

Also provided are methods of treating a B cell malignancy in a subject by administering to the subject a CD22-specific monoclonal antibody, antigen-binding fragment, CAR, isolated cell expressing a CAR, immunoconjugate, ADC, multi-specific antibody, antibody-nanoparticle conjugate, fusion protein or composition disclosed herein. Such methods can further include administration of an agent that upregulates CD22 expression (such as Byrostatin1).

Methods of diagnosing a subject as having a B cell malignancy, or confirming a diagnosis of a B-cell malignancy in a subject, by contacting a sample obtained from the subject with a disclosed CD22-specific monoclonal antibody or fragment thereof are further provided.

Also provided are kits that include (1) CD22-specific monoclonal antibody, antigen-binding fragment, CAR, isolated cell expressing a CAR, immunoconjugate, ADC, multi-specific antibody, antibody-nanoparticle conjugate, fusion protein or composition disclosed herein, (2) an agent that upregulates CD22 expression (such as Byrostatin1), and (3) optionally an anti-cancer agent.

The foregoing and other objects, features, and advantages of the invention will become more apparent from the following detailed description, which proceeds with reference to the accompanying figures.

BRIEF DESCRIPTION OF THE DRAWINGS

FIGS. 1A-1F: (FIG. 1A) Clinical samples from pre-B cell ALL patients were evaluated for CD19 and CD22 expression using Quantibrite-PE bead evaluation. Samples were obtained prior to treatment with either CD19 or CD22 CART. Statistical analysis was performed using an unpaired t-test. (FIG. 1B) Samples from patients treated with CD22 CART were evaluated for CD22 site density using Quantibrite analysis and for CD22 CAR expression by flow cytometry. (FIG. 1C) Patient CAR T cells were co-incubated with varying site density cell lines for 18 hours. Supernatant was evaluated for IL-2, IFN-γ and granzyme B using multiplex ELISA assay at varying dilutions. Statistical analysis was performed using an unpaired t-test. (FIG. 1D) Nalm6 ALL tumor cells ($1\times10^5$) expressing varying amounts of CD22 were co-cultured with $1\times10^5$ CD22 CAR T cells from CD22 CART patient samples for 18 hours. Supernatant was evaluated using the Meso Scale Multiplex pro-inflammatory cytokine panel. (FIG. 1E) Kaplan-Meier curves comparing $CD22^{neg}$ with $CD22^{lo}$ and Nalm6 leukemia-bearing mice with different CART doses. (FIG. 1F) Peripheral blood was collected from mice at interval timepoints and assessed for CAR expansion using flow cytometry and analyzed on Fortessa flow machine. Statistical significance was calculated using an unpaired t-test (** $p<0.0001$, * $p<0.0002$, ** $p<0.0021$).

FIGS. 2A-2G: (FIG. 2A) Mock or CD22 CAR T cells were co-incubated at a 1:1 effector-to-target ratio with either $CD22^{neg}$, $CD22^{lo}$ or Nalm6 cells. Cell death was monitored by loss of GFP-positive cells using Incucyte analysis. (FIG. 2B) NSG mice were injected with $1\times10^6$ GPF-positive CD22neg, CD22lo, or Nalm6 tumor cells on Day 0. On Day 3, $5\times10^6$ CD22 CAR T cells were injected. Mice were imaged using IVIS technology after luciferin-D IP injection. (FIGS. 2C-2E) Cells were extracted from CD22 CAR treated CD22lo or Nalm6 NSG mice 16 days (FIGS. 2C, 2D left panel, and 2E) or 30 days (FIG. 2D, right panel) after tumor injection. Cells were stained for flow cytometry and analyzed on a Fortessa flow machine. (FIG. 2E) Site density cell lines were co-incubated with CD22 CART for 24 hours, and PD1 expression was stained for flow cytometry and analyzed on Fortessa flow machine. MFI=mean fluorescence intensity. (FIG. 2F) CD22 CAR was co-cultured in vitro with $CD22^{lo}$ or Nalm6 leukemia for 8 days and cells were evaluated using flow cytometry and analyzed on Fortessa flow machine. (FIG. 2G) CD22 site density was evaluated using flow cytometry and Quantibrite analysis for CRISPR-edited Nalm6 cell lines.

(FIG. 3A) Four cell lines (Nalm6, Kopn8, Pfieffer and Toldeo) were co-incubated with 1 ng/ml Bryostatin 1 for 24 hours and analyzed using flow cytometry one day after Bryostatin 1 exposure. Site density was analyzed using standardized Quantibrite-PE beads. (FIG. 3B) Cell lines were co-incubated with 1 ng/ml Bryostatin 1 for 24 hours, washed, and analyzed using flow cytometry at 1 and 7 days after Bryostatin 1 exposure. Fold change was calculated based on site density: (Cell line Bryostatin 1—Cell line DMSO)/Cell line DMSO. (FIG. 3C) NSG mice were injected with $1\times10^6$ GPF-positive Nalm6 leukemia cells on Day 0. Bryostatin 1 was administered at 0.8 μg/kg on Day 3. Mice were sacrificed 7 and 12 days after Bryostatin 1 injection and CD22 was evaluated by flow cytometry. (FIG. 3D) CD22-low relapse PDX cell line was cultured in vitro with 1 nmol/L Bryostatin 1 for 24 hours and measured for CD22 expression using CD22 antibody.

(FIGS. 4A-4B) KOPN8 or SEM cell lines were exposed to Bryostatin 1 for 16, 24, 48, or 72 hours. RNA was extracted from cells and analyzed using RNAseq. (FIGS. 4C-4E) Cell lines were co-incubated with 1 ng/ml of Bryostatin 1 for 24 hours. Then $1\times10^5$ target tumor cells were co-cultured with $1\times10^5$ CD22 CAR for 16 hours. IL-2 (FIG. 4C), IFN-γ (FIG. 4D), and granzyme B (FIG. 4E) were measured by ELISA from cell culture supernatants. Statistical significance was calculated using an unpaired t-test (** $p<0.0001$, * $p<0.0002$, ** $p<0.0021$, * $p<0.0332$).

FIGS. 5A-5D: (FIGS. 5A-5B) CD22 CART cells were co-incubated with 1 ng/ml of Bryostatin 1 for 24 hours and washed. Then $1\times10^5$ target tumor cells were co-cultured with $1\times10^5$ $^{CD}22$ CAR for 18 hours. IFN-γ (FIG. 5A) and granzyme B (FIG. 5B) were measured by ELISA from cell culture supernatants. Statistical analysis was performed using an unpaired t-test (** $p<0.0001$, * $p<0.0002$, ** $p<0.0021$, * $p<0.0332$). (FIG. 5C) Mock or CD22 CAR T cells were co-incubated at an effector-to-target ratio of 1:1 with either CD22neg, CD22lo or Nalm6 cells. Cell death was monitored by loss of GFP-positive cells using Incucyte analysis. (FIG. 5D) NSG mice were injected with Nalm6 on Day 0, CD22 CART cells on Day 3, and then were given either DMSO control or Bryostatin 1 at 0.8 μg/kg once weekly for 2 weeks. Leukemia progression was monitored using IVIS technology and luciferin-D IP injections.

FIGS. 6A-6D: Bryostatin 1 treatment pre-CAR infusion alters T-cell phenotype without T-cell exhaustion, and post-CAR infusion improves durability of remission in vivo. (FIG. 6A) Nalm6 cells were exposed to 1 nmol/L Bryostatin 1 for 24 hours, then injected into mice on day 0. CD22 CAR T cells were administered on day 3, and mice were sacrificed on day 10. Bone marrow cells were stained for flow cytometry and analyzed on Fortessa flow machine. Statistics were calculated using unpaired t test (*, $P<0.0332$). (FIG. 6B) NSG mice were injected with Nalm6 on day 0, CD22 CART on day 3, and then were given either DMSO control or Bryostatin 1 at 40 μg/kg once weekly for 2 weeks. Mice were sacrificed 30 days after tumor injection. Cells were stained for flow cytometry and analyzed on Fortessa flow machine. (FIG. 6C) NSG mice were injected with $1\times10^6$ GPF-positive Nalm6 or SEM tumor cells on day 0. On day 3, either $3\times10^6$ (Nalm6) or $2\times10^6$ (SEM) mock or CD22 CAR were injected for treatment. Mice were given 40 μg/kg of Bryostatin 1 or DMSO once weekly for 2 weeks. Mice were imaged using IVIS technology and luciferin-D intraperitoneal injections. (FIG. 6D) NSG mice were injected with $1\times10^6$ GPF-positive PDX tumor cells on day 0. On day 42, $3\times10^6$ Mock or CD22 CAR were injected for treatment. Mice were given 40 μg/kg of Bryostatin 1 or DMSO once weekly for 2 weeks starting on day 45. Mice were imaged using IVIS technology and luciferin-D intraperitoneal injections.

FIGS. 7A-7B: (FIG. 7A) Site density cell lines (Nalm6, CD22neg, CD22lo and CD22hi) were co-incubated with CD22 CART cells. IL-2 in the culture supernatant was measured using ELISA. (FIG. 7B) Patient samples pre- and post-CD22 CAR T cell therapy were evaluated for CD22 expression using Quantibrite-PE bead evaluation. Statistical analysis was performed using the Wilcox test.

FIGS. 9A-9F: (FIGS. 9A-9B) A total of $1\times10^5$ tumor cells were co-cultured with $1\times10^5$ mock, CD22, or $CD22^{11}$ CAR and assessed for IFNγ and IL2 cytokines by ELISA from cell culture supernatants (statistics were calculated using paired t test (*, P<0.0332); FIG. 9A) or Annexin V staining was assessed over time using IncuCyte ZOOM (FIG. 9B). These data are representative of two separate experiments and were consistent across two different effector-to-target ratios. (FIG. 9C) NSG mice were injected with $1\times10^6$ GPF-positive $CD22^{neg}$, $CD22^{lo}$, or Nalm6 tumor cells on day 0. On day 3, $5\times10^6$ CD22 or $CD22^{V1}$ CAR were injected for treatment. Mice were imaged using IVIS technology and luciferin-D intraperitoneal injections. Luminescence quantification is shown on the right. These data are representative of two separate experiments. (FIG. 9D) CD22 or $CD22^{V1}$ CART were co-incubated with tumor cells. On days 1 and 8, CAR was harvested, stained for flow cytometry, and analyzed on Fortessa flow machine. Statistics were calculated using unpaired t test (*, P<0.0332). (FIGS. 9E-9F) Mice were injected with $CD22^{lo}$ or Nalm6 leukemia on day 0. A total of $5\times10^6$ CD22 CART cells were administered on day 3, and mice were sacrificed on day 16. Bone marrow cells were stained for flow cytometry and analyzed on Fortessa flow machine. Statistics were calculated using unpaired t test (****, P<0.0001; *, P<0.0332).

FIGS. 10A-10E: (FIG. 10A) Three cell lines (Toldeo, Kopn8 and Nalm6) were co-incubated with Bryostatin 1 at varying concentrations for 24 hours. At 24 hours, cells were collected for protein kinase C (PKC)-βII isoform analysis by western blot. (FIG. 10B) KOPN8 or SEM cell lines were exposed to Bryostatin 1 for 16, 24, 48 or 72 hours. RNA was extracted from cells and analyzed using RNAseq. (FIG. 10C) Immunofluorescent staining of CD22 was conducted through permeabilization followed by staining of CD22. (FIG. 10D) Four cell lines were co-incubated with various combinations of Enzastaurin (10 μM), Staurosporine (100 μM), or Bryostatin 1 (1 nM) for 24 hours. CD22 expression was assessed using flow cytometry. MFI fold change=CD22 $MFI^{Bryostatin1}$/CD22 $MFI^{DMSO}$. (FIG. 10E) Cell lines were co-incubated with 1 nM Bryostatin 1 for 24 hours and measured for CD22 expression using CD22-PE antibody. MFI fold change=CD22 $MFI^{Bryostatin\ 1}$/CD22 $MFI^{DMSO}$.

FIG. 12: Amino acid sequence alignment of anti-CD22 m971 scFv and affinity matured variant m971-L7 scFv.

FIGS. 13A-13F: (FIG. 13A) BIAcore analysis was used to evaluate association and dissociation curves of various scFvs. Note: The calculated dissociation rate constant kd ($1.1\times10^{-6}$ 1/s) is lower than the kd which can be measured by the BIAcore X-100 used here ($1.0\times10^{-5}$ 1/s). Therefore, the affinity of the matured variant L7 (KD<$1.0\times10^{-5}$/$5.6\times10^5$=$1.8\times10^{-11}$ M=18 pM) as measured by BIAcore is more than 1000-fold higher than that of the original scFv m971 (KD=3.1 nM). The affinity improvement is also supported by the sorting conditions used during the affinity maturation process. (FIG. 13B) $CD22^{V1}$ or CD22 CART were co-cultured with $CD22^{neg}$ or $CD22^{lo}$ leukemia and evaluated at 24 hours for PD1 expression through flow cytometry on a Fortessa flow machine. (FIGS. 13C-13F) Mice were injected with $CD22^{lo}$ or Nalm6 leukemia on Day 0. $5\times10^6$ CD22 CAR T cells were administered on Day 3 and mice were sacrificed on Day 16. Bone marrow cells were stained for flow cytometry and analyzed on Fortessa flow machine. Statistics were calculated using unpaired t-test (** p<0.0021).

FIGS. 14A-14C: (FIG. 14A) SEM cells were exposed to Bryostatin 1 at 1 nM for 24 hours and washed. CD19 CART were co-incubated with SEM for 16 hours and ELISA was performed for Granzyme B. (FIG. 14B) NSG mice were injected with SEM on Day 0, CD19 CART on Day 3, and then were given either DMSO control or Bryostatin 1 at 40 μg/kg once weekly for 2 weeks. Mice were imaged using IVIS technology and luciferin-D IP injections. (FIG. 14C) NSG mice were injected with Nalm6 on Day 0, CD22 CART on Day 3, and then were given either DMSO control or Bryostatin 1 at 40 μg/kg once weekly for 2 weeks. Mice were sacrificed 30 days after tumor injection. Cells were stained for flow cytometry and analyzed on Fortessa Flow machine.

FIGS. 15A-15C: (FIGS. 15A-B) NSG mice were injected with $1\times10^6$ GPF-positive Nalm6 or SEM tumor cells on Day 0. On Day 3, either $3\times10^6$ (FIG. 15A) or $2\times10^6$ (FIG. 15B) Mock or CD22 CAR were injected for treatment. Mice were given 40 μg/kg of Bryostatin 1 or DMSO once weekly for 2 weeks. Mice were imaged using IVIS technology and luciferin-D IP injections. Luminescence quantification is shown. (FIG. 15C) NSG mice were injected with $1\times10^6$ GPF-positive PDX tumor cells on Day 0. On Day 42, $3\times10^6$ Mock or CD22 CAR were injected for treatment. Mice were given 40 μg/kg of Bryostatin 1 or DMSO once weekly for 2 weeks starting on Day 45. Mice were imaged using IVIS technology and luciferin-D IP injections. Luminescence quantification is shown.

SEQUENCE LISTING

Figure 1A:
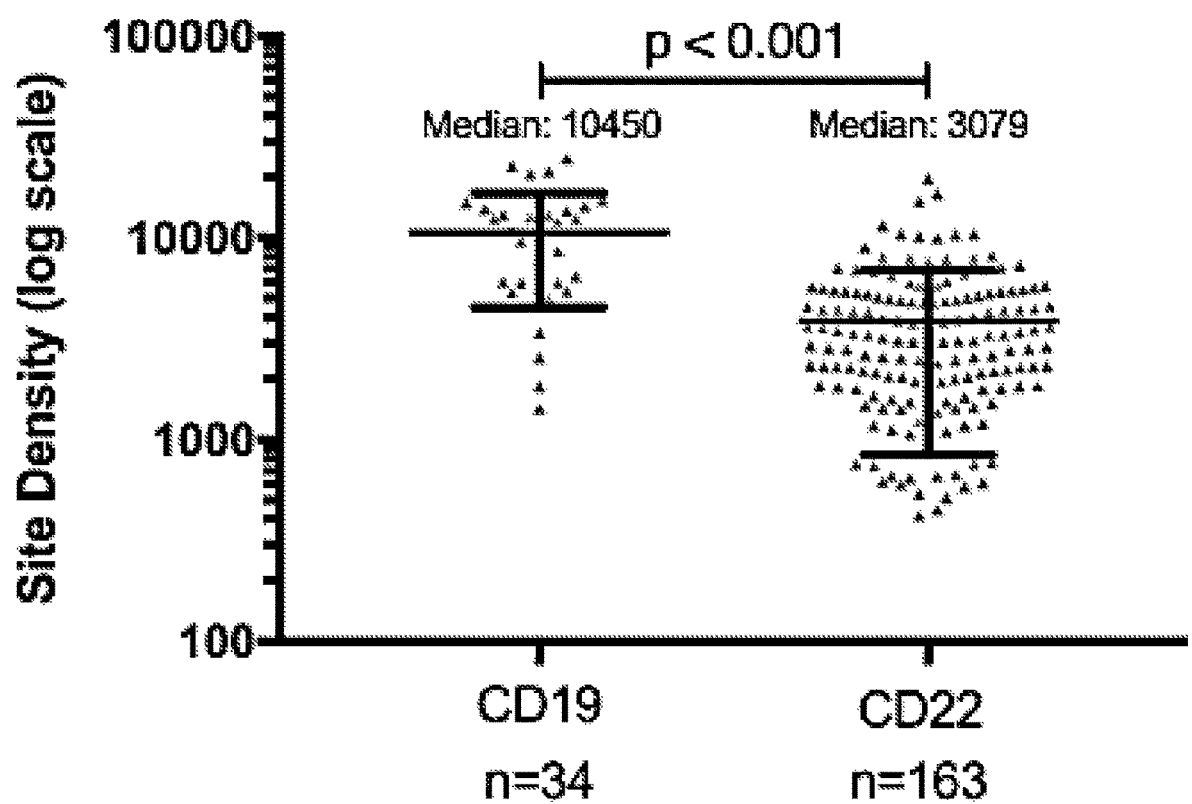

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 29, 2020, 9.78 KB, which is incorporated by reference herein. In the accompanying sequence listing:

SEQ ID NO: 1 is the amino acid sequence of the m971 VH domain.

SEQ ID NO: 2 is the amino acid sequence of the m971 VL domain.

SEQ ID NO: 3 is the amino acid sequence of the m971 scFv.

SEQ ID NO: 4 is the amino acid sequence of the m971-L7 VH domain.

SEQ ID NO: 5 is the amino acid sequence of the m971-L7 VL domain.

SEQ ID NO: 6 is the amino acid sequence of the m971-L7 scFv.

SEQ ID NOs: 7-10 are oligonucleotide primers.

DETAILED DESCRIPTION

I. Abbreviations

ADC antibody drug conjugate
ALL acute lymphoblastic leukemia
CAR chimeric antigen receptor
CART chimeric antigen receptor T-cell
CDR complementarity determining region
CLL chronic lymphocytic leukemia
CRISPR clustered regularly interspaced short palindromic repeats
DLBCL diffuse large B cell lymphoma
DMSO dimethyl sulfoxide
ECD extracellular domain ELISA enzyme-linked immunosorbent assay
GFP green fluorescent protein
GSEA gene set enrichment analysis
HCL hairy cell leukemia
IFN interferon
IL interleukin
IP intraperitoneal
IVIS In Vivo Imaging System
MALT mucosa-associated lymphoid tissue
NHL non-Hodgkin's lymphoma
PE *Pseudomonas exotoxin* or phycoerythrin
PKC protein kinase C
scFv single-chain variable fragment
TCR T cell receptor
VH variable heavy
VL variable light

II. Terms

Unless otherwise noted, technical terms are used according to conventional usage.

Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response.

Administration: To provide or give a subject an agent, such as a therapeutic agent (e.g. an antibody), by any effective route. Exemplary routes of administration include, but are not limited to, injection or infusion (such as subcutaneous, intratumoral, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Antibody: A polypeptide ligand comprising at least one variable region that recognizes and binds (such as specifically recognizes and specifically binds) an epitope of an antigen, such as CD22. Mammalian immunoglobulin molecules are composed of a heavy (H) chain and a light (L) chain, each of which has a variable region, termed the variable heavy ($V_H$) region and the variable light (VL) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), Kunik et al. (see Kunik et al., *PLoS Comput Biol* 8:e1002388, 2012; and Kunik et al., *Nucleic Acids Res* 40 (Web Server issue):W521-524, 2012; "Paratome CDRs") and the ImMunoGeneTics (IMGT) database (see, Lefranc, *Nucleic Acids Res* 29:207-9, 2001; the "IMGT" numbering scheme). The Kabat, Paratome and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_H$H antibodies, and $V_L$ domain antibodies. $V_{NAR}$ antibodies are produced by cartilaginous fish, such as nurse sharks, wobbegong sharks, spiny dogfish and bamboo sharks. Camelid $V_H$H antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

B-cell malignancy: As used herein "B-cell malignancy" includes any type of leukemia or lymphoma of B cells. B-cell malignancies include, but are not limited to, non-Hodgkin's lymphoma, Burkitt's lymphoma, small lymphocytic lymphoma, primary effusion lymphoma, diffuse large B-cell lymphoma (DLBCL), splenic marginal zone lymphoma, mucosa-associated lymphoid tissue (MALT) lymphoma, hairy cell leukemia (HCL), chronic lymphocytic leukemia (CLL) and B-cell prolymphocytic leukemia.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as CD22) is an antibody that binds the antigen with high affinity and does not significantly bind other unrelated antigens.

Bryostatin 1: An anti-cancer macrocyclic lactone isolated from the marine organism *Bugula neritina*. Bryostatin 1 binds to and inhibits protein kinase C (PKC), resulting in inhibition of tumor cell proliferation, promotion of tumor cell differentiation and induction of tumor cell apoptosis. Treatment with Bryostatin 1 increases cell-surface expression of CD22 and enhance toxicity of a CD22-immunotoxin (see, e.g., Biberacher et al., *Haematologica* 97(5): 771-779, 2012). An exemplary structure is shown below Bryostatin 1

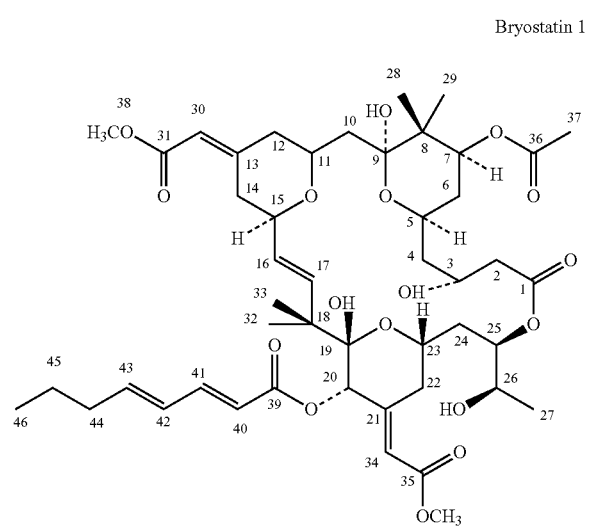

CD22: A lineage-restricted B cell antigen belonging to the immunoglobulin superfamily CD22 is expressed in 60-70% of B cell lymphomas and leukemias. CD22 is not present on the cell surface in the early stages of B cell development or on stem cells. As used herein "CD22" refers to a CD22 polypeptide or variant or fragment thereof. Sequences of human CD22 are publicly available (see, for example Torres et al., *J. Immunol.* 149(8):2641-2649, 1992; and Wilson et al., *J. Exp. Med.* 173(1):137-146, 1991). The term "CD22" also includes soluble forms of CD22, referred to as sCD22.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is a radioactive compound. In one embodiment, a chemotherapeutic agent is a biologic, such as a monoclonal antibody. One of skill in the art can readily identify a chemotherapeutic agent of use (see, for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of a CAR T cell used in combination with a radioactive or chemical compound, such as an agent that increases CD22 expression, such as Bryostatin 1.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs are comprised of an antigen-binding moiety, a transmembrane domain and an intracellular domain. The intracellular domain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10.

Chronic lymphocytic leukemia (CLL) is a lymphoproliferative disorder characterized by lymphocytosis, lymphadenopathy, and organomegaly. CLL is a lymphoma that involves the peripheral blood.

Complementarity determining region (CDR): A region of hypervariable amino acid sequence that defines the binding affinity and specificity of an antibody. The light and heavy chains of a mammalian immunoglobulin each have three CDRs, designated L-CDR1, L-CDR2, L-CDR3 and H-CDR1, H-CDR2, H-CDR3, respectively.

Conservative variant: "Conservative" amino acid substitutions are those substitutions that do not substantially affect or decrease the affinity of a protein, such as an antibody to CD22. As one example, a monoclonal antibody that specifically binds CD22 can include at most about 1, at most about 2, at most about 5, and most about 10, or at most about 15 conservative substitutions and specifically bind the CD22 polypeptide. The term "conservative variant" also includes the use of a substituted amino acid in place of an unsubstituted parent amino acid, provided that the variant retains activity. Non-conservative substitutions are those that reduce an activity of a protein.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some embodiments herein, provided are amino acid sequences comprising no more than 10, no more than 9, no more than 8, no more than 7, no more than 6, no more than 5, no more than 4, no more than 3, no more than 2 or no more than 1 amino acid substitutions relative to SEQ ID NO: 4, SEQ ID NO: 5, or SEQ ID NO: 6. In some embodiments, the substitutions occur only in the framework region of an antibody.

Cytotoxic agent: Any drug or compound that kills cells.

Cytotoxicity: The toxicity of a molecule to the cells intended to be targeted, as opposed to the cells of the rest of an organism.

Degenerate variant: A polynucleotide encoding a polypeptide that includes a sequence that is degenerate as a result of the genetic code. There are 20 natural amino acids, most of which are specified by more than one codon. Therefore, all degenerate nucleotide sequences are included as long as the amino acid sequence of the polypeptide is unchanged.

Epitope: An antigenic determinant. These are particular chemical groups or peptide sequences on a molecule that are antigenic, i.e. that elicit a specific immune response. An antibody specifically binds a particular antigenic epitope on a polypeptide.

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Hairy cell leukemia (HCL) is a malignant disorder of small B-lymphocytes that gets its name from the presence of cytoplasmic projections in these cells. Subjects with HCL commonly present with pancytopenia, splenomegaly and marrow fibrosis. The peripheral blood usually contains a small number of hairy cells. Hairy cells proliferate in the red pulp of the spleen, so splenomegaly is common.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^3H$, $^{14}C$, $^{15}N$, $^{90}Y$, $^{99}Tc$, $^{111}In$ and $^{125}I$), fluorescent labels (such as fluorescein isothiocyanate (FITC), rhodamine, Cy5, Cy3, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. One example of a linker for joining the VH and VL domains of a scFv is (GGGS)$_4$ (residues 125-139 of SEQ ID NO: 6). "Linker" can also refer to a peptide serving to link a targeting moiety, such as an antibody, to an effector molecule, such as a cytotoxin or a detectable label. The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Non-Hodgkin's lymphoma (NHL): Refers to a heterogeneous group of cancers principally arising from B lymphocytes. The subtypes of NHL are typically grouped into three distinct categories based on their aggressiveness, or histologic grade. These categories are indolent (low-grade), aggressive (intermediate-grade) and highly aggressive (high-grade). NHLs include, but are not limited to, diffuse large B-cell lymphoma, mantle cell lymphoma, MALT lymphoma, follicular lymphoma, small lymphocytic lymphoma and Burkitt's lymphoma.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, PA, 15th Edition, 1975, describes compositions and formulations suitable for pharmaceutical delivery of the compositions disclosed herein, such as those that include a CD22 antibody or fragment thereof.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein (such as an antibody or antigen-binding fragment thereof provided herein) is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as a tumor tissue biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a VL or a VH of an antibody that specifically binds a CD22 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Soluble CD22 (sCD22): A non-membrane-bound form of CD22, a 135 kDa phosphoglycoprotein adhesion molecule present on the surface of B cells, including human B cell malignancies. Soluble CD22 can be any portion of the CD22 protein not connected to the membrane, and is usually a truncated form of CD22. For example, sCD22 can be about 100 kDa, however it can also be no more than or no less than about 90, 80, 70, 60, 50, 40, or 30 kDa, or smaller. Standard software is available for determining the transmembrane domain of CD22.

Subject: Living multi-cellular vertebrate organisms, a category that includes both human and veterinary subjects, including human and non-human mammals. In one example, a subject treated with the disclosed methods has a B-cell malignancy.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress progression of a B-cell malignancy. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements.

III. Overview of Several Embodiments

Disclosed herein is an affinity matured human monoclonal antibody (m971-L7) with high affinity for the B cell antigen CD22. The binding affinity of m971-L7 for CD22 is less than 50 pM, which is significantly improved relative to the binding affinity of parental antibody m971 for CD22 (about 2 nM). The amino acid sequences of the m971-L7 VH domain, VL domain, and scFv are provided below. The CDR regions (as determined by IMGT) are shown in underline and the residues of CDR1, CDR2 and CDR3 are indicated below each sequence. Bold residues indicate amino acid substitutions relative to parental antibody m971. In the scFv sequence, the linker region between the VH and VL domains is indicated by the italicized residues. Although IMGT CDR regions are indicated below, one of skill in the art could readily determine the CDR boundaries using alternative numbering schemes, such as the Kabat, Paratome or Chothia numbering schemes.

```
m971-L7 VH domain
                                           (SEQ ID NO: 4)
QVQLQQSGPGMVKPSQTLSLTCAISGDSVSSNSVAWNWIRQSPSRGLEWL

GRTYYRSTWYNDYAVSMKSRITINPDTNKNQFSLQLNSVTPEDTAVYYCA

REVTGDLEDAFDIWGQGTMVTVSS

CDR1 = residues 26-35; CDR2 = residues 53-61; and

CDR3 = residues 100-113 m971-L7 VL domain
                                           (SEQ ID NO: 5)
DIQMIQSPSSLSASVGDRVTITCRASQTIWSYLNWYRQRPGEAPNLLIYA

ASSLQSGVPSRFSGRGSGTDFTLTISSLQAEDFATYYCQQSYSIPQTFGQ

GTKLEIK

CDR1 = residues 27-32; CDR2 = residues 50-52; and

CDR3 = residues 89-97 m971-L7 scFv
                                           (SEQ ID NO: 6)
QVQLQQSGPGMVKPSQTLSLTCAISGDSVSSNSVAWNWIRQSPSRGLEWL

GRTYYRSTWYNDYAVSMKSRITINPDTNKNQFSLQLNSVTPEDTANTYYC

AREVTGDLEDAFDIWGQGTMVTVSSGGGGSGGGGSGGGGSDIQMIQSPSS

LSASVGDRVTITCRASQTIWSYLNWYRQRPGEAPNLLIYAASSLQSGVPS

RFSGRGSGTDFTLTISSLQAEDFATYYCQQSYSIPQTFGQGTKLEIK
```

```
HCDR1 = residues 26-35; HCDR2 = residues 53-61;

HCDR3 = residues 100-113; linker = residues 125-

139; LCDR1 = residues 166-171; LCDR2 = residues 189-191; and LCDR3 = residues 228-236.
```

Provided herein are monoclonal antibodies or antigen-binding fragments that bind (such as specifically bind) CD22, such as cell-surface CD22 or soluble CD22. In some embodiments, the monoclonal antibody or antigen-binding fragment that binds CD22 includes at least one CDR sequence from antibody m971-L7. In some embodiments, the CDR sequences are determined using the IMGT, Kabat, Paratome or Chothia numbering scheme.

In some embodiments, the CD22-specific monoclonal antibody or antigen-binding fragment includes a VH domain and a VL domain, and the VH domain of the antibody includes one, two or all three CDR sequences of SEQ ID NO: 4, and/or the VL domain of the antibody includes one, two or all three CDR sequences of SEQ ID NO: 5. In some examples, the VH domain comprises residues 26-35, 53-61 and 100-113 of SEQ ID NO: 4 and/or the VL domain comprises residues 27-32, 50-52 and 89-97 of SEQ ID NO: 5.

In particular examples, the amino acid sequence of the VH domain is at least 80%, at least 85%, at least 90%, at least 95%, at least 96%, at least 97%, at least 98% or at least 99% identical to SEQ ID NO: 4 (while retaining the specific CDR sequences of SEQ ID NO: 4) and the amino acid sequence of the VL domain is at least 80%, at least 85%, at least 90%, at least 95%, at least 96%, at least 97%, at least 98% or at least 99% identical to SEQ ID NO: 5 (while retaining the specific CDR sequences of SEQ ID NO: 5). In specific non-limiting examples, the amino acid sequence of the VH domain comprises SEQ ID NO: 4 and the amino acid sequence of the VL domain comprises SEQ ID NO: 5.

CD22-specific antigen-binding fragments that include both a VH domain and a VL domain can be, for example, an Fab fragment, an Fab' fragment, an F(ab)' 2 fragment, a single chain variable fragment (scFv) or a disulfide stabilized variable fragment (dsFv). In some embodiments, the antigen-binding fragment is a scFv. In some examples, the amino acid sequence of the scFv is at least 80%, at least 85%, at least 90%, at least 95%, at least 96%, at least 97%, at least 98% or at least 99% identical to SEQ ID NO: 6.

CD22-specific monoclonal antibodies can be of any isotype, such as IgG, IgM, IgA, IgD or IgE. In some embodiments, the monoclonal antibody is an IgG.

In some embodiments, the monoclonal antibody or antigen-binding fragment is a fully human antibody or antigen-binding fragment. In some embodiments, the monoclonal antibody or antigen-binding fragment is a chimeric or synthetic antibody or antigen-binding fragment.

Also provided herein are chimeric antigen receptors (CARs) that include a monoclonal antibody or antigen-binding fragment disclosed herein. In some embodiments, the CAR further includes a hinge region, a transmembrane domain, a costimulatory signaling moiety, a signaling domain, or any combination thereof. In some examples, the hinge region includes a CD8 hinge region; the transmembrane domain includes a CD8 transmembrane domain; the costimulatory signaling moiety includes a 4-1BB signaling moiety; and/or the signaling domain comprises a CD3ζ signaling domain. Further provided are cells expressing a CD22-specific CAR. In some examples, the cell is a CTL. CARs and CAR-expressing T cells are further described in section IV.

Also provided herein are immunoconjugates that include a monoclonal antibody or antigen-binding fragment disclosed herein and an effector molecule. In some embodiments, the effector molecule is a toxin, such as, but not limited to, *Pseudomonas exotoxin* or a variant thereof. In other embodiments, the effector molecule is a detectable label, such as, but not limited to, a fluorophore, an enzyme or a radioisotope. Immunoconjugates are further described in section V.

Further provided herein are antibody-drug conjugates (ADCs) that include a drug conjugated to a monoclonal antibody or antigen-binding fragment disclosed herein. In some embodiments, the drug is a small molecule, for example an anti-microtubule agent, an anti-mitotic agent and/or a cytotoxic agent. In one example, the drug is Bryostatin 1. ADCs are further described in section VI.

Also provided herein are multi-specific antibodies that include a monoclonal antibody or antigen-binding fragment disclosed herein and at least one additional monoclonal antibody or antigen-binding fragment thereof. In some embodiments, the multi-specific antibody is a bispecific antibody. In other embodiments, the multi-specific antibody is a trispecific antibody. In some embodiments, the at least one additional monoclonal antibody or antigen binding fragment thereof specifically binds a component of the T cell receptor or a natural killer (NK) cell activating receptor. Multi-specific antibodies are further described in section VII.

Further provided herein are antibody-nanoparticle conjugates that include a nanoparticle conjugated to a monoclonal antibody or antigen-binding fragment disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section VIII.

Also provided herein are fusion proteins that include a monoclonal antibody or antigen-binding fragment disclosed herein and a heterologous protein or peptide. In some embodiments, the heterologous protein is an Fc protein. In some examples, the Fc protein is a mouse Fc or a human Fc protein. In some embodiments, the heterologous peptide is not endogenous to humans (for example, the heterologous peptide is a peptide neo-epitope). In some embodiments, the heterologous peptide is about 8 to about 20 amino acids in length. In particular examples, the heterologous peptide is about 14 amino acids in length.

Compositions that include a pharmaceutically acceptable carrier and a monoclonal antibody or antigen-binding fragment, CAR, isolated cell, immunoconjugate, ADC, multi-specific antibody, antibody-nanoparticle conjugate, or fusion protein disclosed herein are further provided by the present disclosure.

Also provided are nucleic acid molecules encoding a monoclonal antibody or antigen-binding fragment disclosed herein. Further provided are nucleic acid molecules encoding a CAR, immunoconjugate, multi-specific antibody, or fusion protein disclosed herein. In some embodiments, the nucleic acid molecule is operably linked to a promoter. Vectors that include the nucleic acid molecules are further provided herein.

Also provided herein are methods of treating a B-cell malignancy in a subject. In some embodiments, the method includes administering to the subject a monoclonal antibody or antigen-binding fragment disclosed herein, or administering a CAR (or CAR-expressing T cell), immunoconjugate, ADC, multi-specific antibody, antibody-nanoparticle conjugate, fusion protein, or composition comprising a monoclonal antibody or antigen-binding fragment disclosed herein. In some examples, the B-cell malignancy is acute lymphoblastic leukemia (ALL), non-Hodgkin's lymphoma, Burkitt's lymphoma, small lymphocytic lymphoma, primary effusion lymphoma, diffuse large B-cell lymphoma, splenic marginal zone lymphoma, mucosa-associated lymphoid tissue (MALT) lymphoma, hairy cell leukemia, chronic lymphocytic leukemia or B-cell prolymphocytic leukemia. In some embodiments, the method further includes further administering a second therapeutic agent such as an agent that enhances the effect of the CD22 monoclonal antibody or conjugate thereof. In some examples, the second therapeutic agent comprises Bryostatin 1. In some examples, Bryostatin 1 is administered prior to or simultaneously with administration of the monoclonal antibody, antigen-binding fragment, CAR, isolated cell, immunoconjugate, ADC, multi-specific antibody, antibody-nanoparticle conjugate, fusion protein or composition. In specific examples, the method of treating a B-cell malignancy in a subject includes administering to the subject a CAR T-cell disclosed herein and Bryostatin 1.

Further provided is a method of detecting expression of CD22 in a sample. In some embodiments, the method includes contacting the sample with a monoclonal antibody or antigen-binding fragment disclosed herein; and detecting binding of the antibody to the sample. In some examples, the monoclonal antibody or antigen-binding fragment is directly labeled. In other examples, the method further includes contacting the monoclonal antibody or antigen-binding fragment with a second antibody, and detecting the binding of the second antibody to the monoclonal antibody or antigen-binding fragment. In some examples, the sample is obtained from a subject suspected of having a B-cell malignancy. In some examples, the sample is a blood sample.

Also provided is a method of diagnosing a subject as having a B-cell malignancy. In some embodiments, the method includes contacting a sample from the subject with a CD22-specific monoclonal antibody or antigen-binding fragment disclosed herein, and detecting binding of the antibody to the sample. An increase in binding of the antibody to the sample as compared to binding of the antibody to a control sample identifies the subject as having a B-cell malignancy. In some examples, the sample is a blood sample.

A method of confirming the diagnosis of a B-cell malignancy in a subject is further provided. In some embodiments, the method includes contacting a sample from a subject diagnosed with a B-cell malignancy with a CD22-specific monoclonal antibody or antigen-binding fragment disclosed herein, and detecting binding of the antibody to the sample. An increase in binding of the antibody to the sample as compared to binding of the antibody to a control sample confirms the diagnosis of a B-cell malignancy in the subject. In some examples, the sample is a blood sample. In some examples, the B-cell malignancy is acute lymphoblastic leukemia (ALL), non-Hodgkin's lymphoma, Burkitt's lymphoma, small lymphocytic lymphoma, primary effusion lymphoma, diffuse large B-cell lymphoma, splenic marginal zone lymphoma, mucosa-associated lymphoid tissue (MALT) lymphoma, hairy cell leukemia, chronic lymphocytic leukemia or B-cell prolymphocytic leukemia.

Further provided is a kit that includes a monoclonal antibody or antigen-binding fragment, a CAR, an isolated cell, an immunoconjugate, an ADC, a multi-specific antibody, an antibody-nanoparticle conjugate, a fusion protein, or a composition disclosed herein, and an agent that upregulates CD22 expression. In some examples, the kit further includes an anti-cancer agent. In some examples the agent that upregulates CD22 expression comprises or consists of Bryostatin 1.

IV. Chimeric Antigen Receptors (CARs)

The disclosed CD22 monoclonal antibodies can be used to produce CARs (also known as chimeric T cell receptors, artificial T cell receptors or chimeric immunoreceptors) and/or cytotoxic T lymphocytes (CTLs) can be engineered to express the CARs. Generally, CARs include a binding moiety, an extracellular hinge and spacer element, a transmembrane region and an endodomain that performs signaling functions (Cartellieri et al., *J Biomed Biotechnol* 2010: 956304, 2010). In many instances, the binding moiety is an antigen binding fragment of a monoclonal antibody, such as a scFv, or is a single-domain antibody. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, a tumor-antigen specific monoclonal antibody can be used to engineer CTLs that express a CAR containing an antigen-binding fragment of an antigen-specific antibody, thereby targeting the engineered CTLs to tumor antigen-expressing tumor cells (such as tumor cells expressing CD22). Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, T cells expressing CARs that include a CD22 antibody or antigen-binding fragment, can be used to directly target CD22-expressing tumors. In some embodiments, the CAR is a bispecific CAR.

V. Immunoconjugates

The disclosed CD22 monoclonal antibodies can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas exotoxin* or diphtheria toxin, encapsulating agents (such as liposomes) that contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies or antibody fragments can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging (NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with a monoclonal antibody to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, MO). Contemplated toxins also include variants of the toxins described herein (see, for example, see, U.S. Pat. Nos. 5,079,163 and 4,689,401). In one embodiment, the toxin is *Pseudomonas exotoxin* (PE) (U.S. Pat. No. 5,602,095). As used herein "*Pseudomonas exotoxin*" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with a monoclonal antibody can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Nall Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

Antibodies can also be used to target any number of different diagnostic or therapeutic compounds to cells expressing the tumor antigen on their surface. Thus, an antibody can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VI. Antibody-Drug Conjugates (ADCs)

ADCs are compounds comprised of an antigen-specific, such as a tumor antigen-specific, antibody (or antigen-binding fragment thereof) and a drug, typically a cytotoxic agent, such as an anti-microtubule agent or cross-linking agent. Because ADCs are capable of specifically targeting particular cell types, such as cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-GO glycoform. The mutant β1,4-galactosyltransferase enzyme is capable of transferring 2-keto-galactose or 2-azido-galactose from their respective UDP derivatives to the GlcNAc residues on the IgG-G1 and IgG-GO glycoforms. The chemical handle on the transferred sugar enables conjugation of a variety of molecules to the monoclonal antibody via the glycan residues (Qasba et al., *Biotechnol Prog* 24:520-526, 2008).

In some embodiments, the ADC is comprised of a CD22-specific antibody disclosed herein conjugated to a drug to specifically target CD22-positive tumors. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, vinca alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc*, 87:5793-5795, 1965; Leimgruber et al., *J Am Chem Soc*, 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitototic inhibitors which act by inhibiting tubulin polymerization. Maytansine was first isolated from the east African shrub

*Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663,149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

VII. Multi-Specific Antibodies

Multi-specific antibodies are recombinant proteins comprised of antigen-binding fragments of two or more different monoclonal antibodies. For example, bispecific antibodies are comprised of antigen-binding fragments of two different monoclonal antibodies. Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The antigen-specific monoclonal antibodies disclosed herein can be used to generate multi-specific (such as bispecific or trispecific) antibodies that target both the antigen (e.g. CD22) and CTLs, or target both the antigen and NK cells, thereby providing a means to treat tumor antigen-expressing cancers.

Bi-specific T-cell engagers (BiTEs) are a type of bispecific monoclonal antibody that are fusions of a first single-chain variable fragment (scFv) that targets a specific antigen and a second scFv that binds T cells, such as bind CD3 on T cells. In some embodiments herein, one of the binding moieties of the BiTE (such as one of the scFv molecules) is specific for CD22.

Bi-specific killer cell engagers (BiKEs) are a type of bispecific monoclonal antibody that are fusions of a first scFv that targets a specific antigen and a second scFv that binds a NK cell activating receptor, such as CD16. In some embodiments herein, one of the binding moieties of the BiKE (such as one of the scFv molecules) is specific for CD22.

Provided herein are multi-specific, such as trispecific or bispecific, monoclonal antibodies comprising a CD22-specific monoclonal antibody, or antigen-binding fragment thereof. In some embodiments, the multi-specific monoclonal antibody further comprises a monoclonal antibody, or antigen-binding fragment thereof, that specifically binds a component of the T cell receptor, such as CD3. In other embodiments, the multi-specific monoclonal antibody further comprises a monoclonal antibody, or antigen-binding fragment thereof, that specifically binds a NK cell activating receptor, such as CD16, Ly49, or CD94. In yet other embodiments, the multi-specific monoclonal antibody further comprises a monoclonal antibody, or antigen-binding fragment thereof, that specifically binds a tumor antigen. In some examples, the antigen-binding fragments are scFv. Also provided are isolated nucleic acid molecules and vectors encoding the multi-specific antibodies, and host cells comprising the nucleic acid molecules or vectors.

VIII. Antibody-Nanoparticle Conjugates

The disclosed CD22-specific monoclonal antibodies, or antigen-binding fragments thereof, can be conjugated to a variety of different types of nanoparticles to deliver cytotoxic agents or other anti-cancer agents directly to tumor cells via binding of the antibody to CD22 expressed on the surface of tumor cells.

The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, *Immunotherapy* 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine Niosomes range from small, unilalamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly (glycolic acids) (PGA), and poly(D,L-lactic-co-glycolic acid) (PLGA).

Antibodies can be conjugated to a suitable nanoparticle according to standard methods known in the art. For example, conjugation can be either covalent or non-covalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31) 5239-5277, 2012).

IX. Compositions and Methods of Use

Compositions are provided that include one or more of the disclosed antibodies that bind (for example specifically bind) CD22 in a carrier. Compositions comprising CARs (and T lymphocytes comprising CARs), ADCs, multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, CAR, ADC, CAR-expressing T lymphocyte, multi-specific antibody, antibody-nanoparticle conjugate, immunoliposome or immunoconjugate can be formulated for systemic or local administration. In one example, the antibody is formulated for parenteral administration, such as intravenous administration.

The compositions for administration can include a solution of the antibody, antigen-binding fragment, ADC, CAR, CAR-expressing T lymphocyte, multi-specific (such as bispecific or trispecific) antibody, antibody-nanoparticle conjugate, immunoliposome and/or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, PA (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN™ in 1997. Antibodies, ADCs, CARs, CAR-expressing T lymphocytes, multi-specific (such as bispecific or trispecific) antibodies, antibody-nanoparticle conjugates, immunoliposomes and/or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies and compositions disclosed herein can be administered to slow or inhibit the growth of tumor cells, or to inhibit the metastasis of tumor cells. In these applications, a therapeutically effective amount of a composition is administered to a subject in an amount sufficient to inhibit growth, replication or metastasis of cancer cells and/or to inhibit a sign or a symptom of the cancer.

Provided herein is a method of treating a B-cell malignancy in a subject by administering to the subject a therapeutically effective amount of a CD22-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. In some embodiments, the B-cell malignancy is ALL, non-Hodgkin's lymphoma, Burkitt's lymphoma, small lymphocytic lymphoma, primary effusion lymphoma, diffuse large B-cell lymphoma, splenic marginal zone lymphoma, MALT lymphoma, hairy cell leukemia, chronic lymphocytic leukemia or B-cell prolymphocytic leukemia.

A therapeutically effective amount of a CD22-specific antibody or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the antibodies, antibody conjugates and compositions disclosed herein can also be accompanied by administration of other anti-cancer agents or therapeutic treatments. In some embodiments, the CD22-specific antibody, antibody conjugate or composition is administered in combination with radiotherapy, chemotherapy, an ADC, an immunotoxin, a CAR-expressing T cell, or an immune checkpoint targeted therapy, such as anti-cytotoxic T-lymphocyte-associated protein 4 (CTLA-4) antibody, anti- OX40 antibody, anti-glucocorticoid-induced TNF receptor-related (GITR) antibody, anti-inducible co-stimulator (ICOS) antibody, anti-lymphocyte activation gene 3 (LAGS) antibody, anti-T-cell immunoglobulin domain and mucin domain 3 (TIM3) antibody, anti-CD276 (B7-H3) antibody, or an indoleamine 2,3-dioxygenase (IDO) inhibitor.

Any suitable anti-cancer agent can be administered in combination with the antibodies, compositions and conjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Exemplary chemotherapy drugs that can be used in combination with the disclosed CD22 antibodies (or antigen-binding fragments thereof) include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

In some embodiments, a subject is administered an agent that increases expression of CD22. The agent can be administered prior to, or simultaneously with, administration of an antibody or antibody conjugate disclosed herein. In particular examples, the agent that upregulates expression of CD22 is Bryostatin 1.

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting CD22 protein in vitro or in vivo. In some cases, CD22 expression is detected in a biological sample. The sample can be any sample, including, but not limited to, blood samples, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

Provided herein is a method of detecting expression of CD22 in a sample. In some embodiments, the method includes contacting the sample with a CD22-specific monoclonal antibody or antigen-binding fragment disclosed herein, and detecting binding of the antibody to the sample. In some examples, the sample is a blood, cell or tissue sample.

Also provided herein is a method of determining if a subject has a B-cell malignancy by contacting a sample from the subject with a CD22-specific monoclonal antibody disclosed herein; and detecting binding of the antibody to the sample. An increase in binding of the antibody to the sample as compared to binding of the antibody to a control sample identifies the subject as having a B-cell malignancy.

In another embodiment, provided is a method of confirming a diagnosis of a B-cell malignancy in a subject by contacting a sample from a subject diagnosed with a B-cell malignancy with a CD22-specific monoclonal antibody disclosed herein; and detecting binding of the antibody to the sample. An increase in binding of the antibody to the sample as compared to binding of the antibody to a control sample confirms the diagnosis of a B-cell malignancy in the subject.

In some examples of the disclosed methods, the monoclonal antibody is directly labeled. In other examples, the methods further include contacting a second antibody that specifically binds the monoclonal antibody with the sample; and detecting the binding of the second antibody. An increase in binding of the second antibody to the sample as compared to binding of the second antibody to a control sample detects expression of CD22 expression in the sample. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^3$H.

In an alternative embodiment, CD22 protein can be assayed in a biological sample by a competition immunoassay utilizing CD22 protein standards labeled with a detectable substance and an unlabeled antibody that specifically binds CD22. In this assay, the biological sample, the labeled CD22 protein standards and the antibody that specifically binds CD22 are combined and the amount of labeled CD22 protein standard bound to the unlabeled antibody is determined. The amount of CD22 in the biological sample is inversely proportional to the amount of labeled CD22 protein standard bound to the antibody that specifically binds CD22.

The immunoassays and methods disclosed herein can be used for a number of purposes. In one embodiment, the antibody that specifically binds CD22 may be used to detect the production of CD22 in cells in cell culture. In another embodiment, the antibody can be used to detect the amount of CD22 in a biological sample, such as a tissue sample, or a blood or serum sample. In some examples, the CD22 is cell-surface CD22. In other examples, the CD22 is soluble (e.g. in a cell culture supernatant or in a body fluid sample, such as a blood or serum sample).

In one embodiment, a kit is provided for detecting CD22 in a biological sample, such as a blood sample or tissue sample. Kits for detecting a polypeptide will typically include a monoclonal antibody that specifically binds CD22, such as CD22 antibody disclosed herein. In a further embodiment, the antibody is labeled (for example, with a fluorescent, radioactive, or an enzymatic label).

In one embodiment, a kit includes instructional materials disclosing means of use of an antibody that binds CD22. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting CD22 in a biological sample generally includes the steps of contacting the biological sample with an antibody which specifically reacts, under immunologically reactive conditions, to CD22. The antibody is allowed to specifically bind under immunologically reactive conditions to form an immune complex, and the presence of the immune complex (bound antibody) is detected directly or indirectly.

The antibodies disclosed herein can also be utilized in immunoassays such as but not limited to radioimmunoassays (RIAs), ELISA, Western blot, immunoprecipitation assays or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620).

The following examples are provided to illustrate certain particular features and/or embodiments. These examples should not be construed to limit the disclosure to the particular features or embodiments described.

EXAMPLES

Example 1: Materials and Methods

This example describes the materials and experimental procedures used for the studies described in Example 2.

Clinical Trial and Patient Data

Patients screened for enrollment on CD19 CART (NCT02028455) or CD22 CART (NCT02315612) trials at the NCI were evaluated for site density of both CD19 and CD22 antigens on the surface of leukemic blasts, measured using previously described flow cytometric methods (Jasper et al., *Cytometry B Clin Cytom* 80(2):83-90, 2011). Patients treated on the CD22 CAR trial also had serial evaluations for CD22 at the time of enrollment and at relapse. Additionally, four CD22 CART trial patients were evaluated for CAR T cell expansion over time by flow cytometry.

Mice, Cell Lines, Patient-Derived Xenografts, and Healthy Donor Lymphocytes

B-ALL cell lines used included Nalm6 GFP luciferase transduced, obtained from Dr. Crystal Mackall, Pediatric Oncology Branch, NCI, NIH, Bethesda, MD, and SEM GFP luciferase transduced and Kopn8 GFP luciferase transduced, obtained from Dr. Sarah Tasian, Children's Hospital of Philadelphia, Philadelphia, PA Previously generated CRISPR variants of Nalm6-GFP$^+$ cell line were used, including CD22$^{neg}$, CD22$^{lo}$, and CD22$^{hi}$ (Fry et al., *Nat Med.* 2018; 24(1):20-28). DLBCL cell lines used included Pfeiffer and Toledo, obtained from ATCC. All cell lines were routinely tested for *Mycoplasma* by Luminescence *Mycoplasma* Test (Cambrex MycoAlert). All experiments were done within 2 weeks of thawing cell line. Leukemia and lymphoma cell lines were cultured in RPMI medium supplemented with 10% heat-inactivated FBS, 100 U/mL penicillin, 100 U/mL streptomycin, 2 mmol/L L-glutamine, and 10 mmol/L HEPES. Human healthy donor peripheral blood mononuclear cells were obtained from the Department of Transfusion Medicine at the NIH under an institutional review board-approved protocol and were frozen in 10% FBS and stored in liquid nitrogen for future use. The patient-derived xenograft (PDX) was developed from a patient who relapsed with CD22-low leukemia following CD22 CART. The PDX cell line was created by injecting 1×10$^6$ to 10×10$^6$ patient ALL cells intravenously into NSG mice (NOD scid gamma, NOD.Cg-Prkdcscid Il2rgtm1Wjl/SzJ; Jackson ImmunoResearch Laboratories). After the second passage, the cell line was transduced with a lenti-GFP-Luc virus and sorted for the leukemia cells expressing GFP luciferase.

Generation of Site Density Model

As described previously, site density model cell lines were developed through CRISPR/Cas9 editing to remove CD22. Specifically, guide-RNAs were designed from a GeCKO human sgRNA library, and then cloned into LentiCRISPR v2 plasmid (Addgene Plasmid 52961). These guide-RNAs were transformed into Stbl3 bacteria. Plasmids were co-transfected with packaging plasmids RRE, pMD-G, and REV into LentiX HEK293T cells (Clontech, Mountain View, CA, USA). Two days later, CRISPR supernatants were harvested and filtered through a 0.45 μm low protein binding membrane (Millipore, Billerica, Massachusetts, USA). Supernatant was concentrated using Lenti-X concentrator (Clontech, Mountain View, CA, USA), resuspended in PBS, and used immediately or stored at −80° C. Cell phenotype was assessed by flow cytometry, followed by sorting of cells with phenotypic alterations and single cell cloning. Single cell clones were sequenced to confirm genotypic alterations by Platinum PCR Supermix High Fidelity Kit (Invitrogen) (hCD19F Seq: 5' TCTCCCTCTCCTGGGTG 3' (SEQ ID NO: 7), hCD19R Seq: 5' CTCTCCCTCCCAGATCTCAG 3' (SEQ ID NO: 8), hCD22F Seq: 5' AGGAGGGAAGGGGTACTG 3' (SEQ ID NO: 9), and hCD22R Seq: 5' AGCCAACGTTTTGGATCTTCAG 3' (SEQ ID NO: 10)). A complete sequence of cDNA human CD22 plasmid (Origene) was re-transduced at different concentrations into the CD22-negative cell line to obtain cell lines with various CD22 site densities. Cell lines were single-cell cloned with resultant cell lines including CD22-negative (CD22$^{neg}$), CD22-low site density (CD22$^{lo}$), and CD22-high site density (CD22$^{hi}$) cell lines. QuantiBRITE Beads (BD Biosciences, San Jose, CA, USA) were used to confirm site density of CRISPR/Cas9-modified cell lines.

Affinity Maturation of m971

To increase the affinity of CD22-specific monoclonal antibody m971 (WO 2009/124109, herein incorporated by reference in its entirety), a yeast-display m971 mutant scFv library was created by using error-prone PCR to create random point mutations in scFv gene sequences. After electroporation, the resulting mutant library was grown overnight at 30° C. for 16 hours in SDCAA medium and then switched into SGCAA medium at 30° C. for another 16 hours. The mutant library was sorted through MACS (immunomagentic column, Miltenyi Biotec) with CD22-Fc as the capture antigen to downsize the library and to increase the population of mutants that could bind to CD22-Fc. The strongest binders were then sorted by double staining the pools with Anti-c-Myc-Alexa 488 and CD22-Fc/Anti-Hu-Fc PE conjugates and gating for the binders that had the highest antigen binding signal versus c-Myc expression signal. This process was then repeated two more cycles, until yeast displayed m971 mutants reach expected affinity. This process resulted in an increase of EC50 (effective concentration for 50% binding of CD22-Fc to yeast display scFv) for m971 of 0.5 μg/ml to an affinity of <0.01 μg/ml for the affinity matured mutant pool. Single clones were selected from the affinity matured pool and further characterized through DNA sequencing and a series of binding assays. Binding affinities of the parent clone and affinity matured single clones (including m971-L7) were measured by Biacore.

Amino Acid Sequences of m971 scFv and Affinity Matured Clone m971-L7

Affinity matured clone m971-L7 was selected for further analysis. Sequencing of m971-L7 scFv identified seven amino acid changes compared to parental m971 scFv (see FIG. 12). The amino acid sequences of the parental m971 and variant m971-L'7 are provided below. CDR sequences are underlined and bolded residues in the m971-L7 sequence indicate amino acid substitutions relative to m971.

m971 VH domain
(SEQ ID NO: 1)
QVQLQQSGPGLVKPSQTLSLTCAIS<u>GDSVSSNSAA</u>WNWIRQSPSRGLEWL G<u>RTYYRSKWYNDYAVSV</u>KSRITINPDTSKNQFSLQLNSVTPEDTAVYYC<u>A</u>

<u>REVTGDLEDAFDI</u>WGQGTMVTVSS

HCDR1 = residues 26-35; HCDR2 = residues 53-61;

and HCDR3 = residues 100-113 m971 VL domain
(SEQ ID NO: 2)
DIQMTQSPSSLSASVGDRVTITCRAS<u>QTIWSY</u>LNWYQQRPGKAPNLLIY <u>AAS</u>SLQSGVPSRFSGRGSGTDFTLTISSLQAEDFATYYC<u>QQSYSIPQT</u>F

GQGTKLEIK

CDR1 = residues 27-32; CDR2 = residues 50-52; and

CDR3 = residues 89-97 m971 scFv
(SEQ ID NO: 3)
QVQLQQSGPGLVKPSQTLSLTCAIS<u>GDSVSSNSAA</u>WNWIRQSPSRGLEW

LG<u>RTYYRSKWYNDYAVSV</u>KSRITINPDTSKNQFSLQLNSVTPEDTAVYY

C<u>AREVTGDLEDAFDI</u>WGQGTMVTVSS*GGGGSGGGGSGGGGS*DIQMTQSP

SSLSASVGDRVTITCRAS<u>QTIWSY</u>LNWYQQRPGKAPNLLIY<u>AAS</u>SLQSG

VPSRFSGRGSGTDFTLTISSLQAEDFATYYC<u>QQSYSIPQT</u>FGQGTKLEI

K

HCDR1 = residues 26-35; HCDR2 = residues 53-61;

HCDR3 = residues 100-113; linker = residues 125-

139; LCDR1 = residues 166-171; LCDR2 = residues 189-191; and LCDR3 = residues 228-236.

m971-L7 VH domain
(SEQ ID NO: 4)
QVQLQQSGPGMVKPSQTLSLTCAIS<u>GDSVSSNSVA</u>WNWIRQSPSRGLEWL G<u>RTYYRSTWYNDYAVSM</u>KSRITINPDTNKNQFSLQLNSVTPEDTAVYYC<u>A</u>

<u>REVTGDLEDAFDI</u>WGQGTMVTVSS

CDR1 = residues 26-35; CDR2 = residues 53-61; and

CDR3 = residues 100-113 m971-L7 VL domain
(SEQ ID NO: 5)
DIQMIQSPSSLSASVGDRVTITCRAS<u>QTIWSY</u>LNWYRQRPGEAPNLLIY <u>AAS</u>SLQSGVPSRFSGRGSGTDFTLTISSLQAEDFATYYC<u>QQSYSIPQT</u>FGQ

GTKLEIK

CDR1 = residues 27-32; CDR2 = residues 50-52; and

CDR3 = residues 89-97 m971-L7 scFv
(SEQ ID NO: 6)
QVQLQQSGPGMVKPSQTLSLTCAIS<u>GDSVSSNSVA</u>WNWIRQSPSRGLEWL

G<u>RTYYRSTWYNDYAVSM</u>KSRITINPDTNKNQFSLQLNSVTPEDTANTYYC

<u>AREVTGDLEDAFDI</u>WGQGTMVTVSS*GGGGSGGGGSGGGGS*DIQMIQSPSS

LSASVGDRVTITCRAS<u>QTIWSY</u>LNWYRQRPGEAPNLLIY<u>AAS</u>SLQSGVPS

RFSGRGSGTDFTLTISSLQAEDFATYYC<u>QQSYSIPQT</u>FGQGTKLEIK

HCDR1 = residues 26-35; HCDR2 = residues 53-61; HCDR3 = residues 100-113; linker = residues 125-139; LCDR1 = residues 166-171; LCDR2 = residues 189-191; and LCDR3 = residues 228-236.

Measurement of CD22 scFv Affinity with Surface Plasmon Resonance

The binding affinity of m971 scFv and variants thereof to the CD22 extracellular domain (ECD) was measured on a BIAcore X100 instrument (GE Healthcare). Purified CD22 ECD-Fc fusion protein was diluted in 10 mM acetic acid buffer, pH 5.0, immobilized on a CM5 biosensor chip for 1400 RU using an amine coupling kit. The running buffer was HBS-EP (10 mM HEPES, pH 7.4, 150 mM NaCl, 3 mM EDTA, 0.05% surfactant P20). The scFvs diluted in running buffer were allowed to flow through the cells at concentrations 0.32, 1.6, 8, 40 and 200 nM. After a 10-minute of dissociation, the chip was regenerated with 10 mM acetic acid, pH 4.0, 0.5 M NaCl. The data were fitted with 1:1 binding model and the dissociation rate constant was estimated with the BIAevaluation software.

Western Blot

Leukemia cell protein extracts were prepared by lysing cells with RIPA buffer and heating at 98° C. for 5 minutes. The proteins were separated on an SDS-PAGE gel and transferred to a nitrocellulose membrane. The membranes were immunoblotted with antibodies PKC-βII and GAPDH (Abcam), overnight at 4° C. The blots were then incubated with the appropriate horseradish peroxidase-conjugated secondary antibodies for 1 hour at room temperature and visualized using a ChemiDoc™ XRS+ System (Bio-Rad Laboratories, Hercules, CA).

Immunofluorescent Staining

μ-dish 35 mm, high glass bottom dishes (Ibidi Inc, Madison, WI) were coated with poly-D-lysine for 2 hours and then seeded with $5 \times 10^5$ leukemia cells, which had been pre-treated with either 1 nM Bryostatin 1 or DMSO control for 24 hours. Approximately 12 hours after seeding, cells were fixed in 4% paraformaldehyde and then permeabilized with 0.2% Triton X-100 detergent. Cells were immunostained with a CD22-AF488 antibody (BioLegend) for 1 hour and then stained with DAPI for 15 minutes. Cells were then imaged using a Zeiss LSM880 confocal microscope equipped with a 63× plan-apochromat (N.A. 1.4) oil immersion objective lens, and T-PMT for differential interference contrast (DIC) imaging.

Generation of Human CD22 CAR T Cells

Lentiviral vectors encoding CD22-CAR were produced by transient transfection of 293T cells. Using Lipofectamine 3000 (Life Technologies), 293T cells were transfected with plasmids encoding packing and envelope vectors (pMDLg/pRRE, pMD.2G, pRSV-Rev, p3000), as well as a plasmid encoding the CD22-CAR. Viral supernatant was harvested from transfected cells at 24, 48 and 72 hours after transfection, spun for 10 minutes at 3000 RPM to remove cell debris, and frozen at −80° C. Human T cells were then thawed at $1 \times 10^6$/mL and activated for 48 hours in AIM-V media with 40 IU/mL IL-2 and a 3:1 ratio of CD3/CD28 microbeads (Life Technologies) per cell. T cells were then re-suspended at $2 \times 10^6$/mL in 10 mL lentiviral supernatant, 5 mL AIM-V, 100 IU IL-2, and 10 μg/mL protamine sulfate, and subsequently spun at 2000 g for 2 hours at 32° C. in 6-well plates. Plates were then incubated overnight at 37° C., and the process was repeated for a second day. After the second overnight incubation, CD3/CD28 microbeads were removed, T cells were re-suspended at $0.3 \times 10^6$/mL in AIM-V with 100 IU/mL IL-2, and were cultured for an additional 48-72 hours before use in experiments. After generation, T cells (both CAR and mock) were cultured in AIM-V medium supplemented with 5% heat-inactivated FBS, 100 U/mL penicillin, 100 U/mL streptomycin, 2 mM L-glutamine, 10 mM HEPES, and 100 IU/mL IL-2.

Nalm6 Xenograft and PDX In Vivo Studies

CD22-CAR functionality and anti-leukemic efficacy were evaluated in vivo in Nalm6 xenograft or PDX models with NOD.Cg-Prkdcscid Il2rgtm1Wjl/SzJ (NSG) mice (The Jackson Laboratory and bred in-house) ages 6-10 weeks. Mice received $1 \times 10^6$ GFP+ Luciferase+ tumor cells (Nalm6, or Nalm6 CRISPR variant, or PDX) intravenously on day 0. On day 3, mice received CD22-CAR-transduced T cells or mock-transduced T cells intravenously at the indicated quantity. To monitor leukemia burden, luciferin-D was injected into mice intraperitoneally and imaged using In Vivo Imaging System (IVIS) technology (Caliper Life Sciences). Bioluminescent signal flux (luminescence) for mice was measured using Living Image Version 4.1 Software (Caliper Life Science).

Bryostatin 1 Treatment

For all in vitro experiments and tumor/CAR pretreatment prior to intravenous injection, Bryostatin 1 was administered to cells at a concentration of 1 ng/mL. Dimethyl sulfoxide (DMSO) vehicle control was administered to control-treated cells at an equal volume. Prior to co-culture or intravenous injection, Bryostatin 1- and DMSO-treated cells were washed 3x in sterile PBS. For all in vivo experiments, Bryostatin 1 was diluted in PBS and administered via intraperitoneal injection at a dose of 40 μg/kg (1 μg/25 g mouse). For control-treated groups, an equal volume of DMSO was diluted in PBS and administered in the same manner RNA Sequencing and Data Analysis Sixteen RNA-seq samples were pooled and sequenced on one NextSeq high output run using Illumina TruSeq Poly A RNA Kit v3 with paired end sequencing. All samples had greater than 30 million pass filter reads with a base call quality above 95% of bases with Q30 and above. Reads of the samples were trimmed for adapters and low-quality bases using Trimmomatic software before alignment with the reference genome Human—hg19 and the annotated transcripts using STAR. The mapping quality statistics were calculated using Picard software and library complexity was measured in terms of unique fragments in the mapped reads using Picard's MarkDuplicate utility. The Partek Flow informatics pipeline was used to generate fold change and differentially expressed gene data as well as for data visualization. Gene set enrichment analysis (GSEA) of the differentially expressed genes was performed as previously described and using standard parameters.

Flow Cytometry

FACS analysis of cell surface CAR and protein expression was performed using an LSR II Fortessa flow cytometer (BD Biosciences). CD22-CAR was detected by incubation with 22-Fc (R&D Systems), followed by incubation with human IgG-specific PE-F(ab)2 (Thermo Fisher Scientific). The following human monoclonal antibodies were used for detection of cell surface proteins: CD22-APC, CD22-PE, CD19-Pacific Blue, CD45-PerCP/Cy5.5, CD3-APC/Cy7, PD1-PE/Cy7, LAG3-APC, TIM3-Pacific Blue, CD8-APC, CD8-PE/Cy7, CD45RA-APC, CD45RO-PE/Cy7, CCR7-Pacific Blue, CD4-Pacific Blue, CD69-APC (all from BioLegend). CD22 site density was determined using QuantiBrite-PE beads (BD Biosciences) using methods previously described (Jasper et al., *Cytometry B Clin Cytom* 80(2):83-90, 2011). Dead cells were identified using eFluor 506 fixable viability dye (Thermo Fisher Scientific). GFP-expressing leukemia cells were identified through the FITC channel.

In Vitro Cytokine and Leukemia Clearance Assays

For cytokine production assays, CAR or mock T cells were washed to remove IL-2 and re-suspended in RPMI medium. $1 \times 10^5$ effector cells were then co-cultured with tumor cells in RPMI at a 1:1 effector to target ratio in 96-well plates and incubated at 37° C. for 20 hours. The plates were spun at 1200 RPM for 6 minutes to pellet the cells, and cytokine concentrations in the culture supernatants were measured using IL-2 ELISA (R&D systems), IFNγ ELISA (R&D systems), or granzyme B ELISA (Thermo Fisher Scientific) kits according to the manufacturer's directions. For leukemia clearance assays, $1 \times 10^5$ CAR or mock T cells were co-cultured with tumor cells in RPMI at a 1:1 effector to target ratio in 96-well plates. After initiation of co-culture, plates were incubated in an IncuCyte ZOOM and imaged for green object confluence (indicating GFP positive leukemia confluence) every 3-6 hours for up to 40 hours.

Statistical Analysis

Significance of ELISA results were calculated using the Student's unpaired t-test. Significance of CAR protein expression changes in bone marrow, spleen, and peripheral blood was calculated using the Mann-Whitney test unless indicated otherwise.

Example 2: Affinity Matured Anti-CD22 Monoclonal Antibody

This example describes an evaluation of the impact of antigen site density on CAR functionality and the potential to enhance CAR T cell efficacy through increasing site density using a therapeutic agent previously shown to up-regulate CD22 expression in chronic lymphocytic leukemia (CLL) (Viola Biberacher et al., *Haematologica*. 2012; 97(5): 771-779). In addition to identifying reduced CAR T cell activity in response to leukemia expressing lower antigen density, the data disclosed herein also demonstrates shortened CAR T cell persistence and differences in CAR T cell phenotype following in vivo exposure to leukemia with lower antigen site density. Bryostatin 1, a natural product originally isolated from the marine bryozoan *Bugula neritina* (George et al., *J Am Chem Soc.* 1982; 104(24):6846-6848), increases CD22 expression on pre-B ALL and diffuse large B cell lymphoma (DLBCL), improves anti-leukemia CAR T cell response, memory formation, and durability of response. This the first report to provide a clinically feasible and relevant approach to enhance the efficacy of CART therapy through target antigen modulation.

Figure 1C:
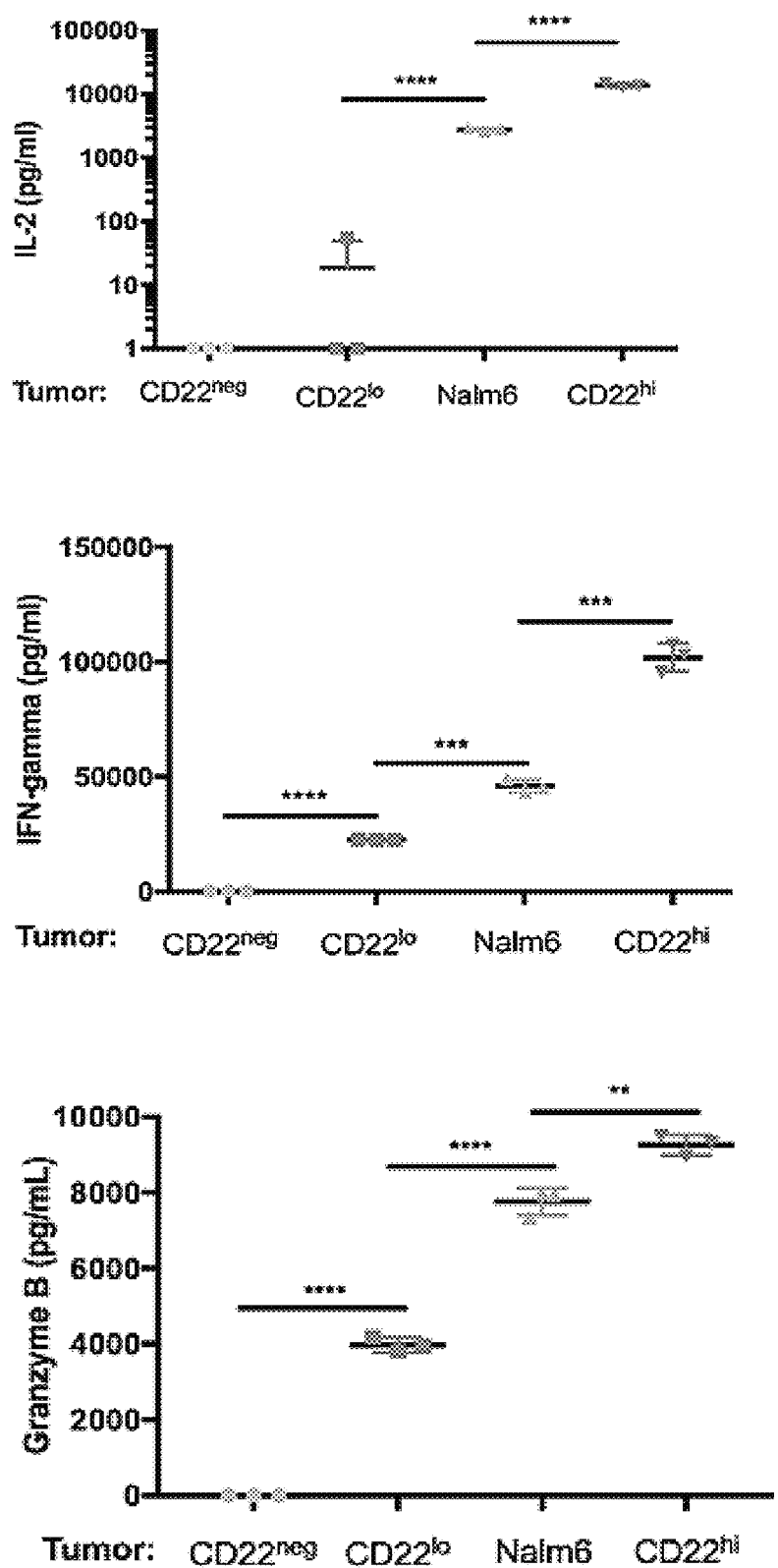
Figure 7A:
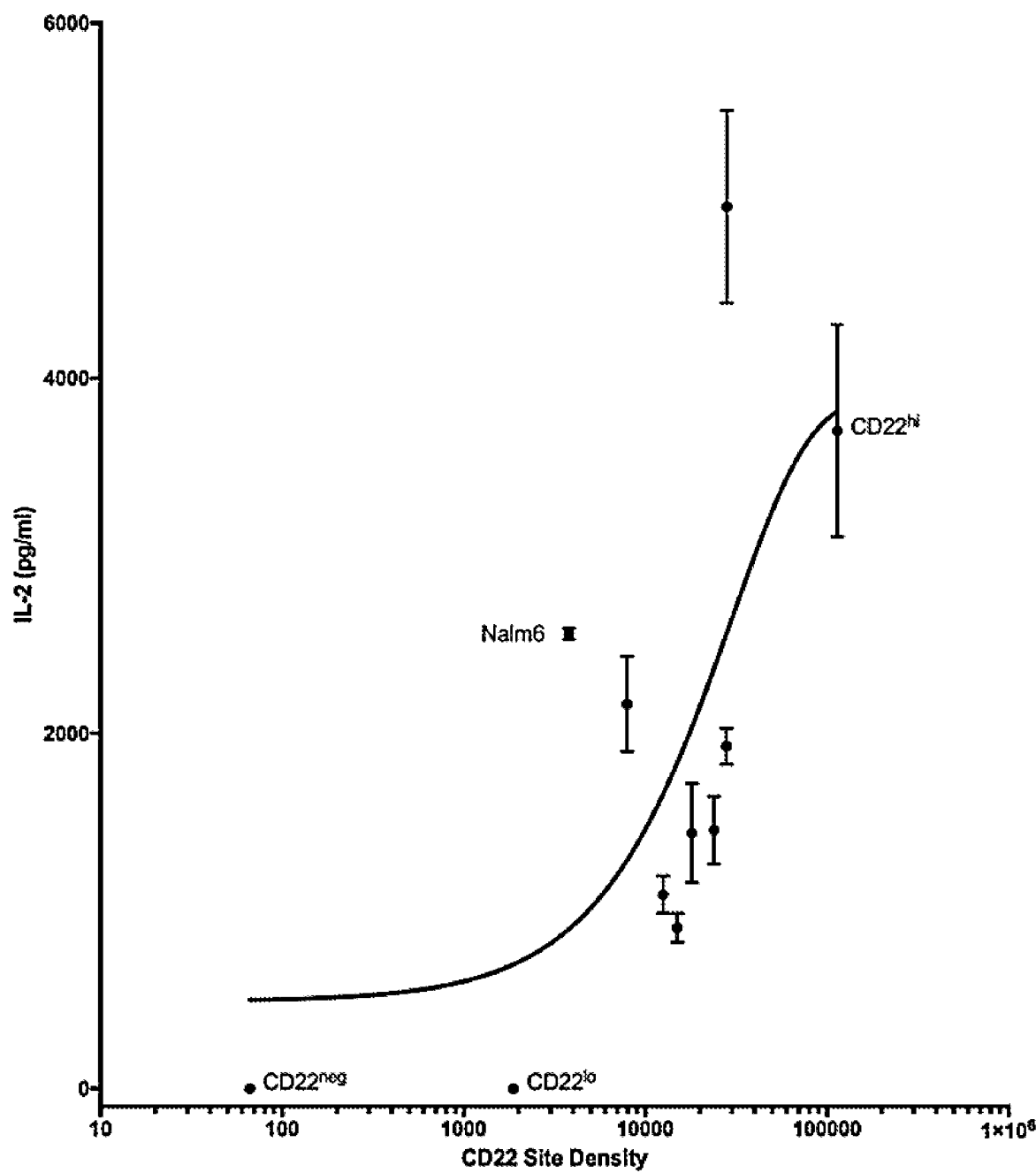
Figure 8:
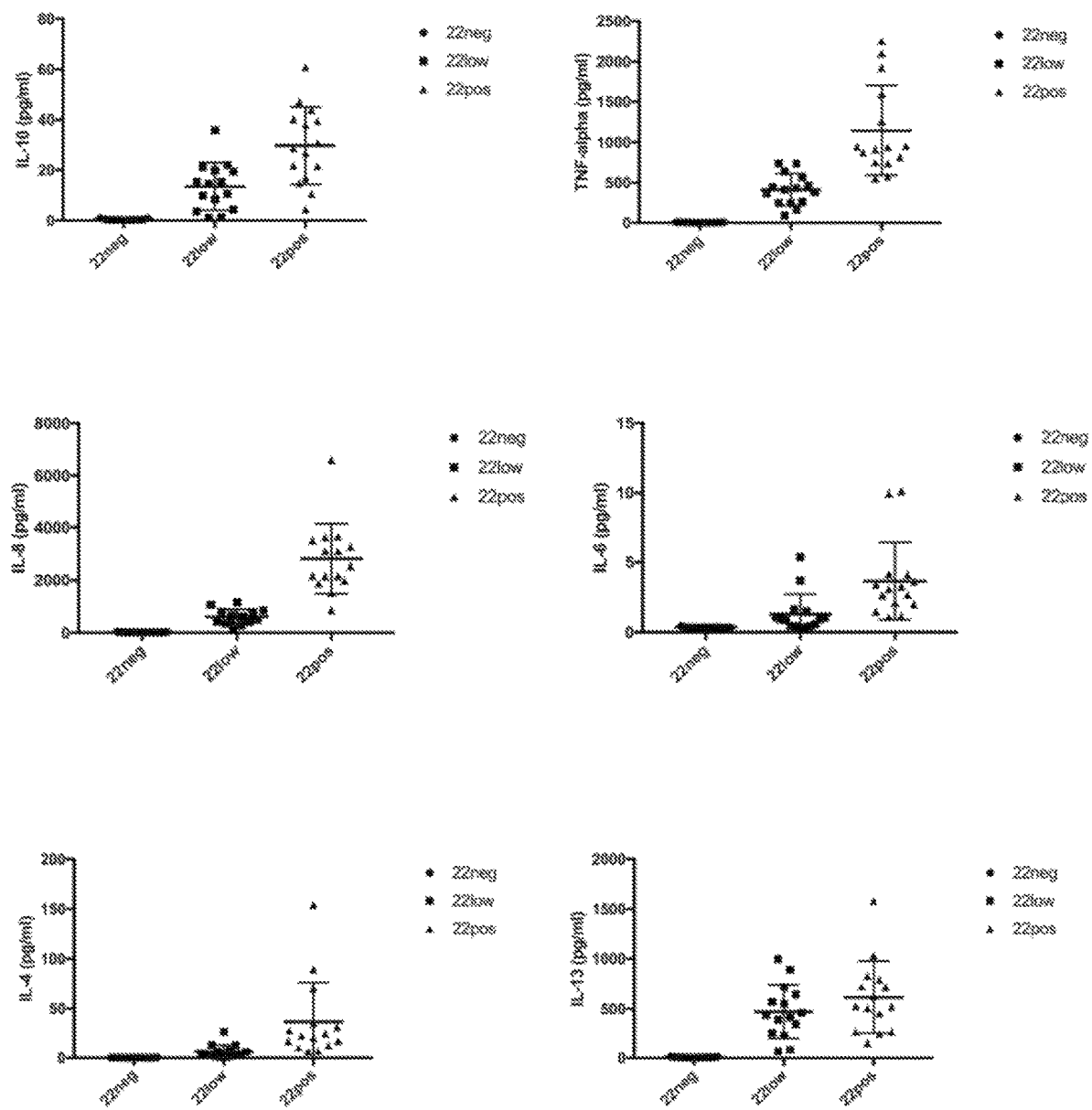
FIG. 8: Tumor cells ($1\times10^5$) were co-cultured with $1\times10^5$ CD22 CAR T cells from CD22 CART patient samples for 18 hours. Supernatant was evaluated by Meso Scale Multiplex pro-inflammatory cytokine panel.

Decreased CD22 Site Density on Pre-B Cell ALL Impacts CD22-Directed CAR T Cell Functionality Evaluation of patient samples from the CD19 and CD22 CART trial showed that baseline CD22 site density was statistically lower than CD19 site density (3079 vs 10450 molecules/cell, FIG. 1A) on primary human pre-B ALL. Furthermore, in patients relapsing after CD22 CART there was a significant decline in CD22 site density compared to baseline (FIG. 7A). Additionally, initial CD22 site density also correlated with changes in CD22 CART expansion. Some patients with lower site density had decreased CAR expansion and subsequent limited ability to clear leukemia (FIG. 1C). To determine whether CD22 site density directly impacts CAR function, Nalm6 ALL cell lines expressing varying amounts of CD22 were generated using CRISPR/Cas 9 gene editing as described in Example 1 (CD22-negative ($CD22^{neg}$), CD22-low ($CD22^{lo}$) and CD22-high ($CD22^{hi}$)) (FIG. 7A) (Fry et al., *Nat Med.* 2018; 24(1):20-28). IFN-γ and IL-2 production by healthy, donor-derived CD22 CAR T cells incrementally decreased in response to Nalm6 expressing lower CD22 antigen site density (FIG. 1D). Moreover, cytotoxicity, as assessed in vitro by granzyme B production, also decreased upon exposure to ALL with lower CD22 site density (FIG. 1D). Finally, in order to account for donor variability on CAR T cell functionality, CD22 CAR T cells from 17 patients enrolled in the CD22 CART trial were assessed and a similar gradation of IL-2 production in response to target cells expressing varying site densities was observed (FIG. 1E). There was a consistent trend of decreased production of a variety of other T cell activation cytokines by CD22 CAR T cells in response to decreasing site density cell lines (FIG. 8).

Figure 1F:
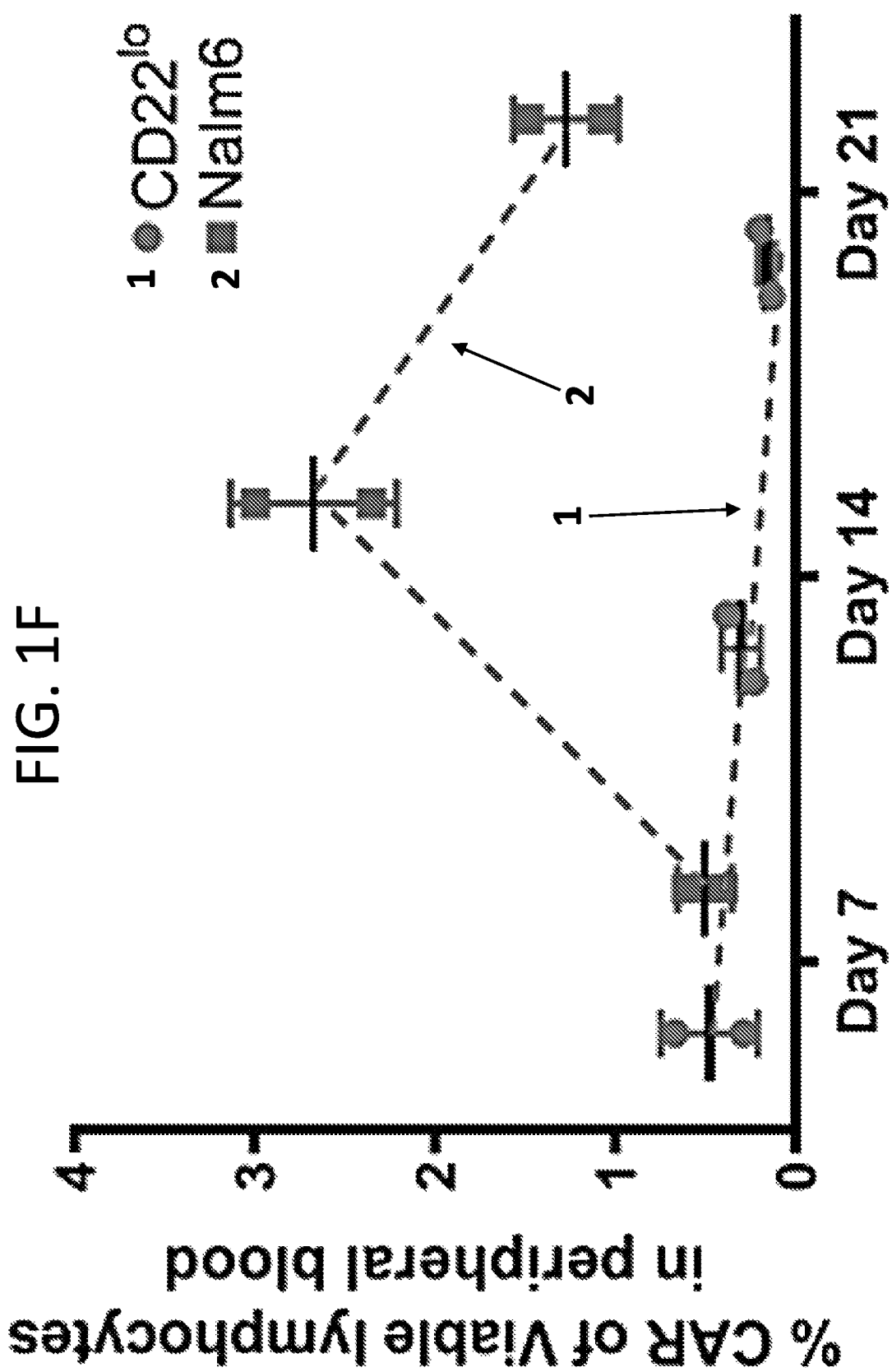
Figure 2A:
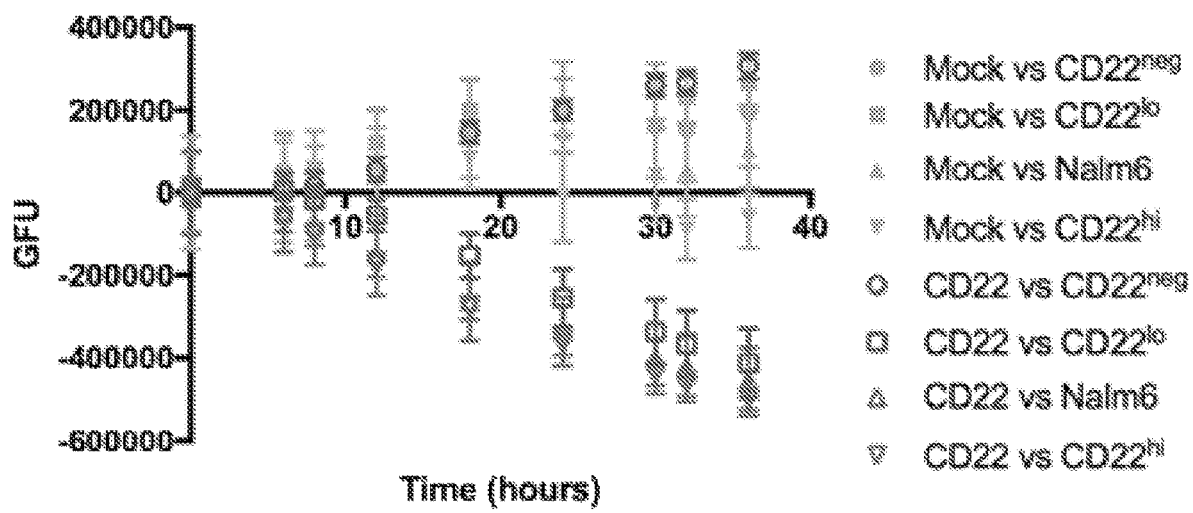
Figure 2B:
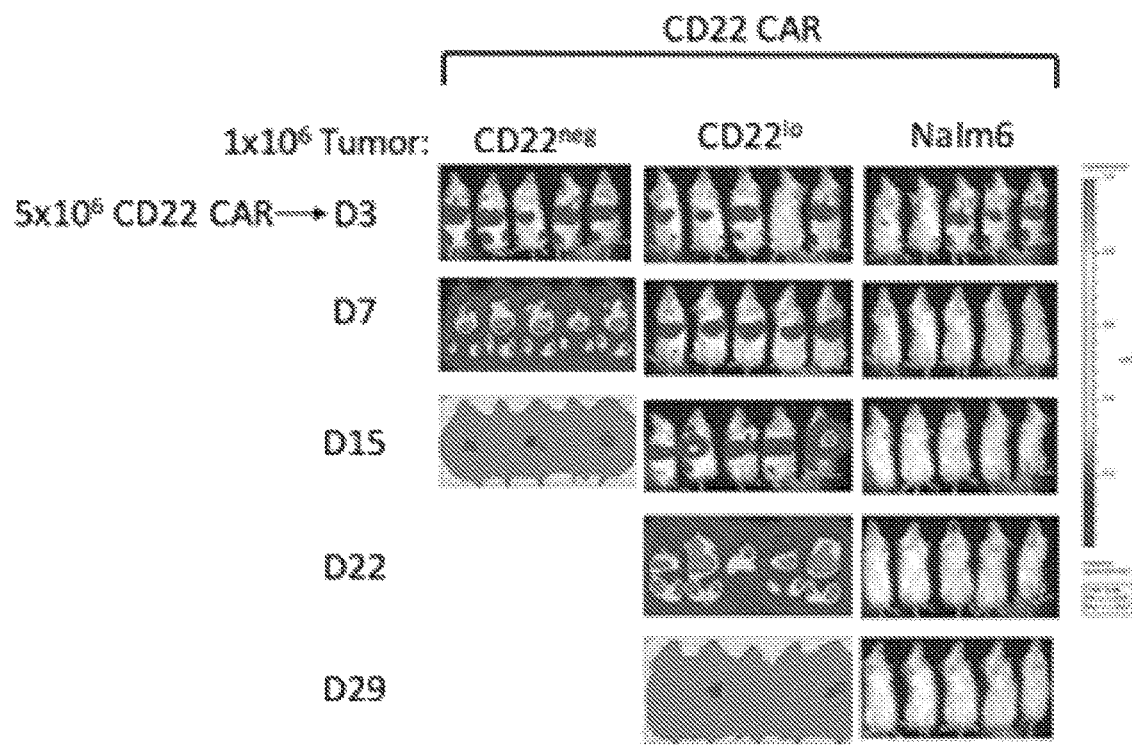
Figure 2C:
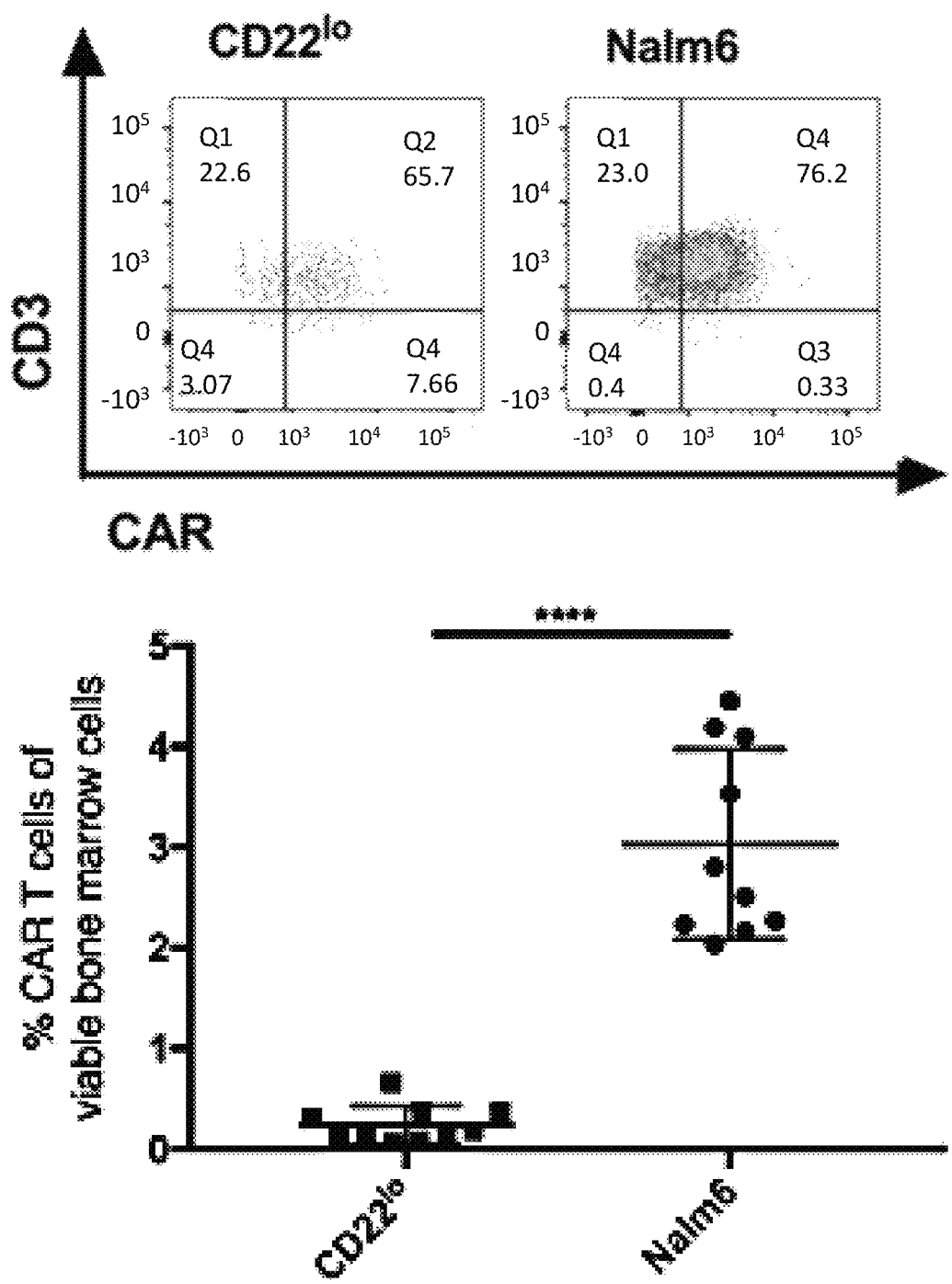

Site Density Affects In Vivo CD22 CAR T Efficacy, Persistence, and Memory Phenotype Although site density did not affect CAR T cell-mediated depletion of ALL in vitro (FIG. 2A), CD22 CAR is unable to clear $CD22^{lo}$ ALL in vivo (FIG. 2B). Moreover, eradication of $CD22^{lo}$ ALL was not rescued by increased dose of CD22 CART (FIG. 1E). Diminished ability for CD22 CART to clear $CD22^{lo}$ ALL was associated with poor early expansion of CART (FIG. 1F), consistent with observations in patients treated with the CD22 CART (FIG. 1B). Based on the delayed progression of $CD22^{lo}$ ALL in the presence of CAR T cells, it was hypothesized that site density may impact CAR T cell persistence and/or phenotype. Indeed, at day 16 after CAR injection, CD22 CAR cells were significantly reduced in the bone marrow of $CD22^{lo}$ leukemia-bearing mice as compared to parental Nalm6-bearing mice (FIG. 2C, p<0.0001).

Figure 2E:
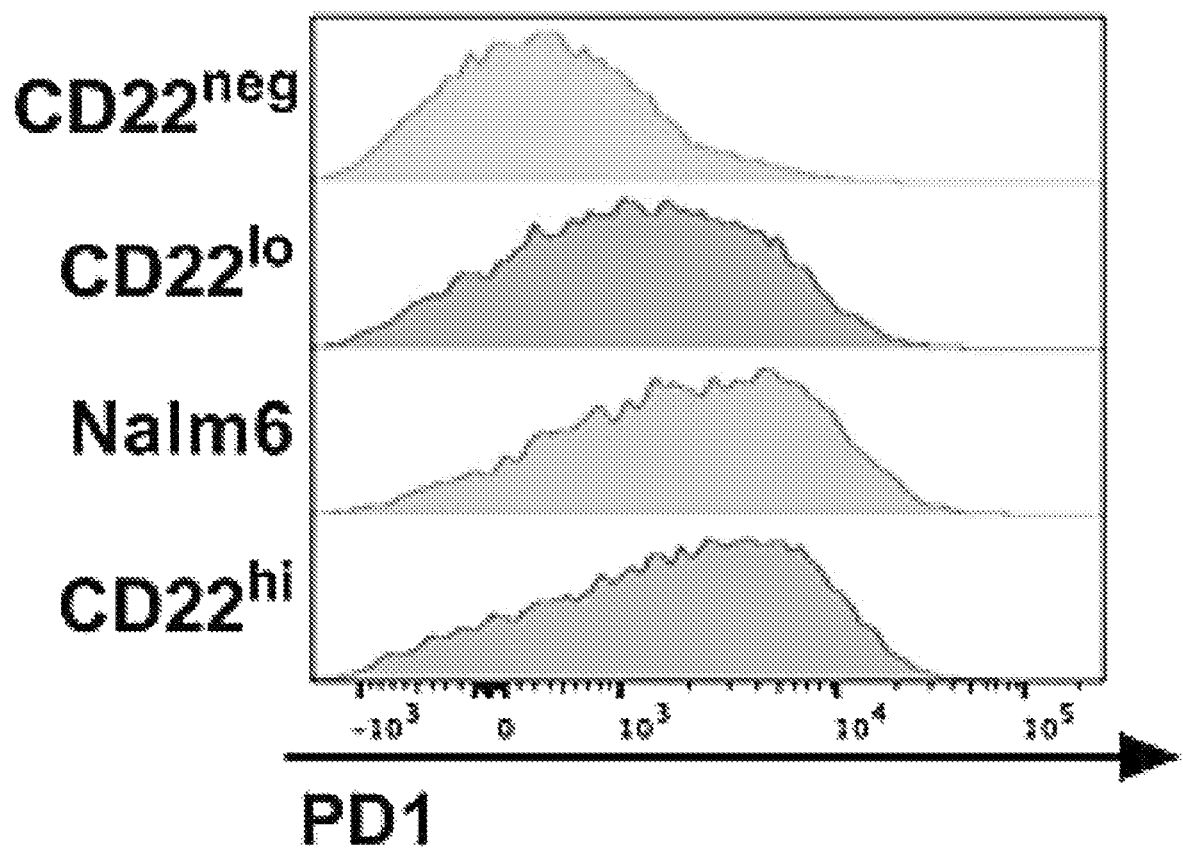

The impact of site density on the activation of CART during initial expansion was next assessed. PD1 expression on CART was reduced by 30% after 24 hours of in vitro co-culture with $CD22^{lo}$ ALL compared with parental Nalm6 (FIG. 2E). Following 8 days of in vitro co-culture, $CD22^{lo}$-exposed CARs had a higher percentage of naïve cells ($CCR7^+$ and $CD45RA^+$) compared with Nalm6-exposed CARs (FIG. 2F). Although there was no difference in PD1 expression at day 16, by day 30, there was a trend toward increased PD1 expression in the Nalm6-bearing group as compared to the $CD22^{lo}$ leukemia group (FIG. 2D). Furthermore, CAR exposure to $CD22^{lo}$ leukemia cells resulted in a trend toward less central and effector memory cells compared to the Nalm6 exposure (FIG. 2E). This combined in vitro and in vivo data indicates that in the presence of low antigen density, CART may not be able to convert a memory phenotype, thereby resulting in decreased durability of response in vivo.

Figure 9B:
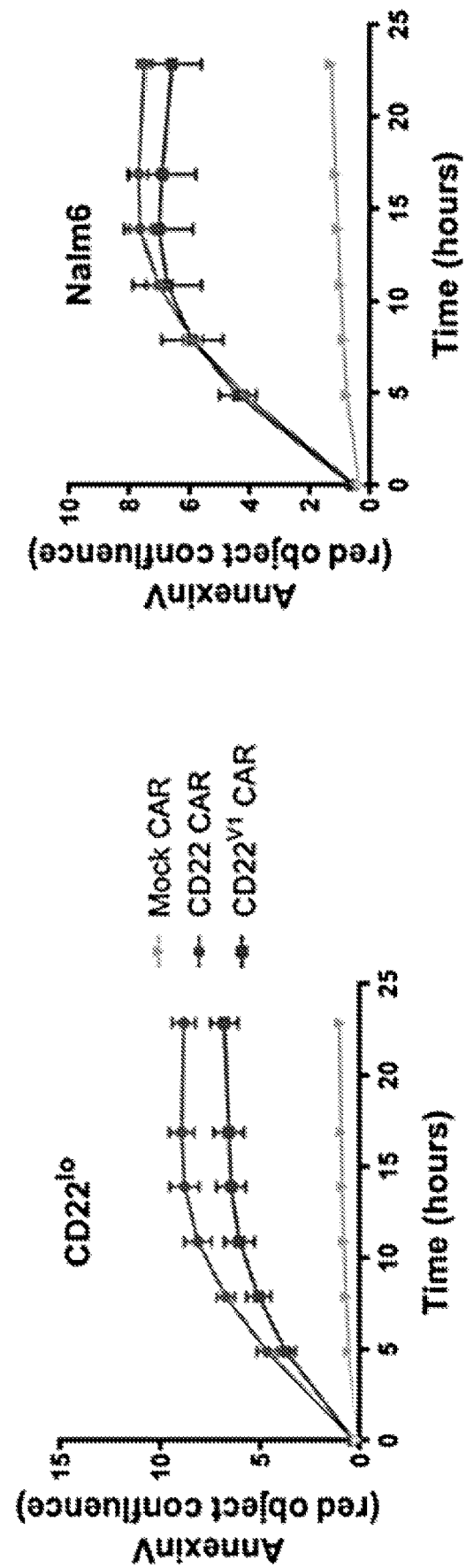
Figure 9C:
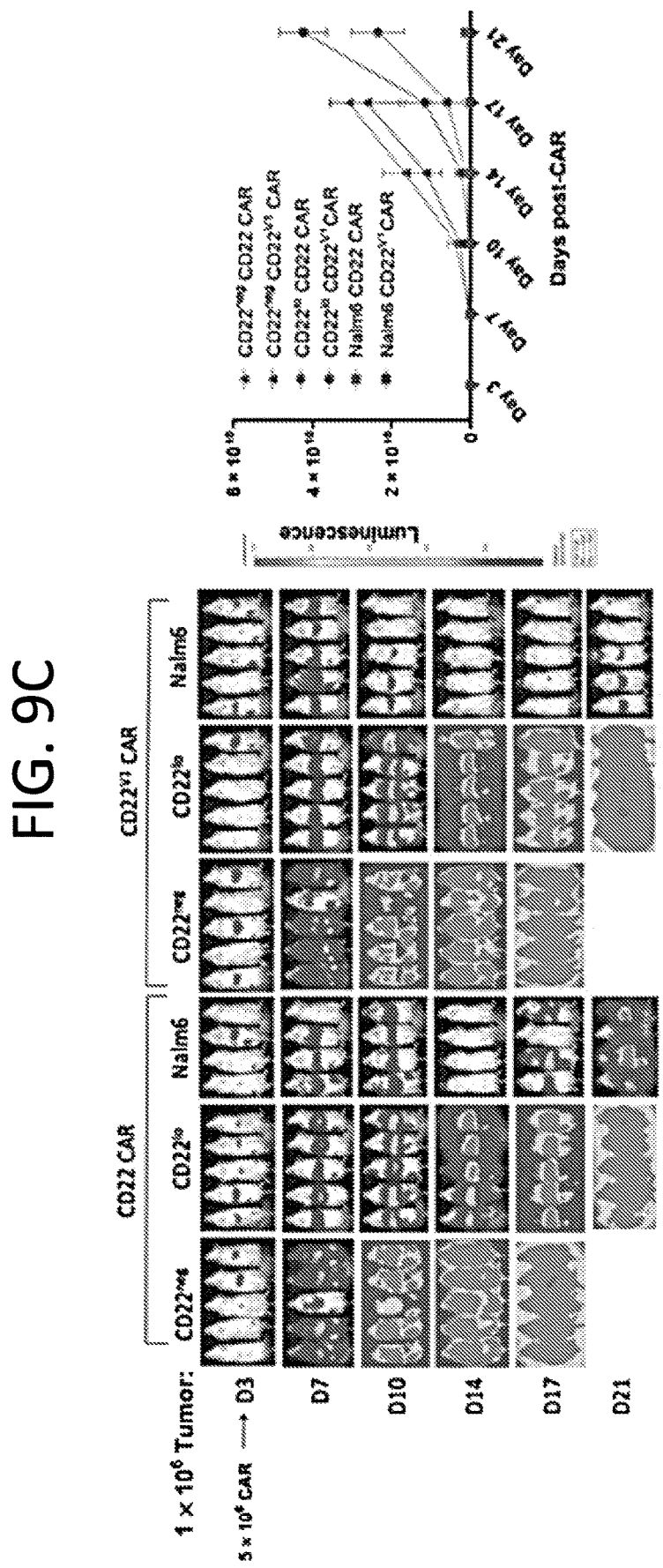
Figure 9D:
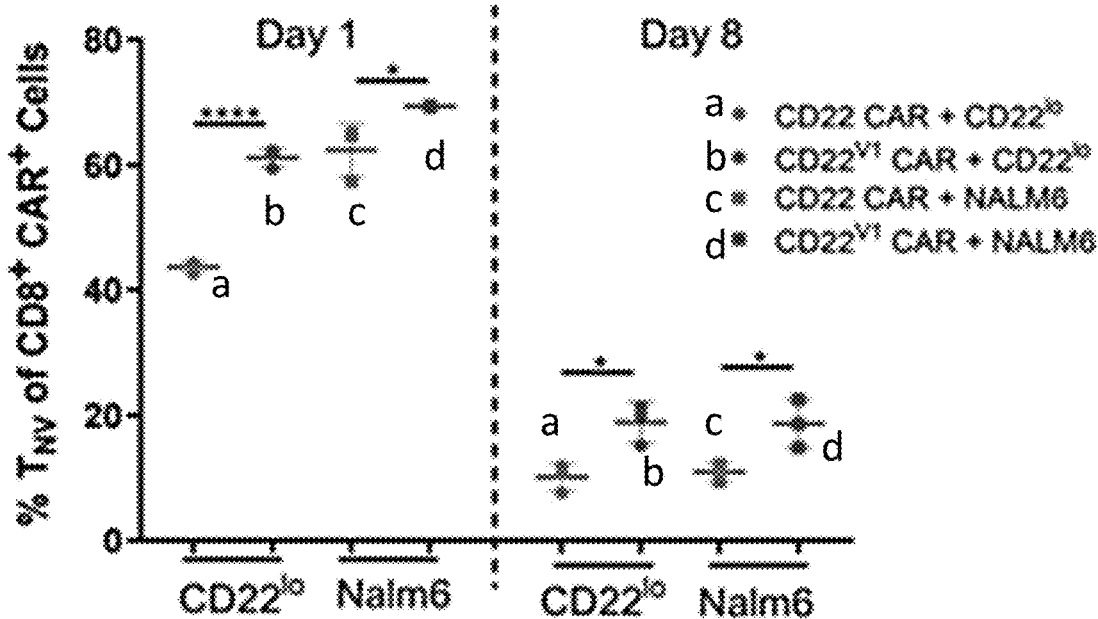
Figure 9E:
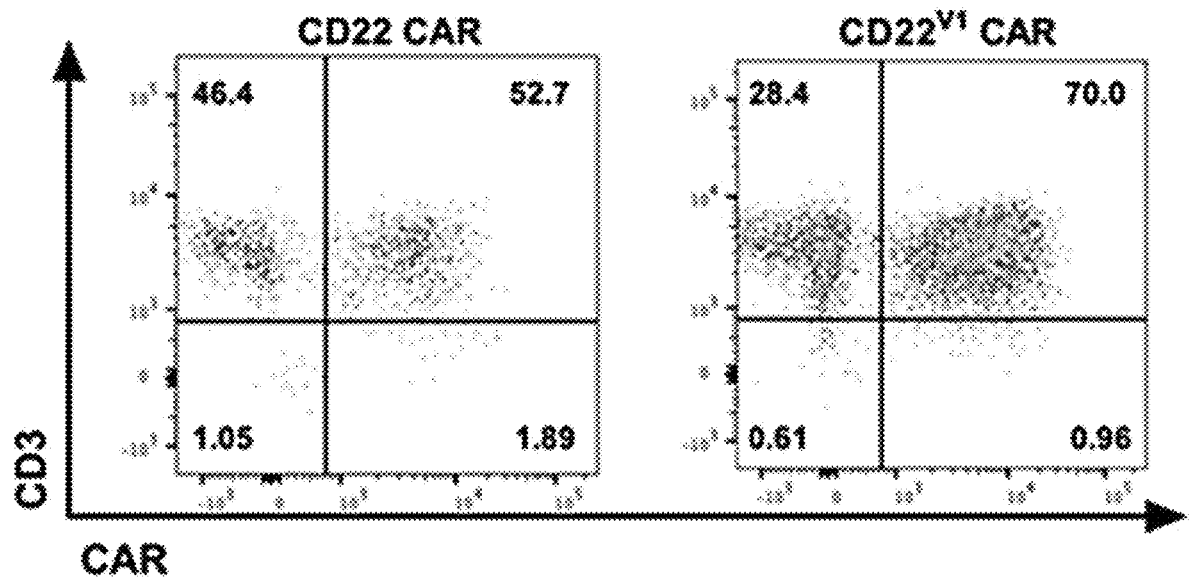
Figure 9F:
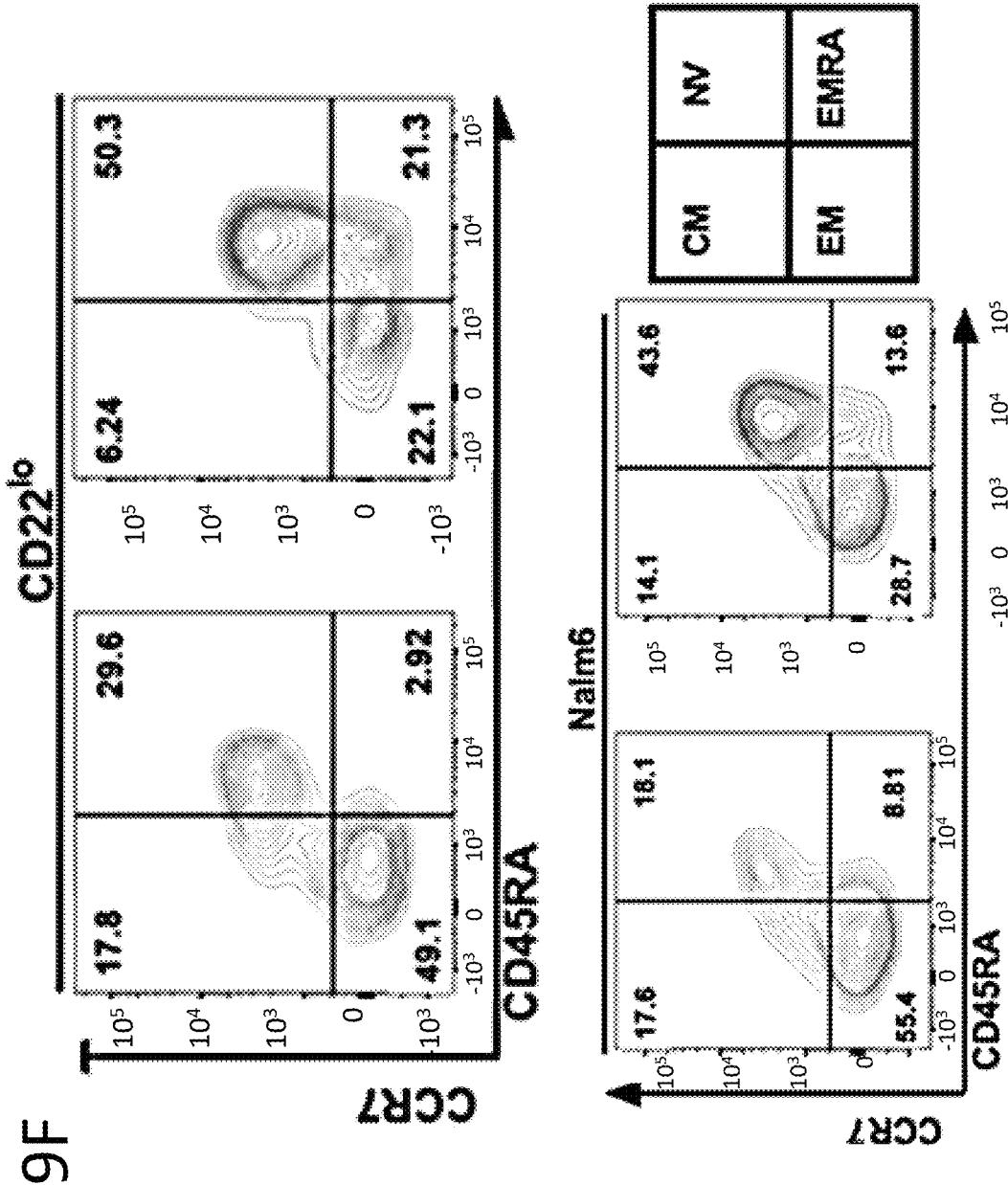
Figure 13A:
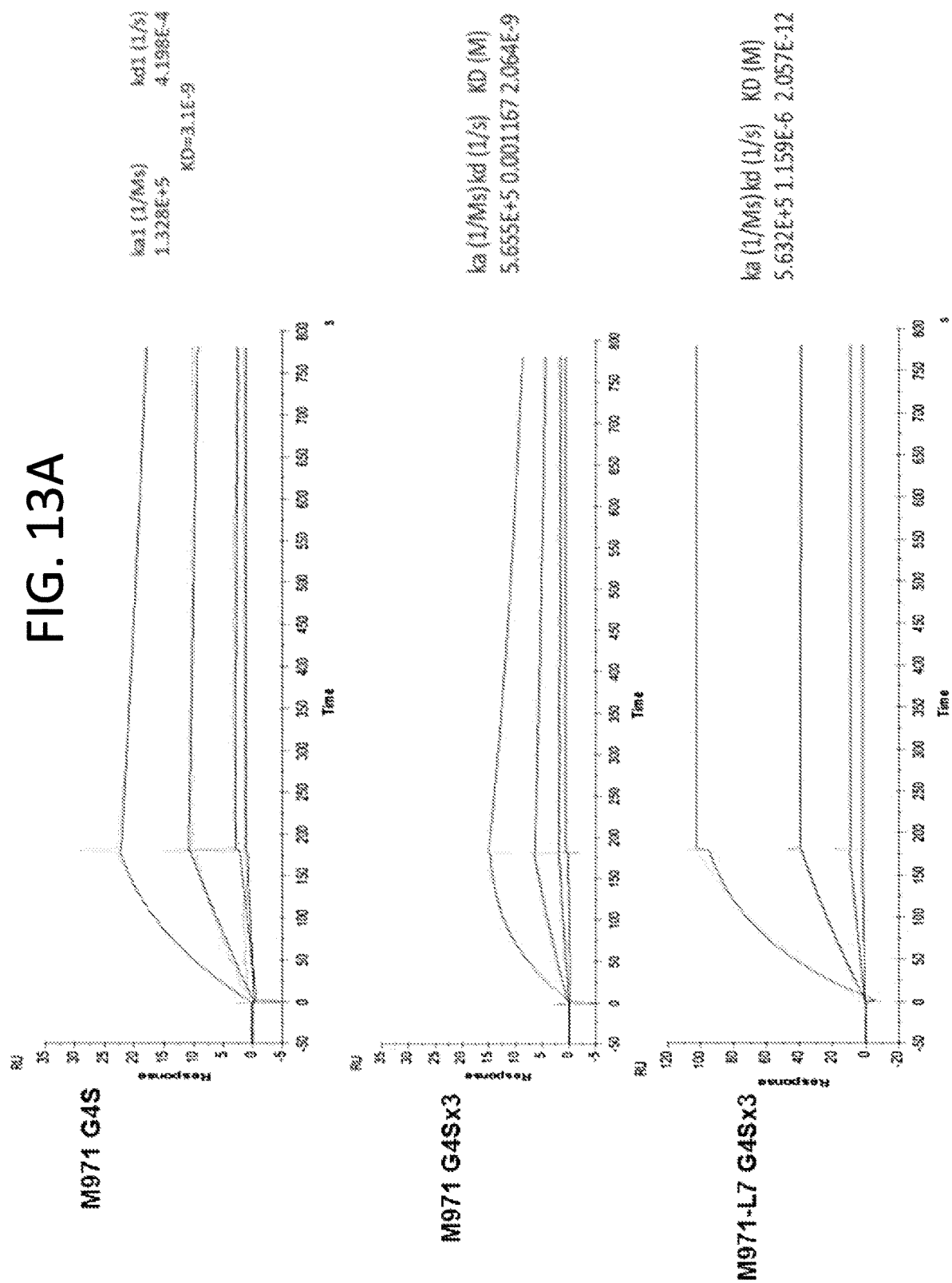
Figure 13B:
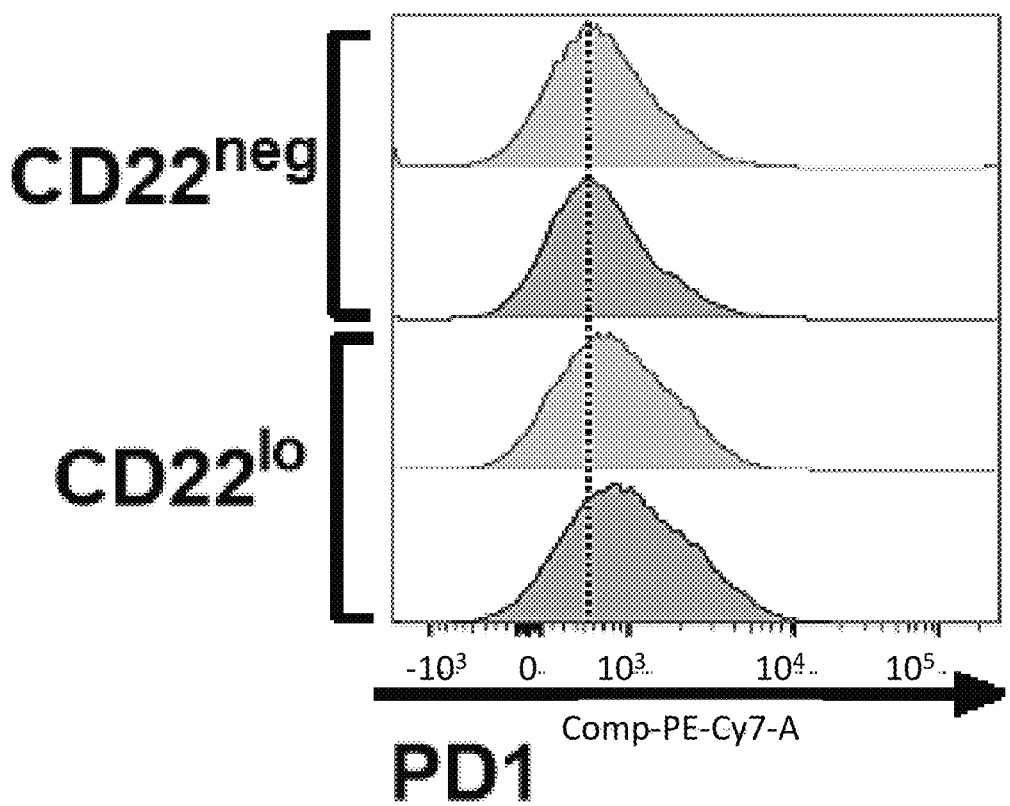
Figure 13C:
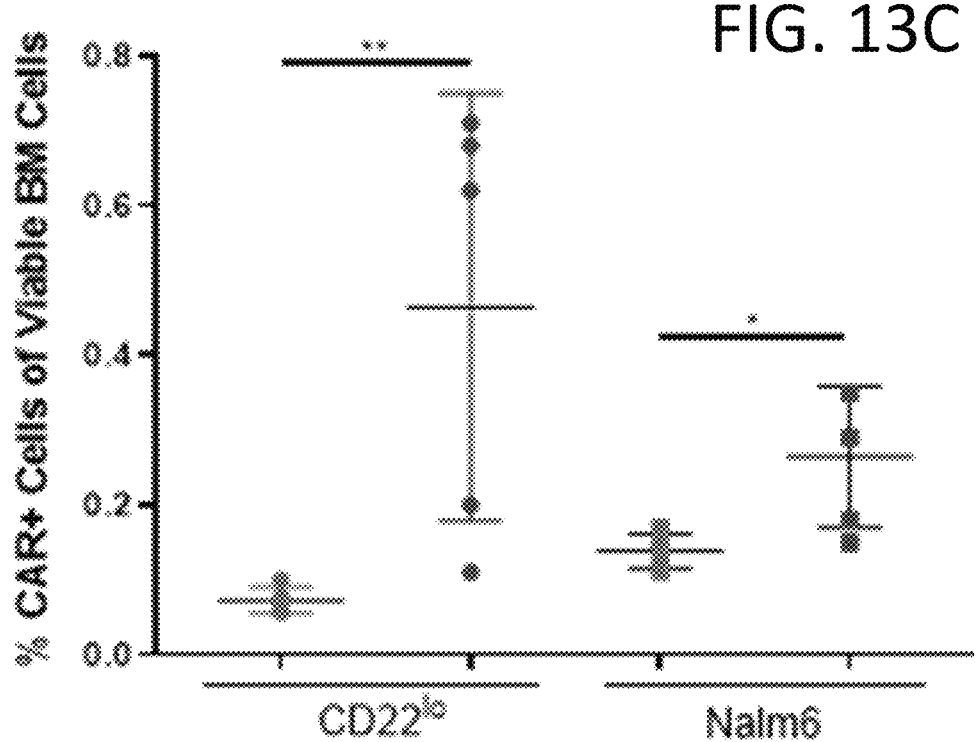
Figure 13E:
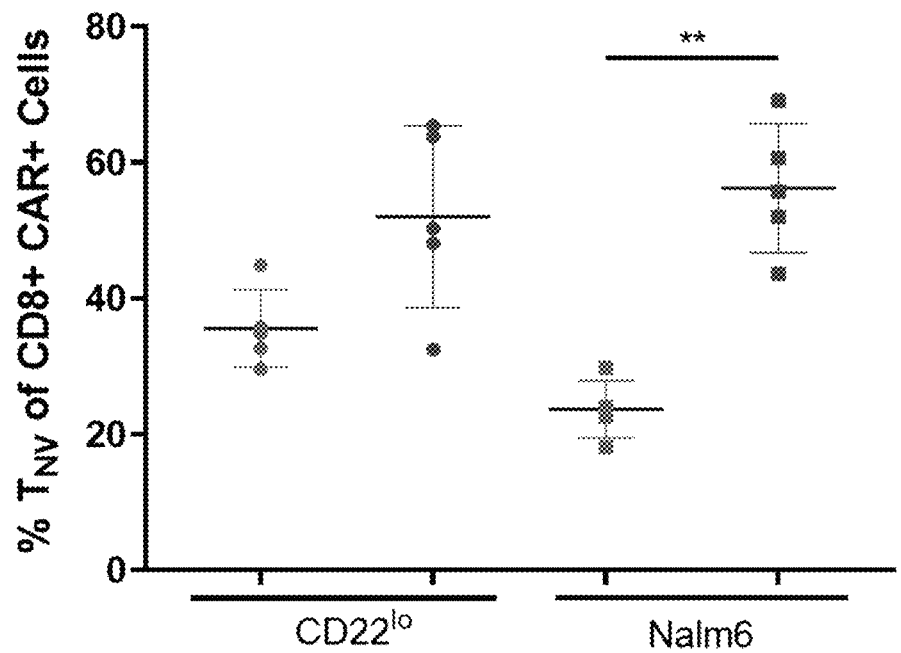
Figure 13F:
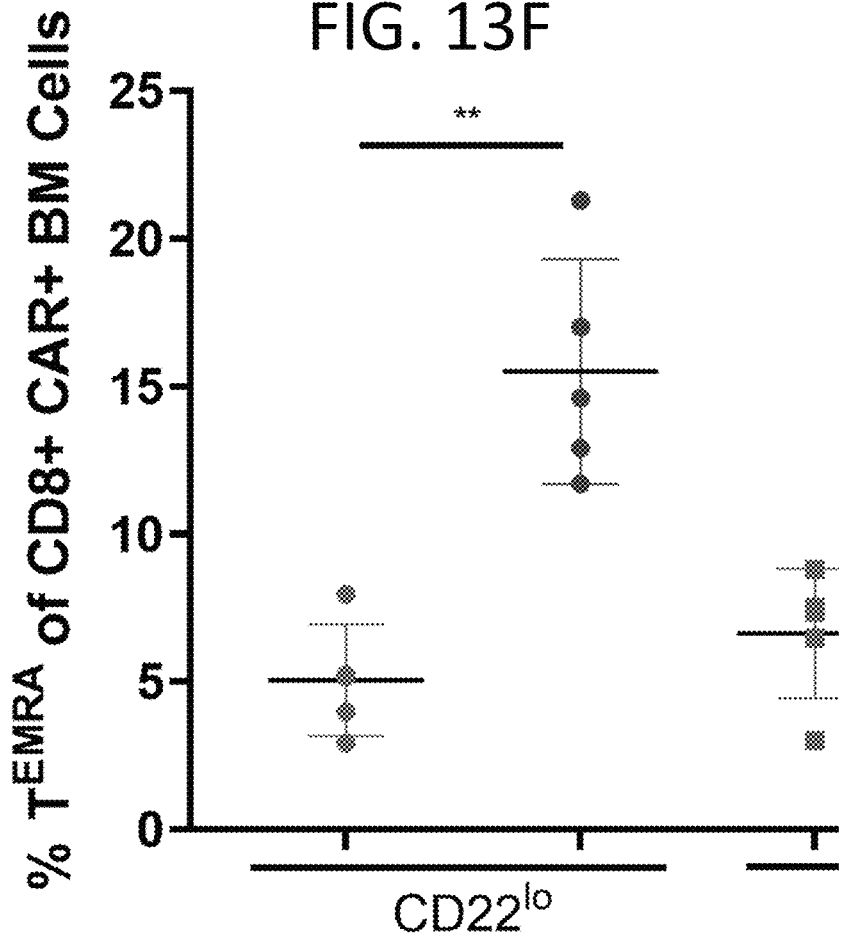

Increased CAR Affinity Did not Improve CAR Sensitivity to Low Site Density Leukemia The CD22-specific scFv (m971) used in the construction of the CD22 CAR has a relatively low binding affinity (Haso et al., *Blood.* 2013; 121(7):1165-1174; Xiao et al., MAbs 1:297-303, 2009). Thus, the anti-CD22 scFv (m971-L7) was modified to generate a higher affinity CD22 CAR ($CD22^{V1}$ CAR; FIG. 13A) with improved binding at lower antigen densities, while maintaining the same 41BB costimulatory domain. However, this scFv modification did not enhance in vitro cytokine production or cytotoxicity (FIGS. 9A-9B). Furthermore, the $CD22^{V1}$ CAR did not improve clearance of $CD22^{lo}$ leukemia cells in xenografts (FIG. 9C). To evaluate the cause of this lack of enhanced activity in vitro, T cells expressing the CD22$^{V1}$ CAR were evaluated for persistence, activation, exhaustion, and memory phenotype both in vitro and in vivo. One day after co-culture with CD22$^{lo}$ leukemia, the CD22$^{V1}$ CAR had similar PD1 expression as the original CAR (FIG. 13B). However, both on day 1 and day 8 of in vitro co-culture, a higher percentage of CD22$^{V1}$ CART remained naïve compared with the original CD22 CAR (FIG. 9D). CD22$^{V1}$ CART persisted in the presence of CD22$^{lo}$ leukemia in vivo at day 16 (FIG. 9E), with similar expression of PD1, TIM3, and LAGS compared with the original CAR (FIG. 13C). Similar to the in vitro findings, a higher percentage of CD22$^{V1}$ CART remained naïve as compared with the original CD22 CAR when responding to both CD22$^{lo}$ and parental Nalm6 leukemia (FIG. 9F; FIG. 13E). Finally, a population of EMRA CART (CCR7$^-$, CD45RA$^+$), consistent with terminal differentiation, emerged in the CD22$^{V1}$ CAR, that was not present in the original CD22 CAR and that was more pronounced when targeting CD22$^{lo}$ leukemia (FIG. 9F; FIG. 13F).

Bryostatin 1 Increases CD22 Antigen Expression in ALL and DLBCL Cell Lines

Figure 3A:
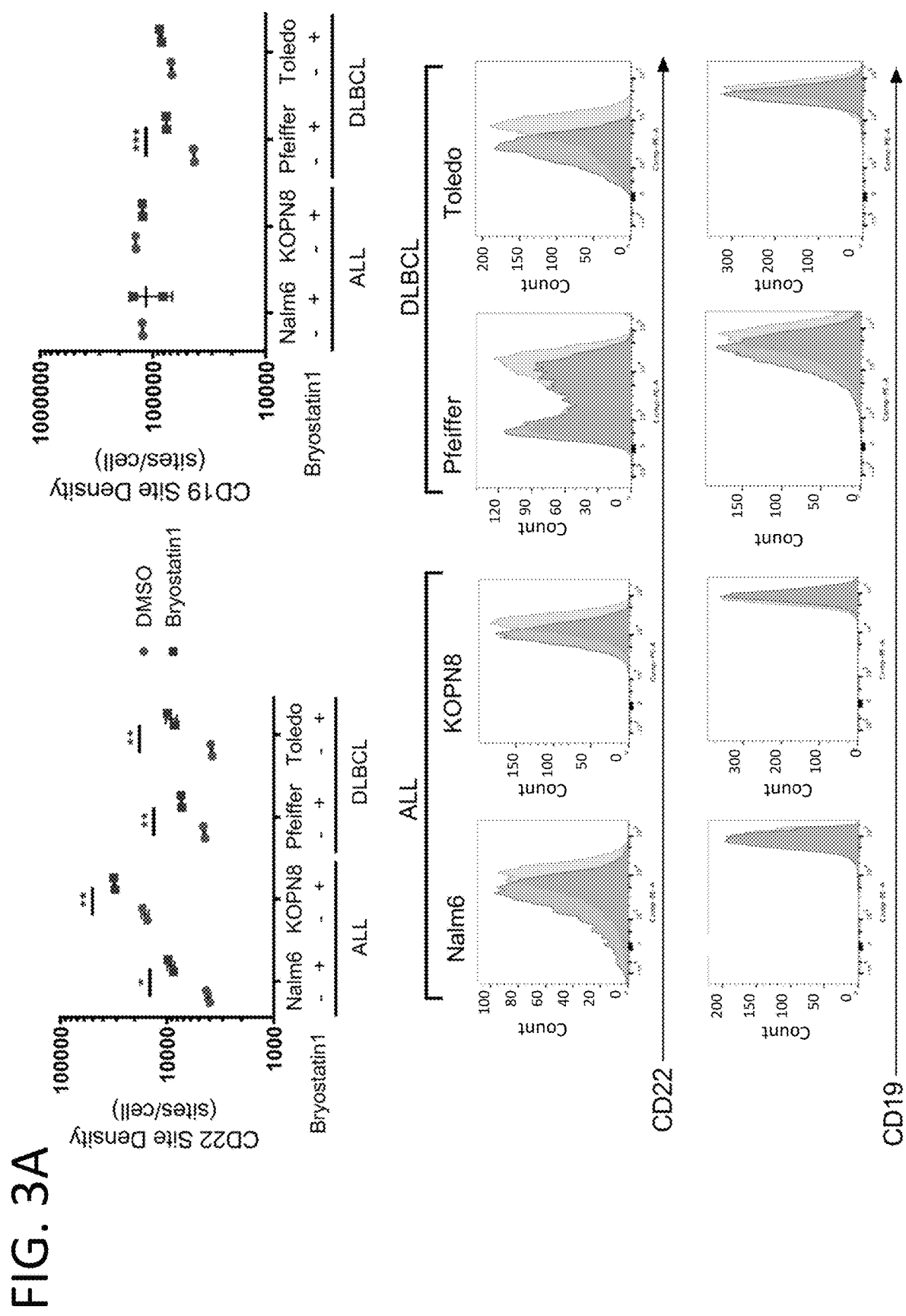
FIGS. 3A-3D.
Figure 3B:
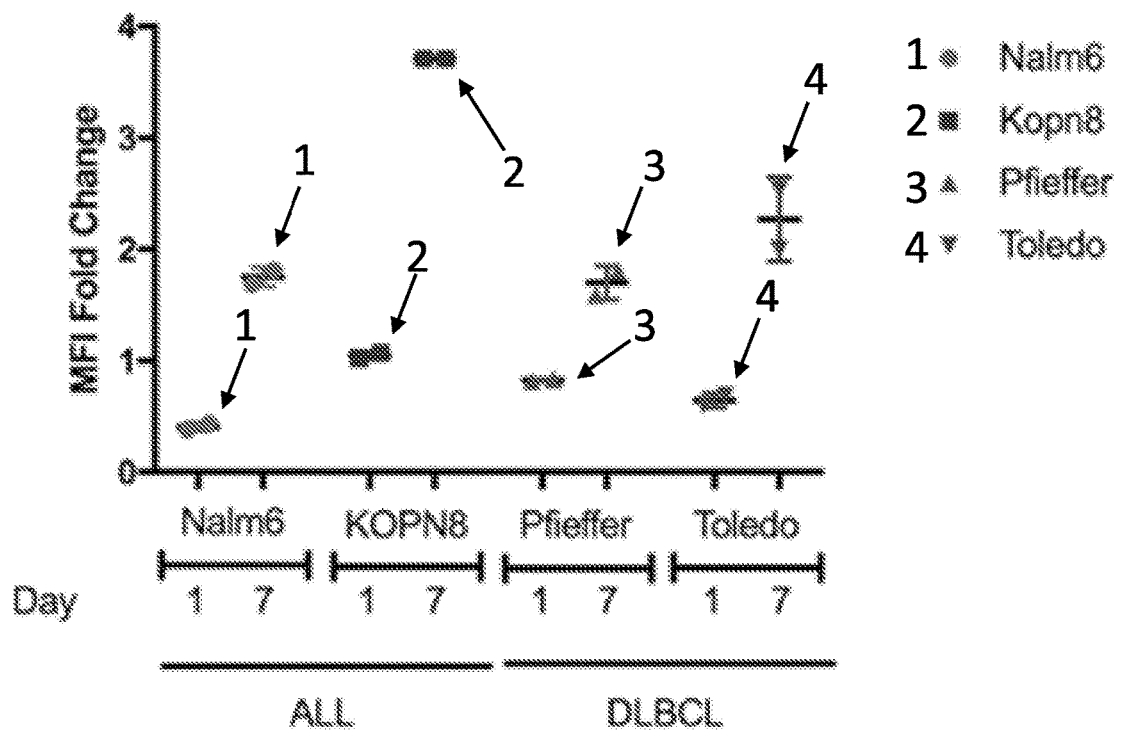
Figure 3C:
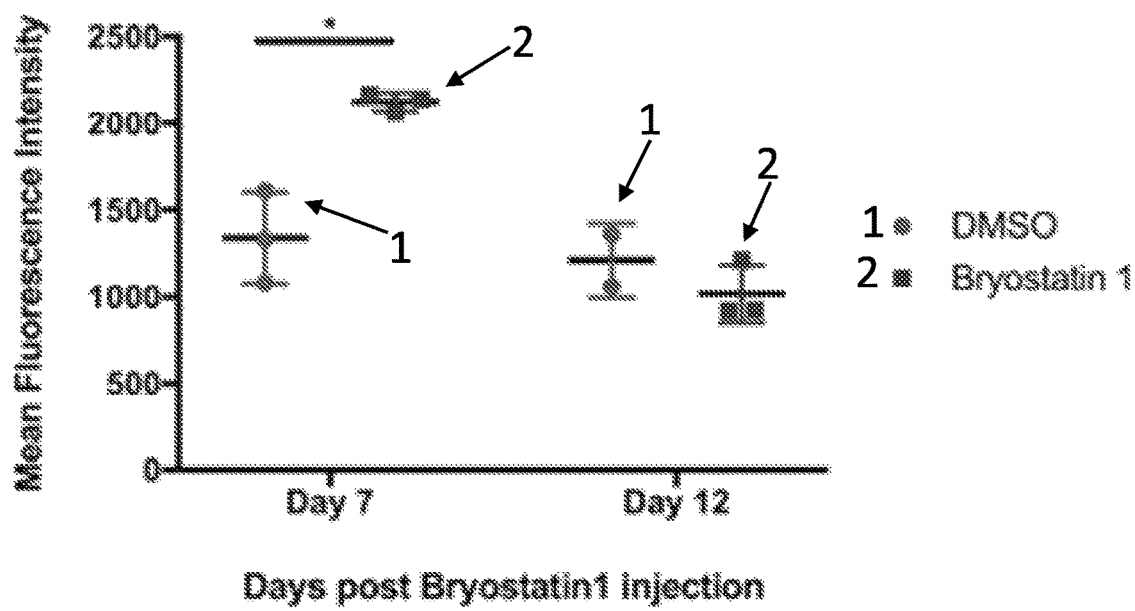
Figure 3D:
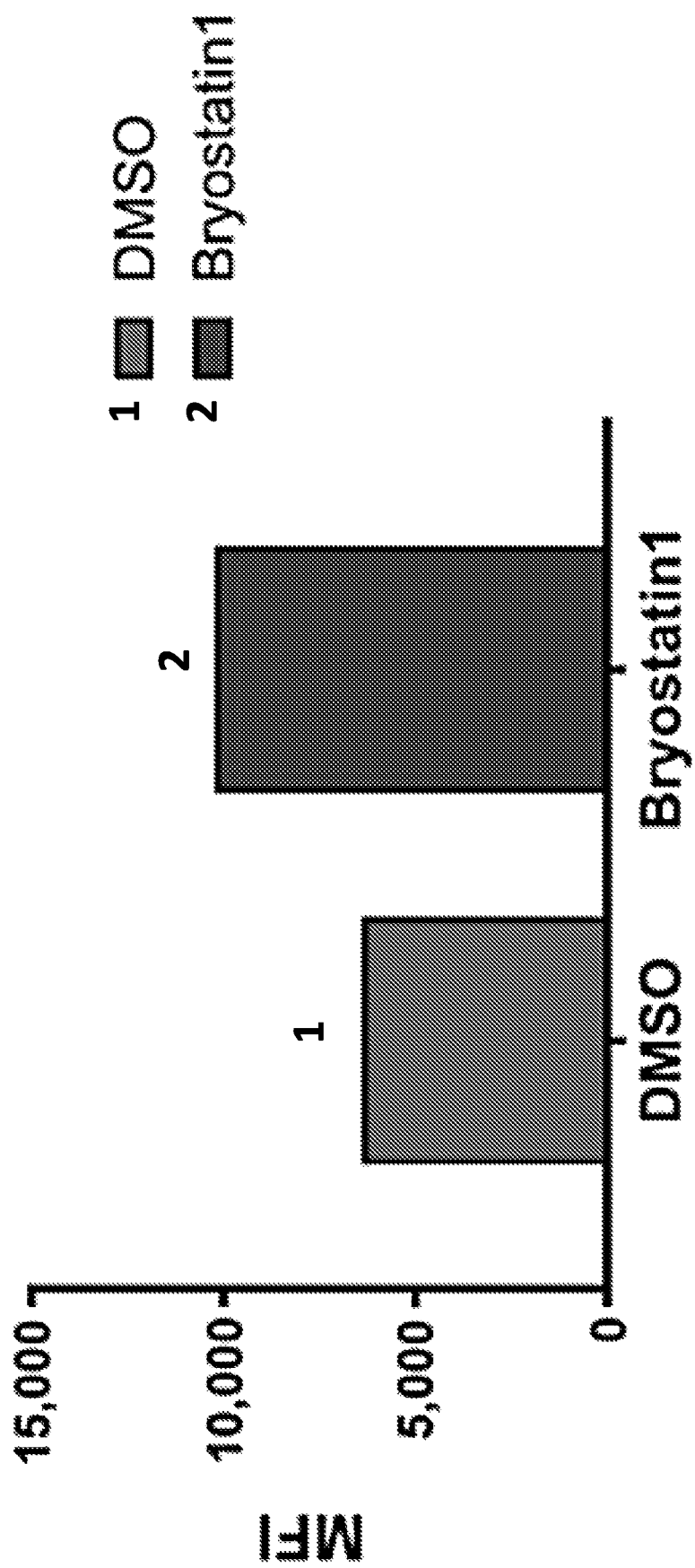

It was next evaluated whether a drug-mediated increase in antigen expression would improve CAR activity. Bryostatin 1 has been shown to increase CD22 expression on chronic lymphocytic leukemia (CLL) (Viola Biberacher et al., *Haematologica*. 2012; 97(5):771-779). Thus, the impact of Bryostatin 1 on CD22 expression was tested in two pre-B acute lymphoblastic leukemia cell lines and two diffuse large B cell lymphoma (DLBCL) cell lines. All four cell lines demonstrated a significant increase in CD22 expression (FIG. 3A) upon exposure to Bryostatin 1. Although Bryostatin 1 did not alter CD19 expression on ALL, there was a modest increase on DLBCL (FIG. 3A). Increased CD22 expression persisted for a week following removal of Bryostatin 1 (FIG. 3B). Furthermore, a single dose of Bryostatin 1 administered intraperitoneally (I.P.) increased CD22 MFI on Nalm6 at 1 week followed by a return to baseline expression at 12 days post-drug administration (FIG. 3C). Finally, it was confirmed that Bryostatin 1 upregulated CD22 on a CD22-low relapse patient-derived ALL xenograft (FIG. 3D).

Figure 4A:
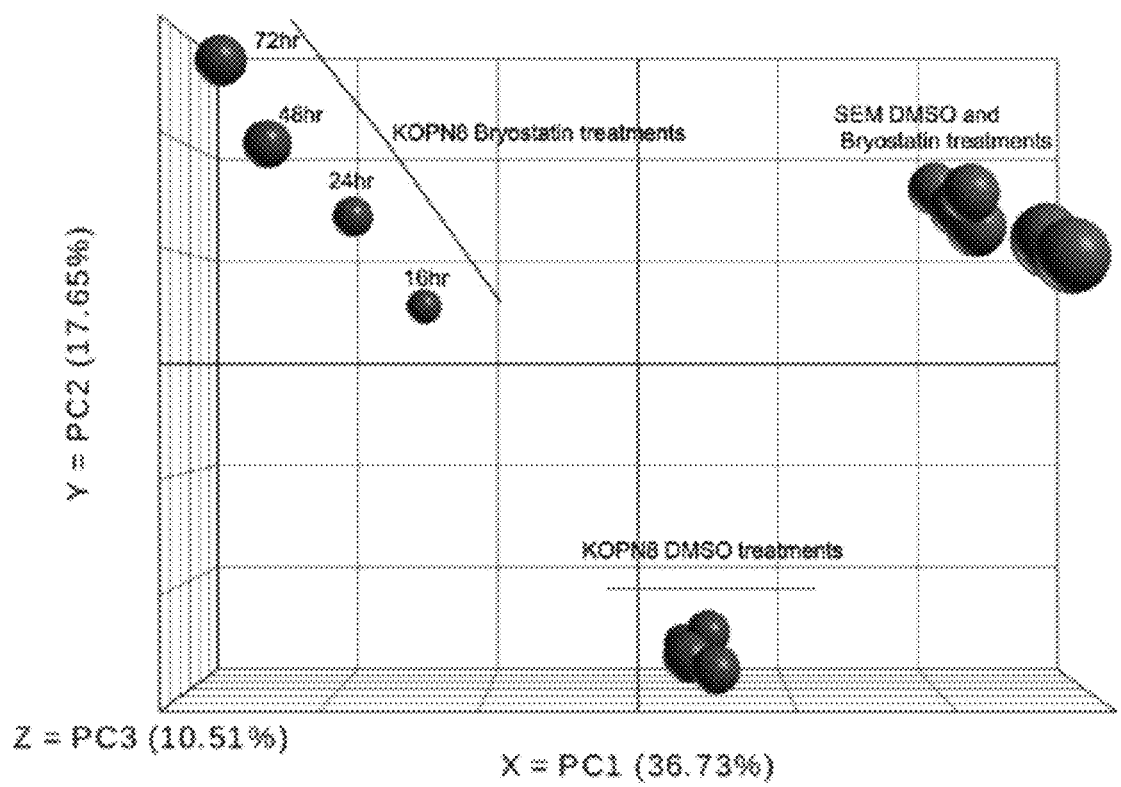
FIGS. 4A-4E.
Figure 4B:
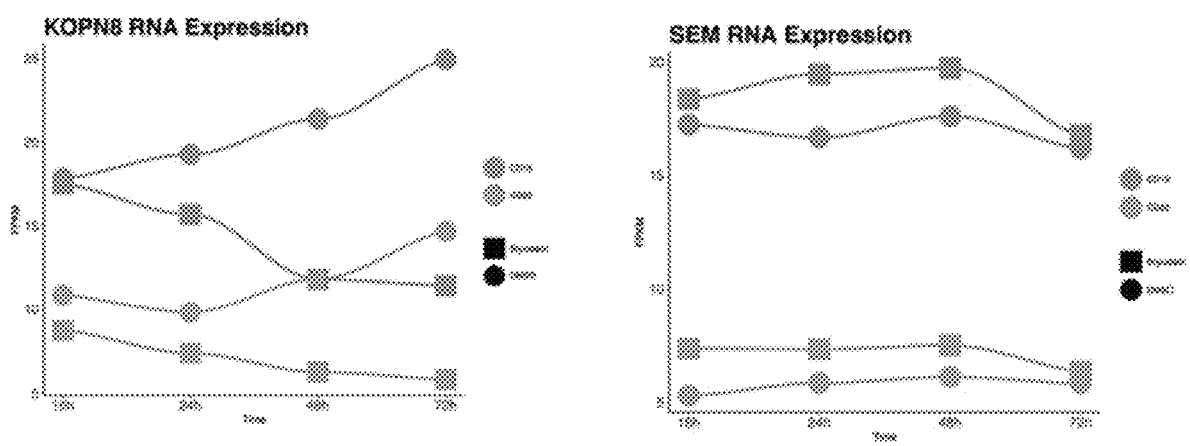
Figure 10A:
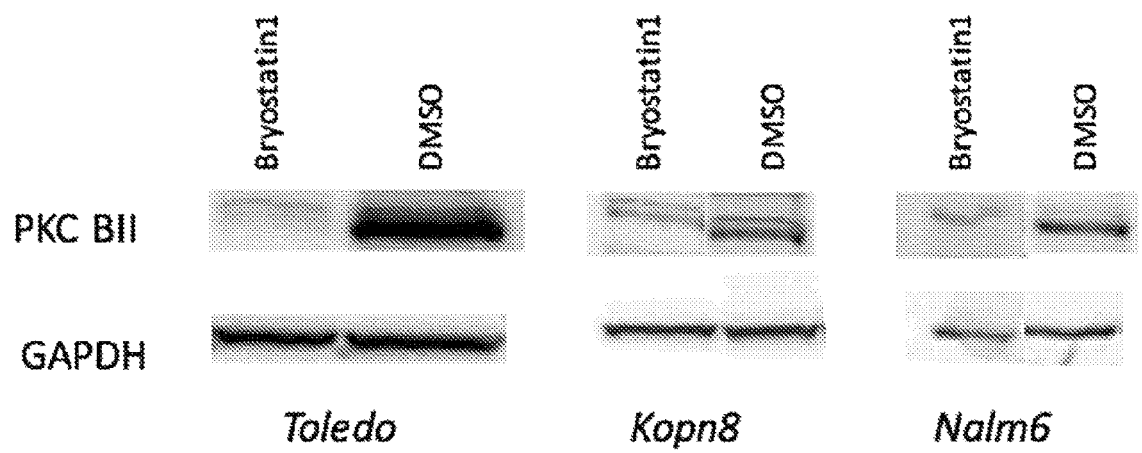
Figure 10C:
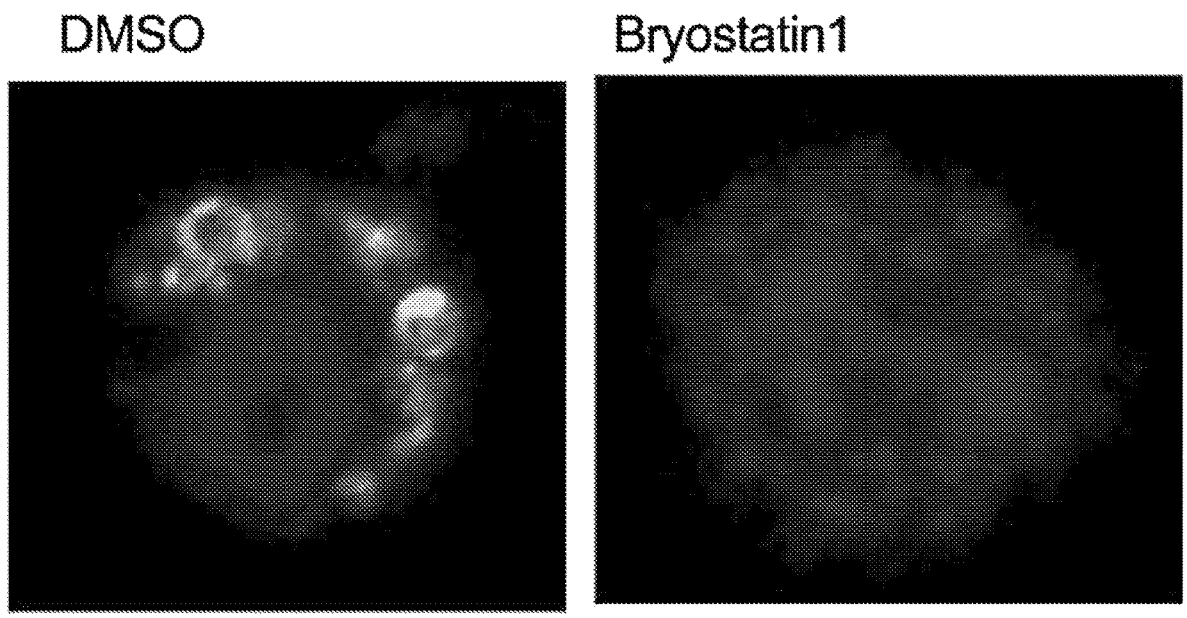
Figure 10B:
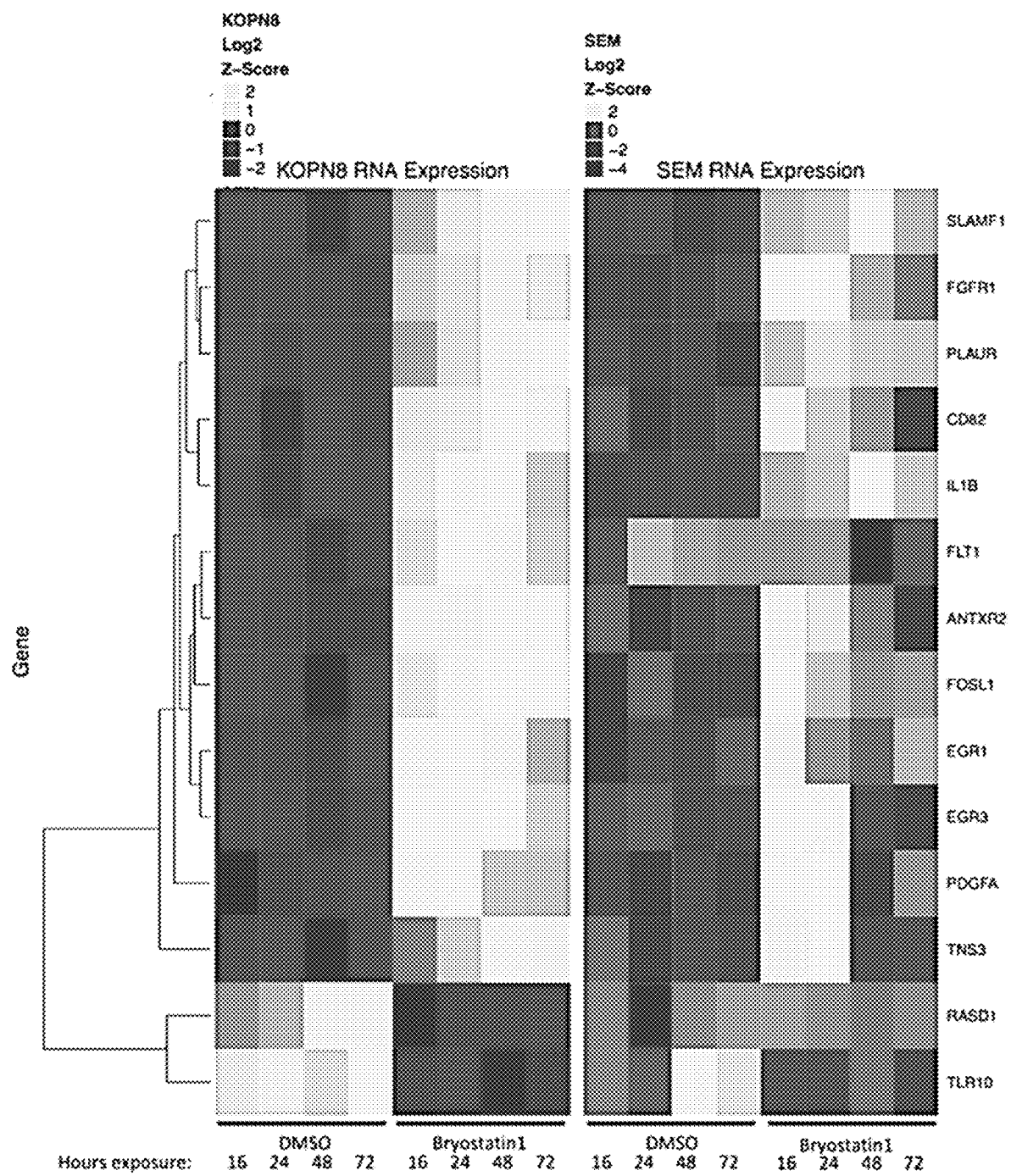
Figure 10E:
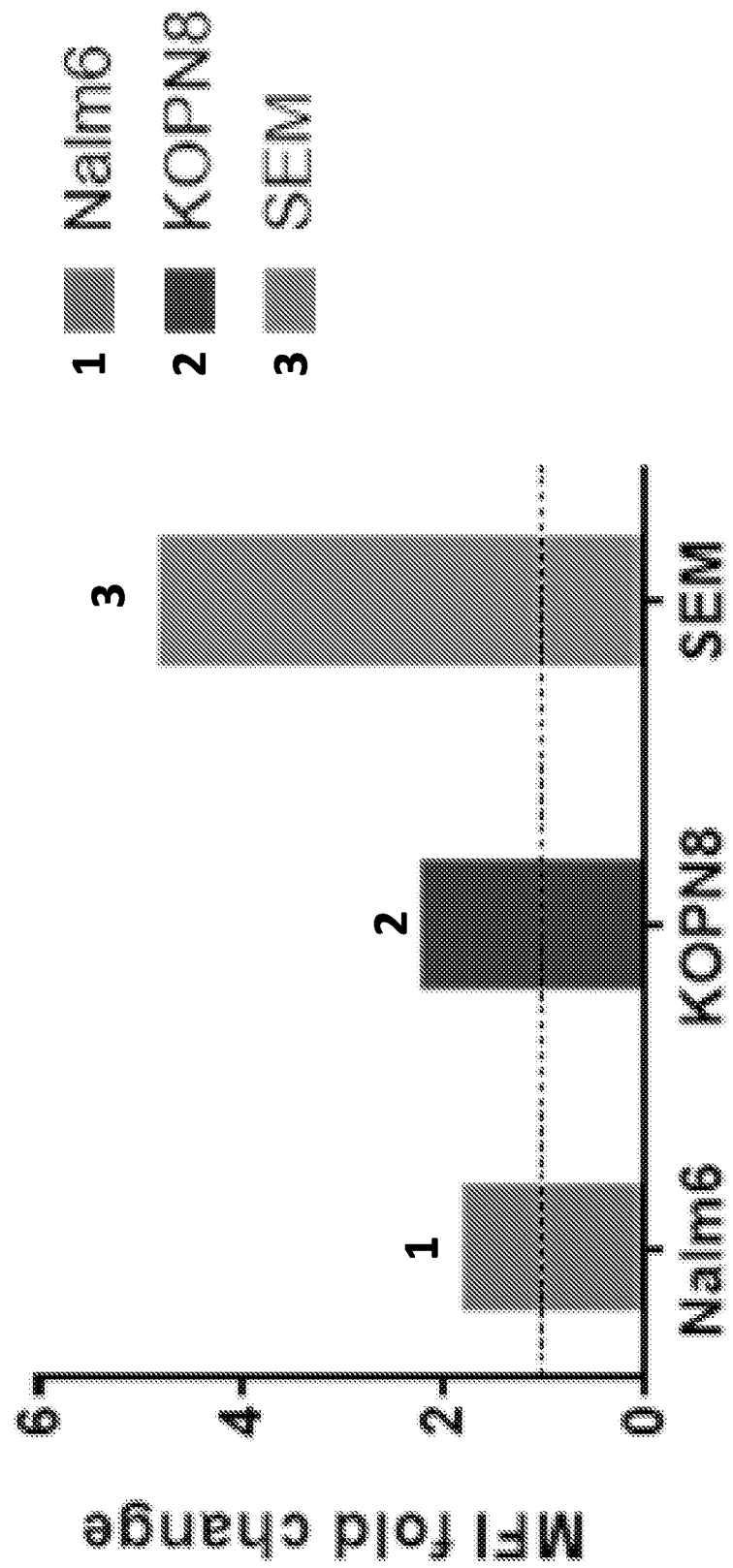

Bryostatin 1-Mediated CD22 Upregulation May Occur Via Mechanisms Other than Increased CD22 Gene Expression Mediated by PKC Inhibition As previously described for Bryostatin 1, effects on CLL in the setting of CD22 upregulation (Viola Biberacher et al., *Haematologica*. 2012; 97(5):771-779), PKCβII protein levels decreased on ALL upon exposure to Bryostatin 1 (FIG. 10), indicating a similar PKC-driven mechanism. However, neither the PKCβII inhibitor, Enzastaurin, nor a broad PKC inhibitor, Staurosporine, was able to upregulate CD22 (FIG. 10D). To further investigate potential mechanisms of CD22 upregulation, RNA-sequence analysis (RNAseq) was conducted on Bryostatin 1-treated and untreated ALL cell lines KOPN8 (MLL-MLLT1 fusion oncogene) and SEM (MLL-AFF1 fusion oncogene), both of which show robust upregulation of CD22 with Bryostatin 1 exposure (FIG. 10E). There were marked differences between the two cell lines in the magnitude of the transcriptional response to Bryostatin 1 (FIG. 4A). KOPN8 demonstrated 1524 genes with a greater than 2-fold change at 24 hours. Although only one gene demonstrated a 2-fold change with Bryostain1 exposure in SEM, a common set of genes was upregulated in both cell lines, including several cell surface proteins such as CD82, FLT1, FGFR1, and TLR10. Neither cell line showed changes in the CD22 mRNA over the course of Bryostatin 1 treatment (FIG. 4B). Using the 756 genes with 2-fold increased expression versus control in KOPN8 and GSEA, significant enrichment in genes known as intrinsic components of plasma membrane was found. Based on this observation and the unaltered CD22 RNA expression, it was hypothesized that Bryostatin 1 might increase CD22 through altered trafficking of membrane bound proteins. Consistent with this, Bryostatin 1-treated cells demonstrated less vacuolated CD22 at 24 hours after exposure compared to DMSO controls (FIG. 10C).

Figure 4C:
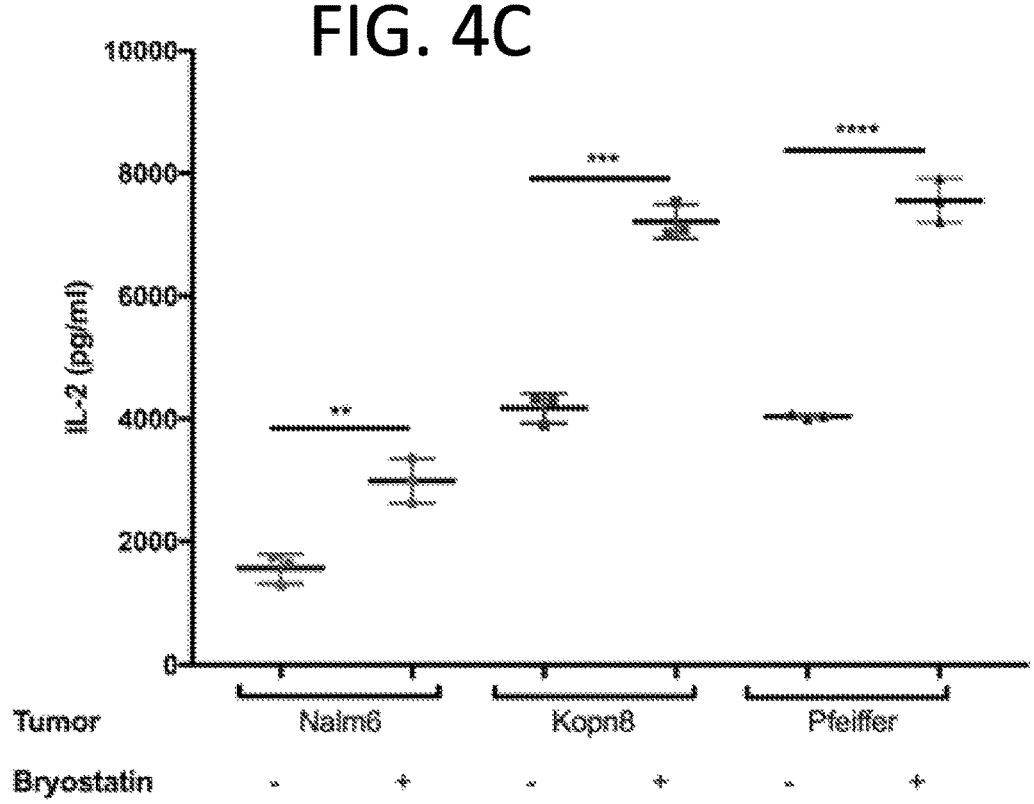
Figure 4D:
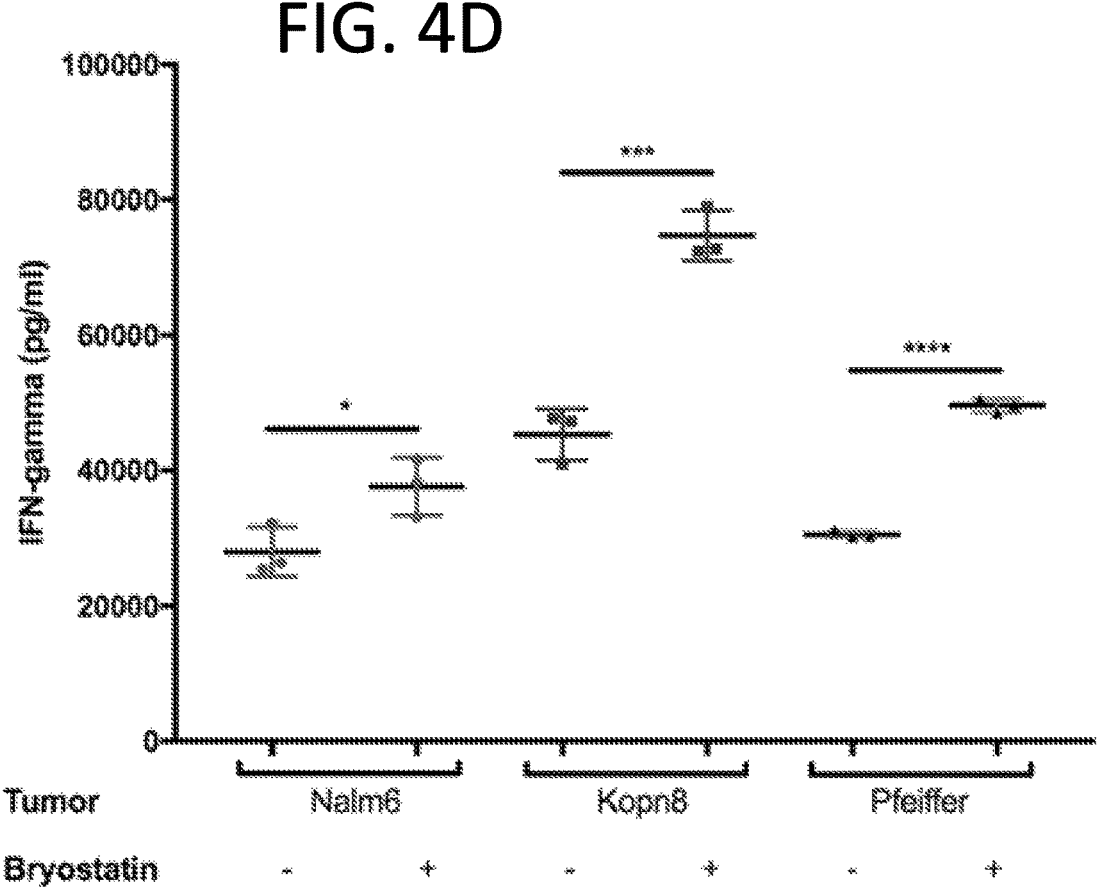
Figure 4E:
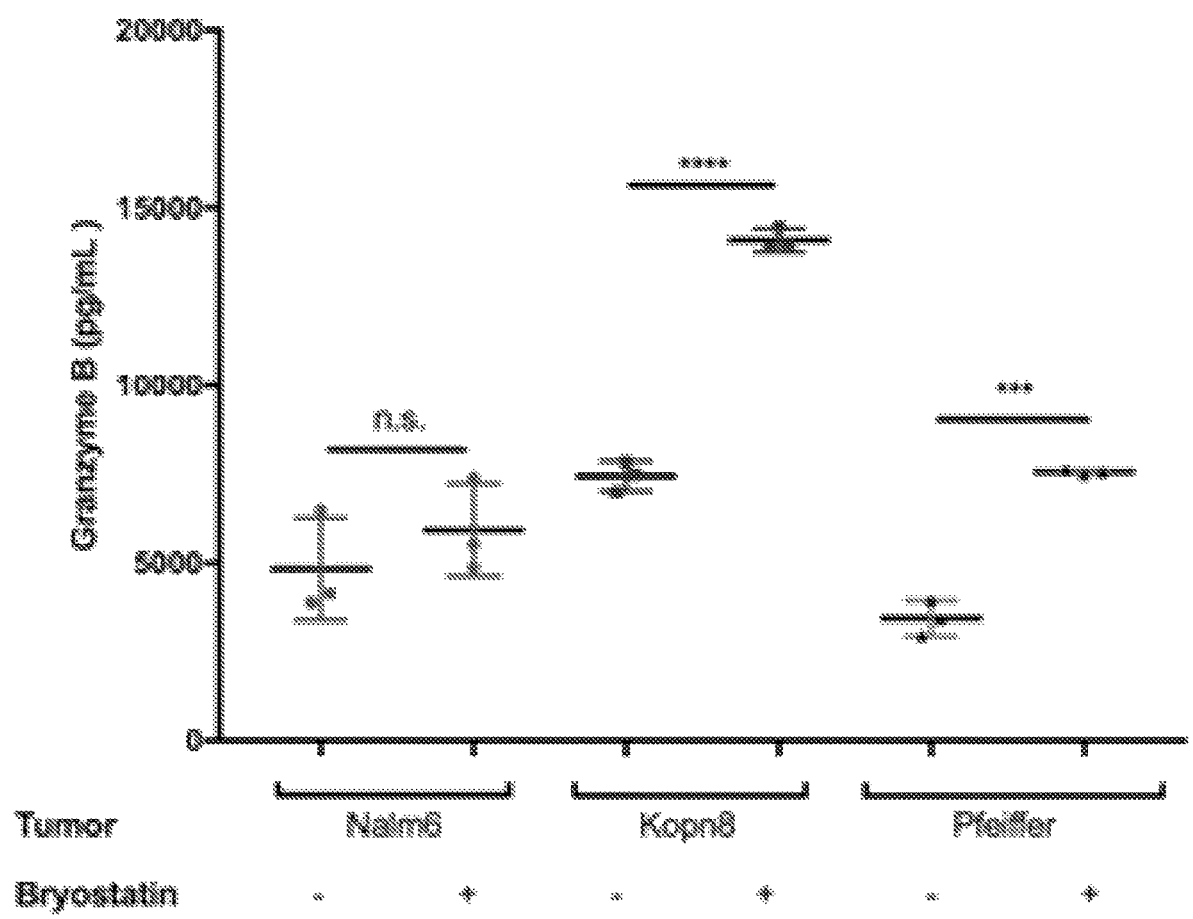

In Vitro CD22 CART Functionality, but not CD19 CART, is Enhanced Following Bryostatin 1 Priming of Leukemia Cells Additional studies sought to determine whether Bryostatin 1-mediated increase in CD22 site density on leukemia could enhance the functionality of CD22 CAR T cells. Bryostatin 1 pre-treatment of both B-ALL and DLBCL significantly enhanced production of IL-2, IFN-γ, and granzyme B by the CD22 CAR (FIGS. 4C-4D). Moreover, in vitro cytotoxicity was enhanced, as measured by granzyme B (FIG. 4E). Conversely, the CD19 CAR did not show improved Granzyme B production with the leukemia exposure to Bryostatin 1 (FIG. 14A). However, Bryostatin 1 did not reduce efficacy of the CD19 CAR in vivo (FIG. 14B).

Figure 5B:
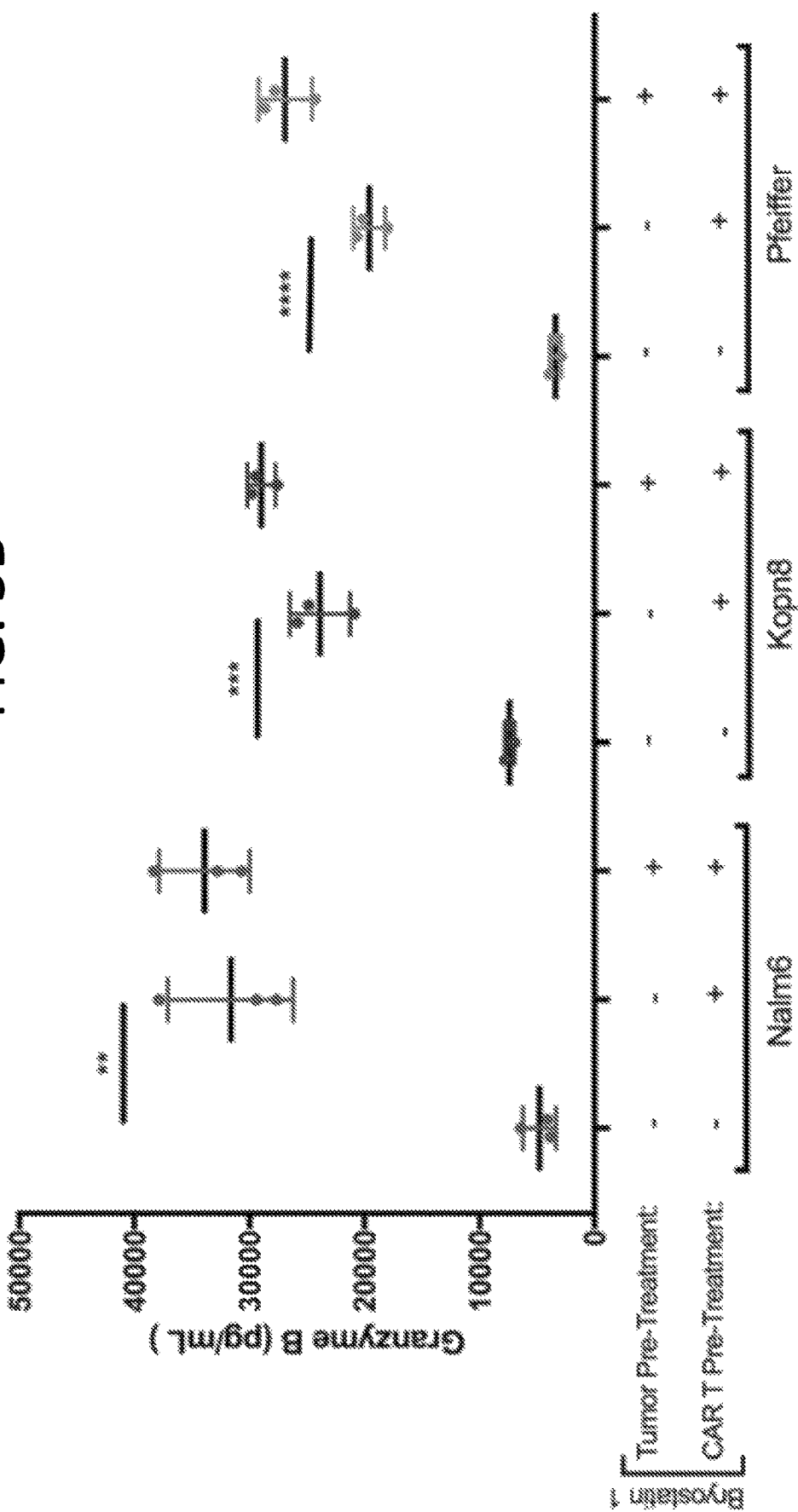
Figure 5D:
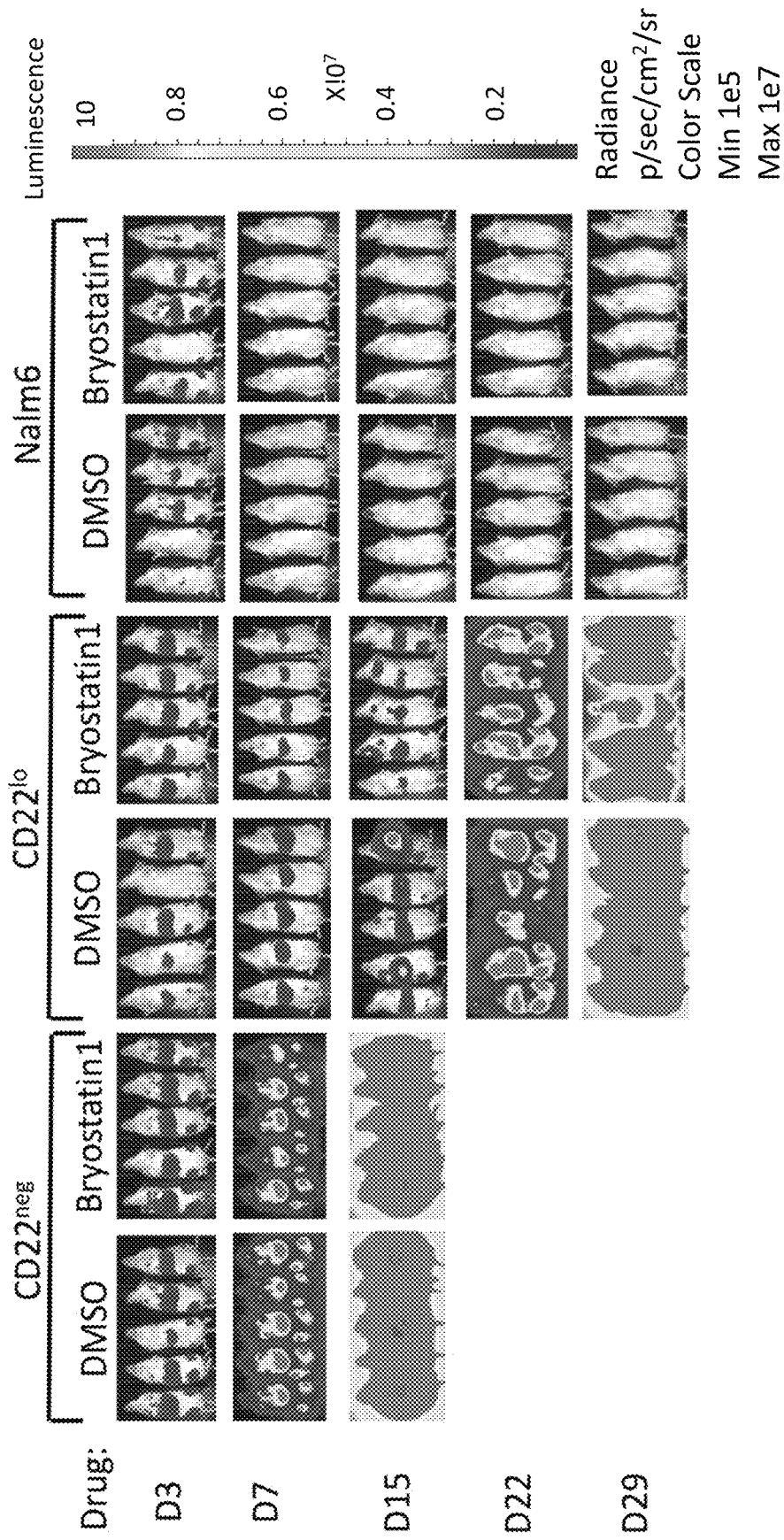
Figure 11:
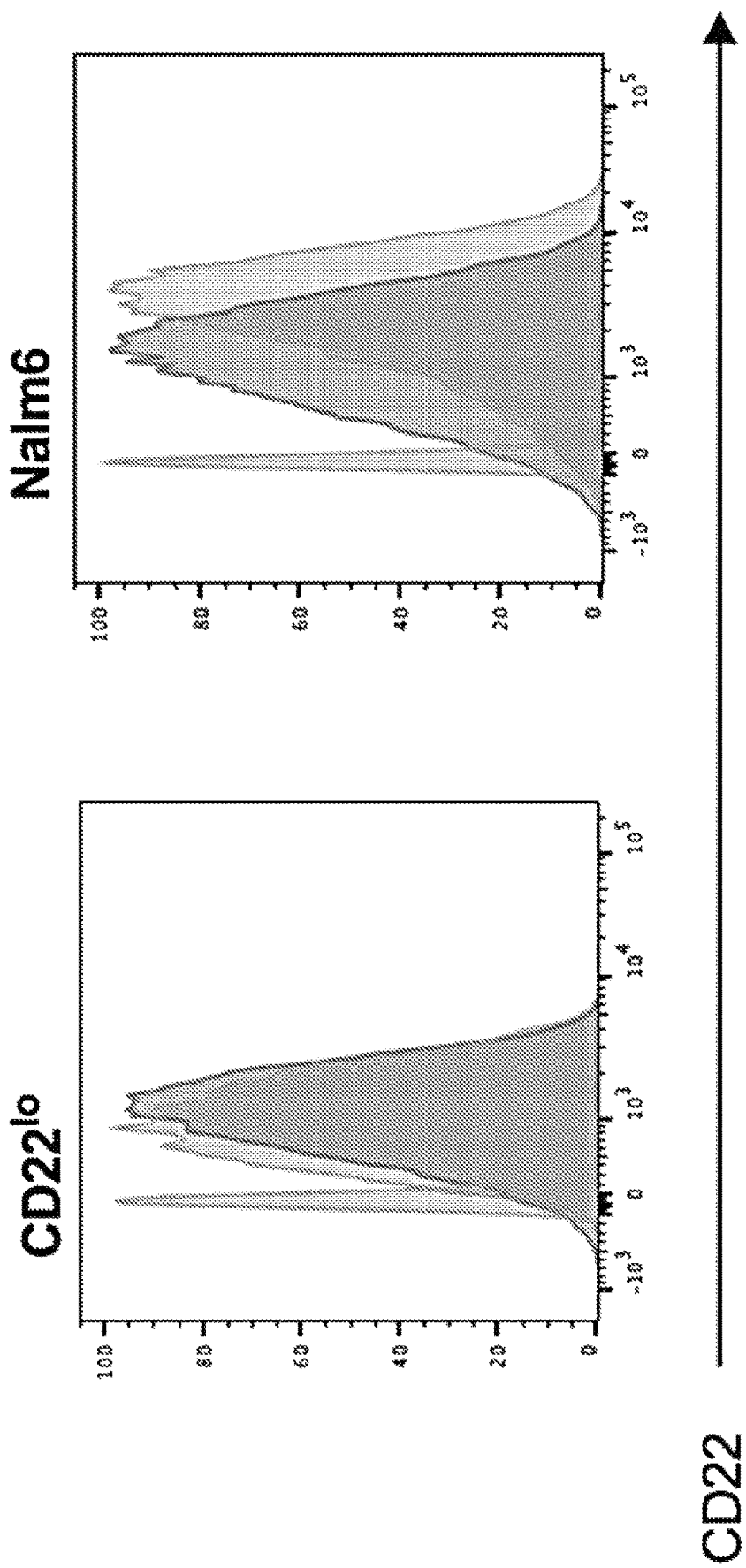
FIG. 11: $CD22^{lo}$ or parental Nalm6 cell lines were exposed to 1 ng/ml Bryostatin 1 for 24 hours. CD22 expression was assessed using flow cytometry.

Exposure of CART to Bryostatin 1 Attenuates Cytokine Production but does not Affect In Vitro Cytotoxicity Bryostatin 1 has been characterized as a modulator of PKC isoforms, which play important roles in the T cell receptor signaling pathways (Tuttle et al., *J Surg Res*. 1992; 52(6):543-548; Drexler et al., *Blood*. 1989; 74(5):1747-1757). With the clinical goal of utilizing Bryostatin 1 in conjunction with CAR therapy, it was evaluated whether Bryostatin 1 treatment directly impacts CD22 CAR functionality independent of its effects on leukemic site density. CD22 CAR pre-treated with Bryostatin 1 produced attenuated levels of IFN-γ when co-cultured with ALL or DLBCL cell lines relative to DMSO-control pre-treated CD22 CAR, but produced significantly increased levels of granzyme B (FIGS. 5A-5B). To determine the impact of Bryostatin 1 effects on CD22 CAR cytokine and granzyme B production, cytotoxicity of Bryostain1-exposed CAR T cells was evaluated and no change was found in the kinetics of leukemic clearance in vitro (FIG. 5C). Bryostatin 1 effects on CAR activity in vivo were evaluated in the absence of target antigen modulation using the CD22$^{lo}$ leukemia cells, which did not demonstrate an increase in CD22 expression following Bryostatin 1 exposure (FIG. 11). As shown in FIG. 5D, Bryostatin 1 did not impact the ability of CD22-CAR to attenuate progression of the CD22$^{lo}$ leukemia in vivo. Together, these findings indicate that exposing CD22 CAR to Bryostatin 1 changes cytokine and granzyme B secretion, but does not negatively impact overall CAR functionality.

Figure 6A:
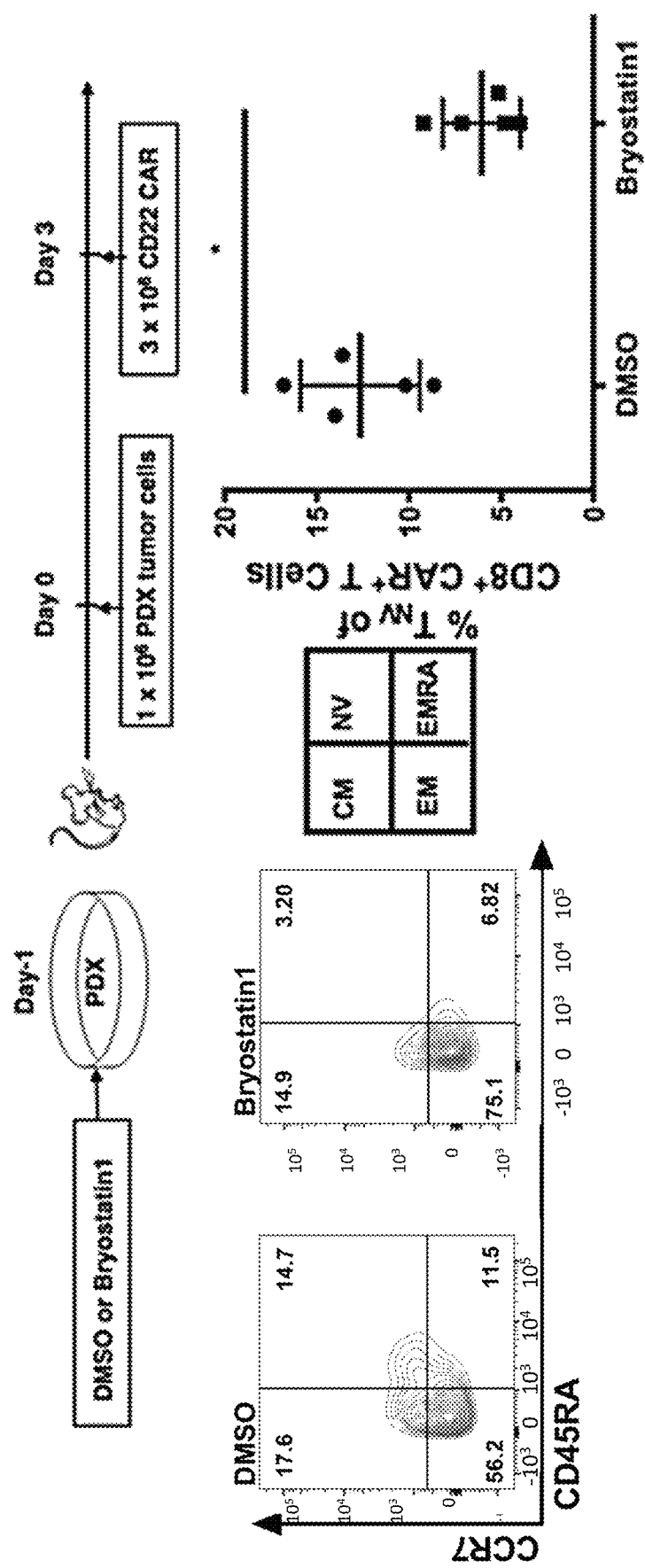
Figure 6B:
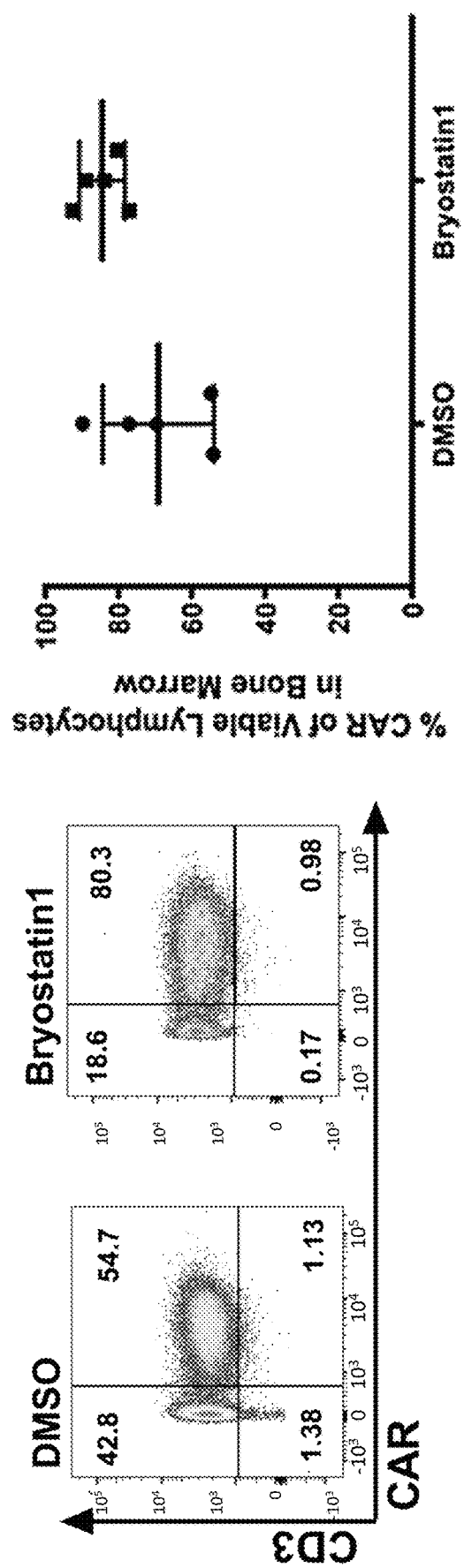
Figure 14C:
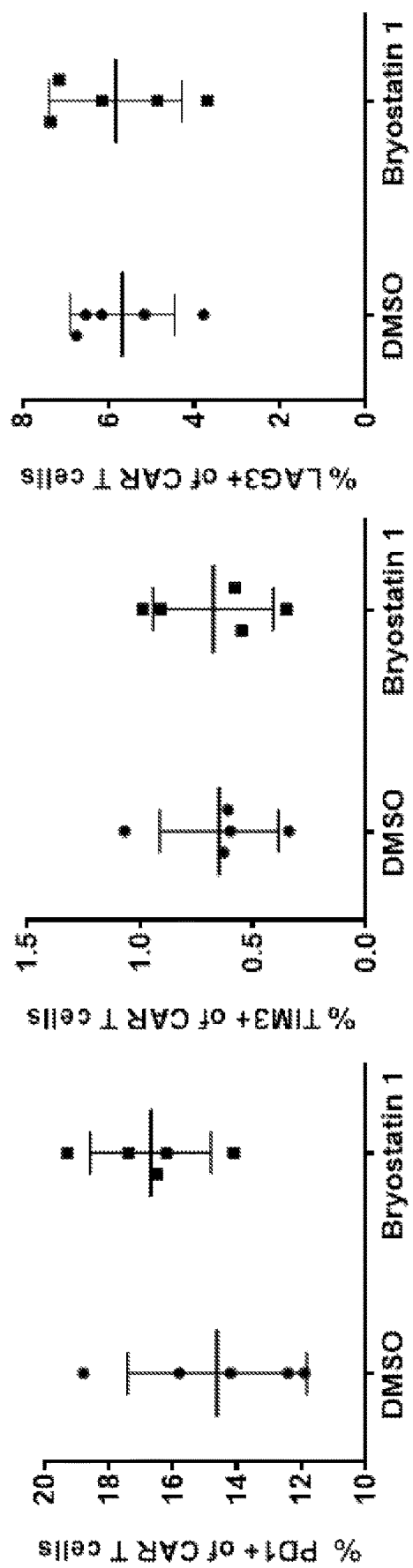

Bryostatin 1 Affects CAR T Cell Persistence, Memory Phenotype, and Improves Durability of Leukemic Response The impact of Bryostatin 1-mediated increase in CD22 site density on in vivo CAR persistence and functionality was evaluated using the parental Nalm6, which does not express sufficient CD22 to maximize cytokine response (FIG. 2G) and does modulate CD22 expression in response to Bryostatin 1 (FIG. 3). The administration of Bryostatin 1 as a "priming therapy" prior to CART infusion was tested. Mice were injected with Bryostatin 1 pretreated tumor cells, followed by CART injection. Seven days after CD22 CAR injection, T-cell phenotype was evaluated. Within the CD8$^+$ CART population, significant cumulative enrichment of central memory (CCR7$^+$, CD45RA$^-$) and effector memory (CCR7$^-$, CD45RA$^-$) cells were found, and fewer naïve cells, in the spleens of mice that received Bryostatin 1 pretreated Nalm6 (FIG. 6A). With Bryostatin 1 exposure, CART demonstrated similar activation without evidence of exhaustion, as evidenced by stable PD1 expression, without increase in TIM3 or LAGS (FIG. 14C). At 30 days, mice treated with Bryostatin 1 after CART injection had slightly increased CD22 CART in bone marrow (FIG. 6B). Bryostatin 1 administration for 2 weeks after subcurative dose of CD22 CART infusion was then tested in Nalm6 (FIG. 6C; FIG. 15A) and SEM (FIG. 6C; FIG. 15B), demonstrating that Bryostatin 1 improved durability of remission, extending beyond cessation of Bryostatin 1. Finally, the effects of Bryostatin 1 administration following CD22 CART infusion was tested in the CD22-low relapse PDX model, demonstrating improved ability to clear leukemia (FIG. 6D; FIG. 15C). Collectively, these results demonstrate that Bryostatin 1 is effective as both a priming therapy to increase antigen expression prior to CAR T-cell infusion and as a rescue following emergence of CD22 CAR-resistant leukemia.

Therapeutic Applications

Relapsed or refractory pre-B cell ALL patients have a potentially curative therapeutic option in CAR T cell therapy; however, some of these patients have relapsed because of target antigen modulation. Furthermore, recent studies have to identified limitations in CAR activity in the setting of low antigen site density (Walker et al., *Mol Ther.* 2017; 25(9):2189-2201; Chmielewski et al., *Gene Ther.* 2011; 18(1):62-72; Yoshida et al., *Clin Transl Immunology.* 2016; 5(12):e116; Watanabe et al., *J Immunol.* 2015; 194 (3):911-920; Weijtens et al., *Gene Ther.* 2000; 7(1):35-42; Turatti et al., *J Immunother.* 2007; 30(7):684-693; James et al., *J Immunol.* 2008; 180(10):7028-7038; Anurathapan et al., *Mol Ther.* 2014; 22(3):623-633; Caruso et al., *Cancer Res.* 2015; 75(17):3505-3518; Hombach et al., *Mol Ther.* 2016; 24(8):1423-1434; Hegde et al., *J Clin Invest.* 2016; 126(8):3036-3052). Clinical experience supports low antigen density as a mechanism of escape from CAR-targeted therapy and, potentially, decreased CAR-T cell expansion and functionality (Fry et al., *Nat Med.* 2018; 24(1):20-28). The studies disclosed herein evaluate the characteristics of CAR failure in the setting of low site density, specifically focusing on the effects of low site density on CAR function and persistence. Moreover, the present disclosure provides the first preclinical evidence to support the use of therapeutic antigen modulation to overcome such limitations. The data established two important findings: (A) low site density on tumor cells results in significant changes in persistence and phenotype of the CAR T cells, and (B) increasing site density improves CAR T cell functionality.

It has been previously demonstrated that treatment of patients with pre-B ALL using CD22 CART is often followed by progressive or relapsed leukemia expressing lower CD22 in a high proportion of patients responding to CD22 CART cells. Furthermore, pre-B ALL has a baseline CD22 expression that is significantly lower than CD19 expression, even prior to exposure to immunotherapeutic pressure. The present disclosure demonstrates the specific effects of site density on cytokine production and cytotoxicity, and is consistent with previous studies (Walker et al., *Mol Ther.* 2017; 25(9):2189-2201; Watanabe et al., *J Immunol.* 2015; 194(3):911-920; Hombach et al., *Mol Ther.* 2016; 24(8): 1423-1434; Hegde et al., *J Clin Invest.* 2016; 126(8):3036-3052). This analysis of CAR T cell potency relative to site density is extended to an in vivo system, demonstrating delay in progression, but failure to clear leukemia expressing low site density antigen. The impact of low site density on CAR T cell persistence and phenotype is also defined.

While activation markers were not significantly altered, higher site density leukemia resulted in an increased number of persisting CAR T cells and a higher proportion of central and effector memory CD8+ CAR T cells. This is the first clear evidence that site density not only affects short-term activity of CAR T cells, but also affects longer-term persistence and memory development with implications for the durability of CAR T-induced remissions.

Strategies to overcome the limitations on cellular therapy imposed by low site density antigen were evaluated, including by enhancing the affinity of the CD22 CAR to improve CAR sensitivity to low site density. Although binding affinity is important for antibody-based therapeutics, affinity enhancement of the CD22 CAR did not enhance response to, or clearance of, low site density leukemia. However, this may not be the case for other CAR constructs and the corresponding targeted antigens (Turatti et al., *J Immunother.* 2007; 30(7):684-693; Lynn et al., *Leukemia.* 2016; 30(6):1355-1364). Second, Bryostatin 1 was identified as a drug to upregulate CD22 expression in ALL and DLBCL cell lines, thereby improving CART cytokine production and memory phenotype. As a modulator of PKC, Bryostatin 1 has variable effects on PKC levels based on exposure parameters (Isakov et al., *J Immunol.* 1993; 150(4):1195-1204; Lee et al., *Am J Physiol.* 1996; 271(1 Pt 1):C304-311; Grant, *Front Biosci.* 1997; 2:d242-252; Grant et al., *Cancer Res.* 1992; 52(22):6270-6278; Jarvis et al., *Biochem Pharmacol.* 1994; 47(5):839-852). In CLL, Bryostatin 1-mediated upregulation of CD22 correlated with decreased PKC (Viola Biberacher et al., *Haematologica.* 2012; 97(5):771-779). Initial evaluation of the mechanism of action of Bryostatin 1 found that while decreased PKC-βII levels were observed, PKC modulation may not be the sole cause of CD22 regulation. Specifically, it was found that CD22 mRNA levels were not significantly altered in Bryostatin 1-treated ALL cell lines and that multiple cell surface molecules were up-regulated.

Since CAR functionality was significantly improved by the increase in CD22 expression mediated by Bryostatin 1 and since Bryostatin 1 has been previously implicated in affecting T cell function (Tuttle et al., *J Surg Res.* 1992; 52(6):543-548; Drexler et al., *Blood.* 1989; 74(5):1747-1757), Bryostatin 1 direct effect on T cell function independent of target antigen modulation was analyzed. Although Bryostatin 1 did attenuate IFN-γ production, it also increased granzyme B production, with no negative effect on in vitro or in vivo cytotoxicity. Thus, the net effect of Bryostatin 1 on CART and leukemia resulted in overall augmented cytokine production and cytotoxicity, and improved durability of response. These findings provide validation for combining Bryostatin 1 with CART therapy. Bryostatin 1 can be used to prime tumors prior to CART therapy or to rescue patients following post-CART relapse resulting from reduced antigen expression.

Example 3: CD22-Specific Monoclonal Antibodies for Detecting a B-Cell Malignancy in a Subject or Confirming the Diagnosis of a B-Cell Malignancy in a Subject This example describes an exemplary use of CD22-specific human monoclonal antibodies for the detection of a B-cell malignancy in a subject. This example further describes the use of these antibodies to confirm the diagnosis of a B-cell malignancy in a subject.

Levels of soluble CD22 are elevated in subjects with B-cell malignancies, relative to healthy subjects. Thus, detection and quantitation of sCD22 in patients diagnosed with, or suspected of having a B-cell malignancy, can be used to detect a B-cell malignancy or confirm the diagnosis of a B-cell malignancy in a subject. A blood sample is obtained from the patient diagnosed with, or suspected of having a B-cell malignancy. A blood sample taken from a patient that does not have B-cell malignancy can be used as a control.

In this example, a sandwich ELISA is performed to detect sCD22 in the blood samples. Human monoclonal anti-CD22 antibody (such as m971-L7) is immobilized on the surface of a multi-well flat-bottomed plate (such as a 96- or 364-well plate) by coating the plate with the antibody and incubating for 2 hours at room temperature. After washing the plate twice with 0.02% Tween PBS (T-PBS), the plate is blocked with 1% bovine serum albumin (BSA)-PBS to preclude nonspecific binding, then washed twice with T-PBS. The patient and control samples are added to the wells and incubated for approximately 15-20 hours. After washing with T-PBS three times, a second anti-CD22 antibody directly labeled with a label (such as horseradish peroxidase (HRP)) is added to the plate. After three more washes with T-PBS, 100 µl of 10,000-fold diluted Avidine-HRP solution (Biosource) is added and incubated 1 hour at room temperature. After three more washes with T-PBS, 100 µl of TMB solution (Pierce) and 100 µl of $H_2O_2$ are added (e.g., if HRP is the label) and incubated for 5 minutes, followed by the addition of 100 µl of 2N $H_2SO_4$ to stop the color development (e.g., if HRP is the label). The levels of sCD22 are determined by measuring the optical density (OD) value at 450 nm (or other wavelength depending on the label used).

An increase in the level of sCD22 in the patient sample, relative to the control sample, indicates that the subject has a B-cell malignancy. Thus, detection of sCD22 can be used to detect a B-cell malignancy in a subject, or confirm the diagnosis of a B-cell malignancy in a subject.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A monoclonal antibody that binds CD22, or an antigen-binding fragment thereof, comprising a variable heavy (VH) domain and a variable light (VL) domain, wherein:
   the VH domain comprises the complementarity determining region (CDR) sequences of SEQ ID NO: 4; and
   the VL domain comprises the CDR sequences of SEQ ID NO: 5.

2. The monoclonal antibody or antigen-binding fragment of claim 1, wherein the CDR sequences are determined using the IMGT, Kabat, Paratome or Chothia numbering scheme.

3. The monoclonal antibody or antigen-binding fragment of claim 1, wherein:
   the VH domain comprises residues 26-35, 53-61 and 100-113 of SEQ ID NO: 4; and
   the VL domain comprises residues 27-32, 50-52 and 89-97 of SEQ ID NO: 5.

4. The monoclonal antibody or antigen-binding fragment of claim 1, wherein:
   the amino acid sequence of the VH domain is at least 90% identical to SEQ ID NO: 4 and comprises the CDR sequences of SEQ ID NO: 4; and
   the amino acid sequence of the VL domain is at least 90% identical to SEQ ID NO: 5 and comprises the CDR sequences of SEQ ID NO: 5.

5. The monoclonal antibody or antigen-binding fragment of claim 1, wherein:
   the amino acid sequence of the VH domain comprises SEQ ID NO: 4; and
   the amino acid sequence of the VL domain comprises SEQ ID NO: 5.

6. The antigen-binding fragment of claim 1, wherein the antigen-binding fragment is an Fab fragment, an Fab' fragment, an F(ab)'$_2$ fragment, a single chain variable fragment (scFv) or a disulfide stabilized variable fragment (dsFv).

7. The monoclonal antibody of claim 1, wherein the antibody is an IgG.

8. The monoclonal antibody or antigen-binding fragment of claim 1, which is a fully human antibody or antigen-binding fragment.

9. The monoclonal antibody or antigen-binding fragment of claim 1, which is a chimeric or synthetic antibody or antigen-binding fragment.

10. A chimeric antigen receptor (CAR) comprising the monoclonal antibody or antigen-binding fragment of claim 1.

11. The CAR of claim 10, further comprising a hinge region, a transmembrane domain, a costimulatory signaling moiety, a signaling domain, or any combination thereof.

12. An isolated cell expressing the CAR of claim 10.

13. The isolated cell of claim 12, which is a cytotoxic T lymphocyte (CTL).

14. An immunoconjugate comprising the monoclonal antibody or antigen-binding fragment of claim 1 and an effector molecule.

15. The immunoconjugate of claim 14, wherein the effector molecule is a toxin or a detectable label.

16. An antibody-drug conjugate (ADC) comprising a drug conjugated to the monoclonal antibody or antigen-binding fragment of claim 1.

17. A multi-specific antibody comprising the monoclonal antibody or antigen-binding fragment of claim 1 and at least one additional monoclonal antibody or antigen-binding fragment thereof.

18. An antibody-nanoparticle conjugate, comprising a nanoparticle conjugated to the monoclonal antibody or antigen-binding fragment of claim 1.

19. A fusion protein comprising the monoclonal antibody or antigen-binding fragment of claim 1 and a heterologous protein or peptide.

20. The fusion protein of claim 19, wherein the heterologous protein is an Fc protein.

21. A composition comprising a pharmaceutically acceptable carrier and the monoclonal antibody or antigen-binding fragment of claim 1.

22. A nucleic acid molecule encoding the monoclonal antibody or antigen-binding fragment of claim 1.

23. The nucleic acid molecule of claim 22, operably linked to a promoter.

24. A vector comprising the nucleic acid molecule of claim 22.

25. A method of detecting expression of CD22 in a sample, comprising:
   contacting the sample with the monoclonal antibody or antigen-binding fragment of claim 1; and
   detecting binding of the antibody to the sample, thereby detecting expression of CD22 in the sample.

26. The method of claim 25, wherein the monoclonal antibody or antigen-binding fragment is directly labeled.

27. The method of claim 25, further comprising:
   contacting the monoclonal antibody or antigen-binding fragment with a second antibody, and
   detecting the binding of the second antibody to the monoclonal antibody or antigen-binding fragment, thereby detecting expression of CD22 in the sample.

28. A method of treating a CD22-positive cancer in a subject, comprising administering to the subject a therapeutically effective amount of the isolated cell of claim 12, thereby treating the CD22-positive cancer.

29. The method of claim 28, wherein the CD22-positive cancer is a B-cell malignancy.

30. The method of claim 29, wherein the B-cell malignancy is acute lymphoblastic leukemia (ALL), non-Hodgkin's lymphoma, Burkitt's lymphoma, small lymphocytic lymphoma, primary effusion lymphoma, diffuse large B-cell lymphoma, splenic marginal zone lymphoma, mucosa-associated lymphoid tissue (MALT) lymphoma, hairy cell leukemia, chronic lymphocytic leukemia or B-cell prolymphocytic leukemia.

31. The method of claim 28, further comprising administering a therapeutically effective amount of Bryostatin 1 to the subject.

32. The method of claim 31, wherein Bryostatin 1 is administered prior to or simultaneously with administration of the isolated cell.

33. A kit, comprising:
   the monoclonal antibody or antigen-binding fragment of claim 1, and
   an agent that upregulates CD22 expression.

34. The kit of claim 33, wherein the agent that upregulates CD22 expression comprises or consists of Bryostatin 1.

35. The kit of claim 33, further comprising an anti-cancer agent.

* * * * *